United States Patent
Khalil et al.

(10) Patent No.: US 10,138,493 B2
(45) Date of Patent: Nov. 27, 2018

(54) SYNTHETIC TRANSCRIPTIONAL AND EPIGENETIC REGULATORS BASED ON ENGINEERED, ORTHOGONAL ZINC FINGER PROTEINS

(71) Applicants: TRUSTEES OF BOSTON UNIVERSITY, Boston, MA (US); THE GENERAL HOSPITAL CORPORATION, Boston, MA (US)

(72) Inventors: Ahmad S. Khalil, Lexington, MA (US); Divya Israni, Boston, MA (US); Minhee Park, Boston, MA (US); J. Keith Joung, Winchester, MA (US); Jeffry D. Sander, Ankeny, IA (US)

(73) Assignees: TRUSTEES OF BOSTON UNIVERSITY, Boston, MA (US); THE GENERAL HOSPITAL CORPORATION, Boston, MA (US)

(*) Notice: Subject to any disclaimer, the term of this patent is extended or adjusted under 35 U.S.C. 154(b) by 0 days.

(21) Appl. No.: 15/686,419

(22) Filed: Aug. 25, 2017

(65) Prior Publication Data
US 2018/0057838 A1 Mar. 1, 2018

Related U.S. Application Data

(60) Provisional application No. 62/450,459, filed on Jan. 25, 2017, provisional application No. 62/379,490, filed on Aug. 25, 2016.

(51) Int. Cl.
| | |
|---|---|
| *C12N 15/85* | (2006.01) |
| *C07K 14/47* | (2006.01) |
| *C07K 14/00* | (2006.01) |
| *C12N 15/113* | (2010.01) |

(52) U.S. Cl.
CPC ............. *C12N 15/85* (2013.01); *C07K 14/00* (2013.01); *C07K 14/47* (2013.01); *C12N 15/113* (2013.01); *C07K 2319/81* (2013.01); *C12N 2810/50* (2013.01); *C12N 2830/002* (2013.01)

(58) Field of Classification Search
None
See application file for complete search history.

(56) References Cited

U.S. PATENT DOCUMENTS

| | | |
|---|---|---|
| 8,242,242 B2 | 8/2012 | Kim et al. |
| 9,359,599 B2 | 6/2016 | Liu et al. |
| 2003/0105045 A1 | 6/2003 | Stanojevic |
| 2012/0178647 A1 | 7/2012 | Joung et al. |

OTHER PUBLICATIONS

Beerli et al. Toward controlling gene expression at will: Specific regulation of the erbB-2/HER-2 promoter by using polydactyl zinc finger proteins constructed from modular building blocks. Proceedings of the National Academy of Sciences, USA, vol. 95, pp. 14628-14633, Dec. 1998. (Year: 1998).*
Nolte et al. Differing roles for zinc fingers in DNA recognition: Structure of a six-finger transcription factor IIA complex. Proceedings of the National Academy of Sciences, USA, vol. 95, pp. 2938-2943, Mar. 1998. (Year: 1998).*
Krizek et al. A consensus of zinc finger peptide: Design, high-affinity metal binding, a pH-dependent structure, and a His to Cys sequence variant. Journal of the American Chemical Society, vol. 113, pp. 4518-4523, 1991. (Year: 1991).*
Payre et al. Genomic targets of the serendipity beta and delta zinc finger proteins and their respective DNA recognition sites. The EMBO Journal, vol. 10, No. 9, pp. 2533-2541, 1991. (Year: 1991).*
Beerli et al., "Engineering polydactyl zinc-finger transcription factors." Nature Biotechnology 20(2):135-141 (2002).
Garg et al., "Engineering synthetic TAL effectors with orthogonal target sites." Nucleic Acids Research 40 (15):7584-7595 (2012).
Khalil et al., "A synthetic biology framework for programming eukaryotic transcription functions." Cell 150(3):647-658 (2012).
Maeder et al., "Oligomerized Pool ENgineering (OPEN): An "Open-Source" Protocol for Making Customized Zinc Finger Arrays." Nature Protocols 4(10):1471-1501 (2009).
Maeder et al., "Rapid "open-source" engineering of customized zinc-finger nucleases for highly efficient gene modification." Molecular Cell 31(2):294-301 (2008).
Jattanayak et al., "Revealing off-target cleavage specificities of zinc-finger nucleases by in vitro selection." Nature Methods 8(9):765-770 (2011).
Sander et al., "In silico abstraction of zinc finger nuclease cleavage profiles reveals an expanded landscape of off-target sites." Nucleic Acids Research 41(19):e181 (2013).
Sander et al., "Selection-free zinc-finger-nuclease engineering by context-dependent assembly (CoDA)." Nature Methods 8(1):67-69 (2011).
Sander et al., "ZiFiT (Zinc Finger Targeter): an updated zinc finger engineering tool." Nucleic Acids Research 38 (suppl_2):W462-W468 (2010).
Polstein et al., "Light-inducible spatiotemporal control of gene activation by customizable zinc finger transcription factors." Journal of the American Chemical Society 134(40):16480-16483 (2012).

* cited by examiner

*Primary Examiner* — Jennifer Dunston
(74) *Attorney, Agent, or Firm* — Nixon Peabody LLP; Ronald I. Eisenstein; Teresa A. Ptashka

(57) ABSTRACT

Embodiments disclosed herein provide artificial expression systems comprising the zinc-finger containing transcription factors and engineered promoters to modulate expression of genes of interest. Engineered zinc-finger transcription factors that interact with engineered promoters constitute synthetic and regulatable expression systems which facilitate the modulation of gene expression as desired.

18 Claims, 19 Drawing Sheets

Specification includes a Sequence Listing.

Components of an engineered zinc finger-containing synthetic transcription factor (synTF) (Formula I)

Components of a DNA-binding zinc finger protein domain (Formula IV)

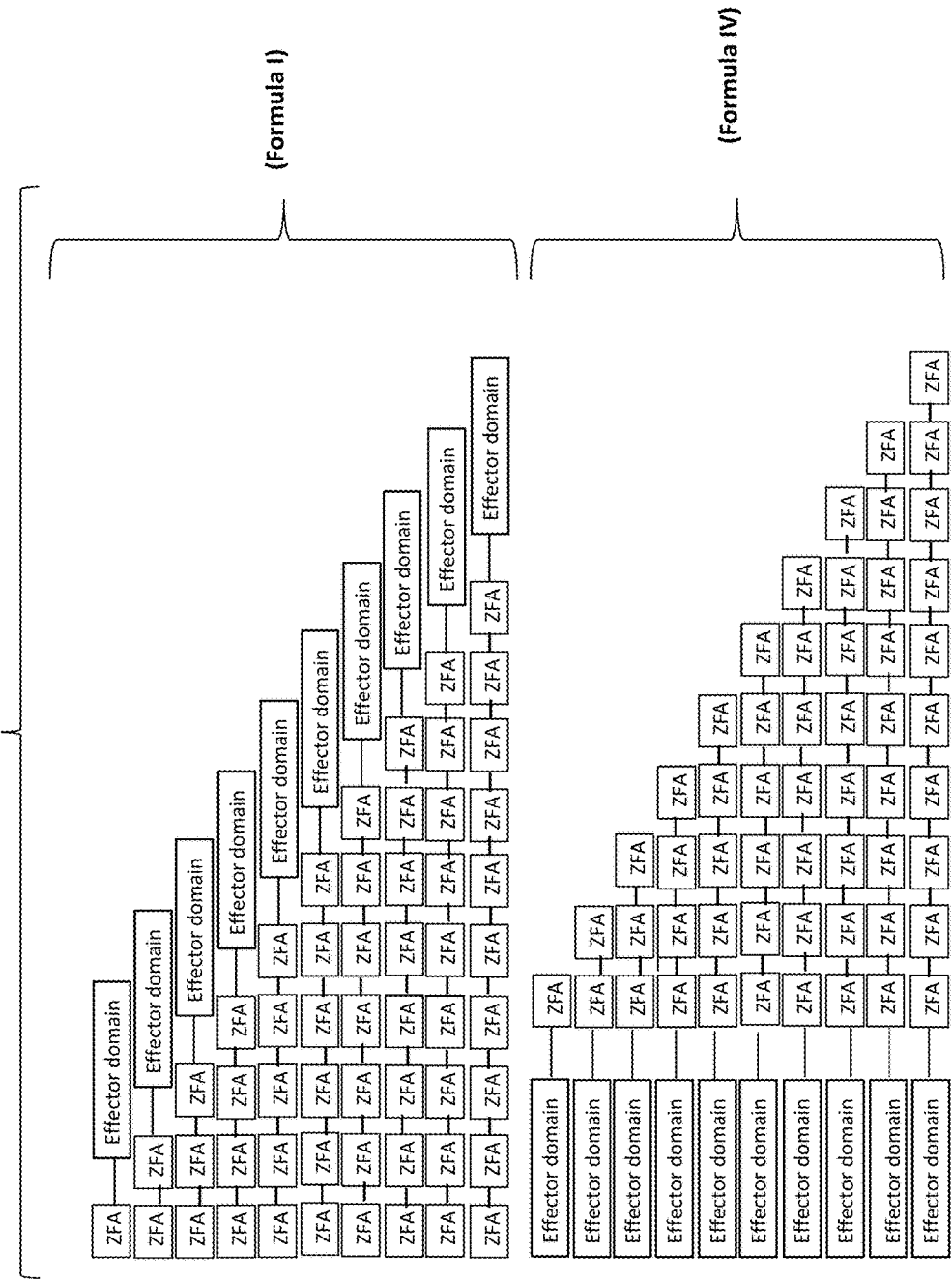
FIG.3 Architecture of an engineered zinc finger-containing synthetic transcription factor (synTF)

FIG. 4A

1X Target Site

5' GTCGAC GTATCAGTGCGCCTCGGAA [Target]
ATTCGTAAGAGGCTCACTCTCCCTTACACGGAGTGGATA ACTAGT
*TAGG CGTGTACGGTGGGAGGCCTATATAAGCAGAGCTCGTTTAGTG*
*AACCGTCAGATCGCCTGGA* ACGCGT *ACCGGTGTC* gccacc [GFP]
3'

4X Target Sites

5' GTCGAC
CGGGTTTCGTAACAATCGCATGAGGATTCGCAACGCCTT [Target]
TCCGTCTCAGTAAAGGT [Target] AATCGGACTGCCTTCGTA
GTATCAGTCGCCTCGGAA [Target]
ATTCGTAAGAGGCTCACTCTCCCTTACACGGAGTGGATA ACTAGT
*TAGGCGTGTACGGTGGGAGGCCTATATAAGCAGAGCTCGTTTAGTG*
*AACCGTCAGATCGCCTGGA* ACGCGT *ACCGGTGTC* gccacc [GFP]
3'

Bold=Restriction sites; Regular = spacer sequences; italics = Minimal CMV Promoter; lower case = Kozak sequence

FIG. 4B

8X Target Sites

5' GTCGAC GAA[Target] CCTTTCCACGATCATGTGC [Target]
AGTAATACCACCACTGCGACCCTAGATCGGAGATCCAATTAGATCCA TGATCCGAAAC [Target]
GTGTCGCAGTATCACTTGATCGGCAAA [Target] TTGCTTCCTC [Target] GAGGTAGATCAGGCCA [Target]
TTGGCGTGCCTAGATCATCGTTGGC [Target] ACAGATCGAGATCTTTGGT [Target]
TCCATAGTGAGTTCTGATCGTGTCAGGCTAGCCAGTCGATGTCGCGTA GGATCGAGGATCATCTCTGATCTGTTTAGG
ACTAGT GCATGC GC *GTTGACATTGATTATTGACTAGTTATTAATAGTAATCAATTACGGGGT
CATTAGTTCATAGCCCATATATGGAGTTCCGCGTTACATAACTTACG
GTAAATGGCCCGCCTGGCTGACCGCCCAAGACCCCGCCCATTGA
CGTCAATAATGACGTATGTTCCCATAGTAACGCCAATAGGGACTTTC
CATTGACGTCAATGGGTGGAGTATTTACGGTAAACTGCCCACTTGGC
AGTACATCAAGTGTATCATATGCCAAGTACGCCCCCTATTGACGTCA
ATGACGGTAAATGGCCCGCCTGGCATTATGCCCAGTACATGACCTTA
TGGGACTTTCCTACTTGGCAGTACATCTACGTATTAGTCATCGCTATT
ACCATGGTGATGCGGTTTTGGCAGTACATCAATGGGCGTGGATAGC
GGTTTGACTCAC GGGGATTTC CAAGTCTCCACCCCATTGACGTCAAT
GGGAGTTTGTTTTGGCACCAAAATCAACGGGACTTTCCAAAATGTCG
TAACAACTCCGCCCATTGACGCAAATGGGCGGTAGGCGTGTACGG
TGGGAGGTCTATATAAGCA GAGCTC TCTGGCTAACTAGAGAACCACTGCTTACTGGCTTATCGAAATTAATA
CGACTCACTATAGGGAGACCCAAGCTG ACGGGT ACCGGT GTC* gccacc Bold=Restriction Site; regular= Spacer; italics= Minimal CMV Promoter; lower case = Kozak

FIG. 4C

5X Target Sites

5' GTCGAC
CGGGTTTCGTAACAATCGCATGAGGATTCGCAACGCCTT
[Target] GACTGTTGCGAACGATTC [Target]
TCCCGTCTCAGTAAAGGT [Target] AATCGGACTGCCTTCGTA
[Target] GTATCAGTCGCCTCGGAA [Target]
ATTCGTAAGAGGCTCACTCTCCCTTACACGGAGTGGATA
ACTAGT
*TAGGCGTGTACGGGTGGGGAGGCCTATATAAGCAGAGCTCGTTT*
*AGTGAACCGTCAGATCGCCTGGA* ACGCGT *ACCGGTGTC* gccacc [GFP] 3'

Bold=Restriction Site; Regular=Spacer, italics= Minimal CMV Promoter; lower case= Kozak

FIG. 5A

N' SR PGERP
FQCRICMRNFS [Variable Helix 1] HTRTH TGEKP
FQCRICMRNFS [Variable Helix 2] HLRTH TGSQKP
FQCRICMRNFS [Variable Helix 3] HLRTH TGEKP
FQCRICMRNFS [Variable Helix 4] HLKTH TGSQKP
FQCRICMRNFS [Variable Helix 5] HLRTH TGEKP
FQCRICMRNFS [Variable Helix 6] HLRTH LR GS C'
[XXCXXCXXXXX-(Variable helix)-HXXXH]-linker peptide (flexible or rigid linker)

FIG. 5B

N' SR PGERP
FQCRICMRNFS [Variable Helix 1] HTRTH TGEKP
FQCRICMRNFS [Variable Helix 2] HLRTH TGSQKP
FQCRICMRNFS [Variable Helix 3] HLRTH TGEKP
FQCRICMRNFS [Variable Helix 4] HLRTH TGSQK P
FQCRICMRNFS [Variable Helix 5] HLRTH TGEKP
FQCRICNCNFS [Variable Helix 6] HLRTH LR GS C'

Bold=Restriction Site; FQC & RNF=Beta Strand; HTRTH or HLKTH =Fixed Helix Segment; TGEKP =Rigid ZF-ZF Linker; TGSQKP =Flexible ZF-ZF Linker

FIG. 6A

N' MFE PKKKRKV FEGTAS
SR PGERP
FQCRICMRNFS [Variable Helix 1] HTRTH TGEKP
FQCRICMRNFS [Variable Helix 2] HLRTH TGSQKP
FQCRICMRNFS [Variable Helix 3] HLRTH TGEKP
FQCRICMRNFS [Variable Helix 4] HLKTH TGSQKP
FQCRICMRNFS [Variable Helix 5] HLRTH TGEKP
FQCRICMRNFS [Variable Helix 6] HLRTH LR GS
TCR *GRADALDDFDLDMLGSDALDDFDLDMLGSDALDDFDLDMLGSDALD
DFDLDML* C'

SEQ ID NO: 127

PKKKRKV =Nuclear Localization Sequence; FEGTAS and TCR =Linker bold=Restriction Site; FQC & RNF= Beta Strand; HTRTH or HLKTH = Fixed Helix Segment; TGEKP =Rigid ZF-ZF Linker; TGSQKP =Flexible ZF-ZF Linker; italics= VP64 Activation Domain

FIG. 6B

N'
MDAKSLTAWSRTLVTFKDVFVDFTREEWKLLDTAQQILYRNVMLENY
KNLVSLGYQLTKPDVILRLEKGEEPWLVEREIHQETHPDSETAFEIKSSV PKKKRKV
LEGGGGSGTCR
SR PGERP
FQCRICMRNFS [Variable Helix 1] HTRTH TGEKP
FQCRICMRNFS [Variable Helix 2] HLRTH TGSQKP
FQCRICMRNFS [Variable Helix 3] HLRTH TGEKP
FQCRICMRNFS [Variable Helix 4] HLKTH TGSQKP
FQCRICMRNFS [Variable Helix 5] HLRTH TGEKP
FQCRICMRNFS [Variable Helix 6] HLRTH LR GS C'

SEQ ID NO: 128

Italics=KRAB Represssive Domain; PKKKRKV =Nuclear Localization Sequence; LEGGGGSGTCR =Linker; bold= Restriction Site; FQC & RNF= Beta Strand; HTRTH or HLKTH = Fixed Helix Segment; TGEKP= Rigid ZF-ZF Linker; TGSQKP = Flexible ZF-ZF Linker

FIG. 6C

N'
MKKREQSNDIARGFERGLEPEKIIGATDSCGDLMFLMKWKDTDEADL
VLAKEANVKCPQIVIAFYEERLTWHAYPEDAENKEK
AS PKKKRKV LEGGGGSGTCR
SR PGERP
FQCRICMRNFS [Variable Helix 1] HTRTH TGEKP
FQCRICMRNFS [Variable Helix 2] HLRTH TGSQKP
FQCRICMRNFS [Variable Helix 3] HLRTH TGEKP
FQCRICMRNFS [Variable Helix 4] HLKTH TGSQKP
FQCRICMRNFS [Variable Helix 5] HLRTH TGEKP
FQCRICMRNFS [Variable Helix 6] HLRTH LR GS C'

Italics=HP1 Chromo Shadow Domain; PKKKRKV =Nuclear Localization Sequence; LEGGGGSGTCR and AS = Linker; bold= Restriction Site; FQC & RNF= Beta Strand; HTRTH or HLKTH = Fixed Helix Segment; TGEKP= Rigid ZF-ZF Linker; TGSQKP = Flexible ZF-ZF Linker

FIG. 6D

N' MFE PKKKRKV FEGTAS
SR PGERP
FQCRICMRNFS [Variable Helix 1] HTRTH TGEKP
FQCRICMRNFS [Variable Helix 2] HLRTH TGSQKP
FQCRICMRNFS [Variable Helix 3] HLRTH TGEKP
FQCRICMRNFS [Variable Helix 4] HLKTH TGSQKP
FQCRICMRNFS [Variable Helix 5] HLRTH TGEKP
FQCRICMRNFS [Variable Helix 6] HLRTH LR GS
TCR
*DEFPTMVFPSGQISQASALAPAPPQVLPQAPAPAPAPAMVSALAQA
PAPVLAPGPPQAVAPPAPKPTQAGEGTLSEALLQLQFDDEDLGAL
LGNSTDPAVFTDLASVDNSEFQQLLNOGIPVAPHTTEPMLMEYPPEA1
TRLVTGAQRPPDPAPAPLGAPGLPNGLLSGDEDFSSIADMDFSALLS
QJSS* C'

PKKKRKV =Nuclear Localization Sequence; FEGTAS and TCR = Linker; bold= Restriction Site; FQC & RNF= Beta Strand; HTRTH or HLKTH = Fixed Helix Segment; TGEKP= Rigid ZF-ZF Linker; TGSQKP = Flexible ZF-ZF Linker; italics=p65 Activation Domain (Aas 361-551)

US 10,138,493 B2

SYNTHETIC TRANSCRIPTIONAL AND EPIGENETIC REGULATORS BASED ON ENGINEERED, ORTHOGONAL ZINC FINGER PROTEINS

CROSS REFERENCE TO RELATED APPLICATIONS

This U.S. utility application claims the benefit under 35 U.S.C. § 119(e) of U.S. Provisional Application No. 62/379,490 filed on Aug. 25, 2016, and of U.S. Provisional Application No. 62/450,459 filed on Jan. 25, 2017; the contents of each of which are incorporated herein by reference in their entireties.

GOVERNMENT SUPPORT

This invention was made with Government Support under Contract No. W911NF-11-2-0056 awarded by the Defense Advanced Research Projects Agency (DRAPA), the Army Research Office, Department of Defense. The Government has certain rights in the disclosure.

SEQUENCE LISTING

The instant application contains a Sequence Listing which has been submitted electronically in ASCII format and is hereby incorporated by reference in its entirety. Said ASCII copy, created on Apr. 3, 2018, is named 701586-087933-US_SL.txt and is 88,064 bytes in size.

FIELD OF THE DISCLOSURE

The disclosure relates to artificial expression systems comprising the described transcription factors and promoters to modulate expression of genes of interest. Engineered transcription factors that interact with artificial engineered promoters constitute synthetic and regulatable expression systems which facilitate the modulation of gene expression as desired.

BACKGROUND

Precise regulation of therapeutic gene expression is a central approach to the treatment of many genetic disorders. Recent technologies aim to reverse dysregulated gene expression through the development and delivery of synthetic regulatory systems, for example, using engineered proteins that target responsive promoters to conditionally induce or silence therapeutic gene expression. These protein-DNA interaction systems are encoded in nucleic acid constructs and delivered to cells through traditional cell delivery methods, for examples, lentiviral, retroviral, and adenoviral vectors. It has importantly been demonstrated that first-generation therapeutic delivery systems are functional and clinically viable strategies capable of achieving long-term regulation in primates. Non-limiting examples of some first-generation therapeutic delivery systems include simple, zinc finger containing transcription factors to induce therapeutic gene expression.

However, there are fundamental limitations to certain families of synthetic regulatory proteins that prevent their widespread adoption in gene therapies. For example, certain classes of programmable DNA-targeting domains (Transcription Activator Like Effector (TALE) and CRISPR/dCas9) are derived from prokaryotic systems, rendering them likely to be immunogenic in a human therapy context. Additionally, these proteins are large and approach the packaging limits of traditional lentiviral delivery schemes, preventing ease of delivery and addition of other useful molecular components.

SUMMARY

Embodiments described herein are based on a novel engineered zinc finger-containing protein domain that is designed to bind to orthologus DNA target sequences, and has little or no binding to existing DNA sequences in organisms. The engineered zinc finger-containing protein domain, referred herein as the ZF protein domain, can be fused to an effector domain, an epigenetic effector domain, a ligand binding domain, or a protein interaction/dimerization domain.

The effector domain can be an activator domain or a repressor domain, activating or repressing the expression of a gene respectively. The effector domain brings about an effect on the DNA sequence that is placed is close proximity to the domain. Within a fusion protein containing the engineered zinc finger-containing protein domain, the ZF protein domain in the fusion protein can direct the fused effector domain or an epigenetic effector domain to an orthologus DNA target sequence in the promoter region of a gene such that the expression of that gene can be upregulated or downregulated by the effector domain or an epigenetic effector domain.

The ligand binding domain is the ligand binding domain of a receptor, e.g., a steroid hormone receptor (e.g., estrogen receptor). An example of a ligand binding domain is an estrogen receptor ligand binding domain, ERT2. Examples of ligands that would bind an estrogen receptor ligand binding domain are tamoxifen and other estrogen analogs. When the engineered zinc finger-containing protein domain is fused to a ligand binding domain, the ligand binding domain, upon binding to its respective ligand, can direct the fusion protein to translocate to the nucleus.

When the ZF protein domain is fused to a dimerization domain, upon dimerization with its respective counterpart dimerization domain, the dimerization domain can direct the fusion protein to close vicinity of another protein domain that is fused to the respective counterpart dimerization domain. An example of such a dimerization domain and its respective counterpart dimerization domain is the dimerization system based of the ABI1/PYL1 plant abscisic acid system. The ZF protein domain can be fused to ABI1, forming the first fusion protein. In a second fusion protein, an activation domain, VP64, is fused to PYL1. Mixing the first and second fusion proteins allows the interaction of ABI1 with PYL1 via dimerization in the presence of ABA (abscisic acid), thereby bringing the ZF protein domain in the first fusion protein in close proximity with the VP64 activation domain in the second fusion protein.

Accordingly, in one aspect, provided herein is a class of engineered transcription factor proteins (synTFs) and corresponding responsive artificial engineered promoters capable of precisely controlling gene expression in a wide range of eukaryotic cells and organisms, including mammalian cells. These synTFs are specifically designed to have reduced or minimal binding potential in the host genome (i.e., "orthogonal" activity to the host genome). The synTF proteins described herein are based on engineered zinc finger (ZF) arrays that are designed to target and bind specific 18-20 nucleotide sequences that are distant and different from the host genome sequences, when the synTF proteins are used in the selected hosts. This strategy limits non-specific interations of the synTF proteins with the host's genome; such non-specific interations are not ideal and therefore, are not desired.

The synTFs described herein are designed, in some aspects, according to the following parameters: (1) targetable DNA sequences (also known as ZF binding sites) are identified for the ZF arrays that are specifically designed to have reduced binding potential in a host genome; (2) ZF arrays are designed and assembled; (3) synTFs are designed by coupling engineered (i.e., covalently linked) ZF arrays to transcriptional and/or epigenetic effector domains; (4) corresponding responsive promoters are designed by placing instances of the targetable DNA sequences (i.e., ZF binding sites) upstream of constitutive promoters. The targetable DNA sequences are operably linked to the promoters such that the occupancy of synTFs on the targetable DNA sequences regulates the activity of the promoter in gene expression. The combination of a synTFs and a targetable DNA sequence-promoter forms a unique expression system that is artificial, scalable, and regulatable, for the expressions of desired genes placed within the expression systems, with no or minimal effects on the expression of endogenous genes, meaning no or minimal off-site gene regulation of endogenous genes.

The synTFs described herein have reduced or minimal functional binding potential in the host genome, which provides, in part, advantages of no or minimal off-site DNA targeting by the synTFs. In addition, the synthetic ZF-based proteins (synTFs) described herein are derived from mammalian protein scaffolds, conferring minimal degree of immunogenicity over other prokaryotically-derived domains. In contrast to other classes of programmable DNA-targeting domains, these zinc-finger-based regulatory proteins are considerably smaller (~4-5x) than TALE and dCas9 proteins, less repetitive than TALE repeat proteins, and are not as constrained by lentiviral packaging limits, enabling convenient packaging in lentiviral delivery constructs and affording space for other desirable control elements.

In another aspect, provided herein are engineered transcription factor proteins (synTFs) described herein that are further fused to a ligand binding domain or a dimerization domain (also known as an interaction domain).

In one embodiment, the ligand binding domain is a steroid receptor ligand binding domain such as estrogen receptor. In one embodiment, the ligand is tamoxifen or other estrogen analogs. In one embodiment, provided is a fusion protein having this configuration: synTF-[ligand binding domain] or [ligand binding domain]-synTF. The conjugation of the synTF to a ligand binding domain would facilitate nuclear translocation of the synTF in the presence of the ligand.

In one embodiment, the protein interaction/dimerization domain is the dimerization domain of ABI1, PYL1, FKBP (FK506 binding protein) or Frb (FKBP-Fap binding domain of mTOR). The protein interaction/dimerization domains of ABI1 and PYL1 dimerized upon the presence of ABA (Abscisic acid), and FKBP and Frb dimerized upon the presence of rapamycin.

In another aspect, provided herein is a class of engineered zinc finger-containing fusion proteins, each fusion protein comprising (1) a ZF protein domain is described herein that comprises an engineered zinc finger (ZF) arrays; and (2) a ligand binding domain or a protein interaction/dimerization domain, wherein the engineered ZF arrays are coupled to the ligand binding domain or the protein interaction/dimerization domain. The engineered ZF arrays forms the ZF-containing protein domain of the fusion protein and comprises all the features and variations described herein for a ZF protein domain for the synTFs in this application. The ZF-containing protein domain can be located at the N-terminus or the C-terminus of the described fusion protein containing a ligand binding domain or a protein interaction/dimerization domain. The design of the engineered zinc finger-containing fusion proteins are as follows: [ZF protein domain]-[ligand binding domain]; [ZF protein domain]-[protein interaction/dimerization domain]; [ligand binding domain]-[ZF protein domain]; and [protein interaction/dimerization domain]-[ZF protein domain].

Definitions

As used herein, the term "comprising" or "comprises" means that other elements can also be present in addition to the defined elements presented. The use of "comprising" indicates inclusion rather than limitation.

As used herein, the term "consisting of" or "consists of" refers to methods, and respective components thereof as described herein, which are exclusive of any element not recited in that description of the embodiment.

As used herein, the term "consisting essentially of" or "consists essentially of" refers to those elements required for a given embodiment. The term permits the presence of elements that do not materially affect the basic and novel or functional characteristic(s) of that embodiment of the disclosure.

As used herein, the term "orthogonal DNA sequence elements" refers to those DNA sequences that are not found or are rarely represented in the eukaryotic genome in nature.

As used herein, the term "orthogonus" when use in context with nucleic acid sequences such as DNA refers to not naturally found in nature.

As used herein, the terms "linked", "connected", "covalently conjugated" and "coupled" are used interchangeably and they are used to indicated that two separate domains or motifs described herein are made are joined together into a single macromolecule.

As used herein, the term "linker" or a "cross-linker" refers to a molecule entity that is used to connect two or more domains or portions of a polypeptide as described herein. In some embodiments of any one aspects described herein, the linker connects a first ZF with a second ZF. In some embodiments of any one aspects described herein, the linkers connect several ZFs to each other in tandem to form a ZF array. In some embodiments of any one aspects described herein, the linker connects a first ZFA with a second ZFA. In some embodiments of any one aspects described herein, the linkers connect several ZFAs to each other to in tandem to form a ZF-containing ZF protein domain. A linker or "linker" may be may be a peptide, which consist of one to multiple amino acids. Non-limiting examples of peptide linker molecules useful in the polypeptides described herein include glycine-rich peptide linkers (see, e.g., U.S. Pat. No. 5,908,626), wherein more than half of the amino acid residues are glycine. Preferably, such glycine-rich peptide linkers consist of about 20 or fewer amino acids. A linker molecule may also include non-peptide or partial peptide molecules. For instance, the peptides can be linked to peptides or other molecules using well known cross-linking molecules such as glutaraldehyde or EDC (Pierce, Rockford, Ill.).

In some embodiments of the engineered synTFs described herein, the ZF protein domains and effector domains are joined together in the respective fusion protein with a linker peptide.

In some embodiments of the engineered synTFs described herein, the ZF arrays (ZFAs) in the ZF protein domain of the synTF are joined together in the respective fusion protein with a linker peptide. Examples of linker peptide include, but are not limited to: PGER (SEQ ID NO: 4), TGSQK (SEQ ID NO: 5), TGEKP (SEQ ID NO: 2), THLR (SEQ ID NO: 6), TGGGEKP (SEQ ID NO: 1), FHYDRNNIAV-GADESVVKEAHREVINSSTEGLLLNIDKDIRKILS-GYIVEIEDTE (SEQ ID NO: 7); VEIEDTE (SEQ ID NO: 8), KDIRKILSGYIVEIEDTE (SEQ ID NO: 9); STEGLLL-NIDKDIRKILSGYIVEIEDTE (SEQ ID NO: 10), EVKQENRLLNESES (SEQ ID NO: 11); and VGADESV-VKEAHREVINSSTEGLLLNIDKDIRKILSGYIVEIEDTE (SEQ ID NO: 12). For examples, TGSQK (SEQ ID NO: 5) or TGEKP (SEQ ID NO: 2) or TGGGEKP (SEQ ID NO: 1) is used as linker between ZFAs; VEIEDTE (SEQ ID NO: 8) or GGSGGS (SEQ ID NO: 13) are used to link ZF domains and effector domains together.

Flexible linkers are generally composed of small, non-polar or polar residues such as Gly, Ser and Thr. In one embodiment of any fusion protein described herein that includes a linker, the linker peptide comprises at least one amino acid that is Gly or Ser. In one embodiment of a fusion protein described herein that includes a linker, the linker is a flexible polypeptide between 1 and 25 residues in length. Common examples of flexible peptide linkers include (GGS)n, where n==1 to 8 (SEQ ID NO: 14), or (Gly$_4$Ser)n repeat where n=1-8 (SEQ ID NO: 15), preferably, n=3, 4, 5, or 6, that is (Gly-Gly-Gly-Gly-Ser)n (SEQ ID NO: 16), where n indicates the number of repeats of the motif. For example, the flexible linker is (GGS)2 (SEQ ID NO: 17), GGSGGS (SEQ ID NO: 13). Alternatively, flexible peptide linkers include Gly-Ser repeats (Gly-Ser)$_p$ where p indicates the number of Gly-Ser repeats of the motif, p=1-8 (SEQ ID NOS: 134-141), preferably, n=3, 4, 5, or 6. Another example of a flexible linker is TGSQK (SEQ ID NO: 5).

In one embodiment of the engineered synTFs described herein, wherein the ZF protein domains and effector domains are joined together with a linker peptide, the linker peptide is about 1-20 amino acids long. In one embodiment, the linker peptide does not comprise Lys, or does not comprise, or does not comprise both Lys and Arg.

In some embodiments of the engineered synTFs described herein, the ZF protein domains and effector domains are joined together chemical cross-linking agents. Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. General methods for cross-linking molecules have been reviewed (see, e.g., Means and Feeney, Bioconjugate Chem., 1: 2-12 (1990)).

Homobifunctional cross-linker molecules have two reactive sites which are chemically the same. Non-limiting examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., discuccinimyidyl suberate, dithiobis (succinimidyl propionate), and soluble bis-sulfonic acid and salt thereof (see, e.g., Pierce Chemicals, Rockford, Ill.; Sigma-Aldrich Corp., St. Louis, Mo.).

A bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the disclosure include, without limitation, m-maleimidobenzoyl-N-hydroxysuccinimide ester (see, Green et al., Cell, 28: 477-487 (1982); Palker et al., Proc. Natl. Acad. Sci (USA), 84: 2479-2483 (1987)): m-maleimido-benzoylsulfosuccinimide ester; maleimidobutyric acid N-hydroxysuccinimide ester; and N-succinimidyl 3-(2-pyridyl-dithio)propionate (see, e.g., Carlos et al., Biochem. J., 173: 723-737 (1978); Sigma-Aldrich Corp., St. Louis, Mo.).

The term "amino acid" in the context of the present disclosure is used in its broadest sense and is meant to include naturally occurring L α-amino acids or residues. The commonly used one and three letter abbreviations for naturally occurring amino acids are used herein: A=Ala: C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

The term "peptide" as used herein (e.g. in the context of a zinc finger containing synTF or framework) refers to a plurality of amino acids joined together in a linear or circular chain. The term oligopeptide is typically used to describe peptides having between 2 and about 50 or more amino acids. Peptides larger than about 50 amino acids are often referred to as polypeptides or proteins. For purposes of the present disclosure, however, the term "peptide" is not limited to any particular number of amino acids, and is used interchangeably with the terms "polypeptide" and "protein".

A zinc finger (ZF) is a finger-shaped fold in a protein that permits it to interact with nucleic acid sequences such as DNA and RNA. Such a fold is well known in the art. The fold is created by the binding of specific amino acids in the protein to a zinc atom. Zinc-finger containing proteins (also known as ZF proteins) can regulate the expression of genes as well as nucleic acid recognition, reverse transcription and virus assembly.

A ZF is a relatively small polypeptide domain comprising approximately 30 amino acids, which folds to form an α-helix adjacent an antiparallel β-sheet (known as a ββα-fold). The fold is stabilised by the co-ordination of a zinc ion between four largely invariant (depending on zinc finger framework type) Cys and/or His residues, as described further below. Natural zinc finger domains have been well studied and described in the literature, see for example, Miller et al., (1985) EMBO J. 4: 1609-1614; Berg (1988) Proc. Natl. Acad. Sci. USA 85: 99-102; and Lee et al., (1989) Science 245: 635-637. A ZF domain recognises and binds to a nucleic acid triplet, or an overlapping quadruplet (as explained below), in a double-stranded DNA target sequence. However, ZFs are also known to bind RNA and proteins (Clemens, K. R. et al. (1993) Science 260: 530-533; Bogenhagen, D. F. (1993) Mol. Cell. Biol. 13: 5149-5158; Searles, M. A. et al. (2000) J. Mol. Biol. 301: 47-60; Mackay, J. P. & Crossley, M. (1998) Trends Biochem. Sci. 23: 1-4).

In one embodiment, as used herein, the term "zinc finger" (ZF) or "zinc finger motif" (ZF motif) or "zinc finger domain" (ZF domain) refers to an individual "finger", which comprises a beta-beta-alpha (ββα)-protein fold stabilised by a zinc ion as described elsewhere herein. The Zn-coordinated ββα protein fold produces a finger-like protrusion, a "finger." Each ZF motif typically includes approximately 30 amino acids. The term "motif" as used herein refers to a structural motif. The ZF motif is a supersecondary structure having the ββα-fold that stabilised by a zinc ion.

In one embodiment, the term "ZF motif" according to its ordinary usage in the art, refers to a discrete continuous part of the amino acid sequence of a polypeptide that can be equated with a particular function. ZFmotifs are largely structurally independent and may retain their structure and function in different environments. Because the ZF motifs are structurally and functionally independent, the motifs also qualify as domains, thus are often referred as ZF domains. Therefore, ZF domains are protein motifs that contain multiple finger-like protrusions that make tandem contacts with their target molecule. Typically, a ZF domain binds a triplet or (overlapping) quadruplet nucleotide sequence. Adjacent ZF domains arranged in tandem are joined together by linker sequences to form an array. A ZF peptide typically contains a ZF array and is composed of a plurality of "ZF domains", which in combination do not exist in nature. Therefore, they are considered to be artificial or synthetic ZF peptides or proteins.

$C_2H_2$ zinc fingers ($C_2H_2$-ZFs) are the most prevalent type of vertebrate DNA-binding domain, and typically appear in tandem arrays (ZFAs), with sequential $C_2H_2$-ZFs each contacting three (or more) sequential bases. $C_2H_2$-ZFs can be assembled in a modular fashion. Given a set of modules with defined three-base specificities, modular assembly also presents a way to construct artificial proteins with specific DNA-binding preferences.

ZF-containing proteins generally contain strings or chains of ZF motifs, forming an array of ZF (ZFA). Thus, a natural ZF protein may include 2 or more ZF, ie. a ZFA consisting of 2 or more ZF motifs, which may be directly adjacent one another (i.e. separated by a short (canonical) linker sequence), or may be separated by longer, flexible or structured polypeptide sequences. Directly adjacent ZF domains are expected to bind to contiguous nucleic acid sequences, i.e. to adjacent trinucleotides/triplets. In some cases crossbinding may also occur between adjacent ZF and their respective target triplets, which helps to strengthen or enhance the recognition of the target sequence, and leads to the binding of overlapping quadruplet sequences (Isalan et al., (1997) Proc. Natl. Acad. Sci. USA, 94: 5617-5621) By comparison, distant ZF domains within the same protein may recognise (or bind to) non-contiguous nucleic acid sequences or even to different molecules (e.g. protein rather than nucleic acid).

Engineered ZF-containing proteins are chimeric proteins composed of a DNA-binding zinc finger protein domain (ZF protein domain) and another domain through which the protein exerts its effect (effector domain). The effector domain may be a transcriptional activator or repressor, a methylation domain or a nuclease. DNA-binding ZF protein domain would contain engineered zinc finger arrays (ZFAs).

Engineered ZF-containing proteins are non-natural and suitably contain 3 or more, for example, 4, 5, 6, 8, 9, 10, 11, 12, 13, 14, 15, 16, 17, 18 or more (e.g. up to approximately 30 or 32) ZF motifs arranged adjacent one another in tandem, forming arrays of ZF motifs or ZFA. Particularly ZF-containing synTF proteins (ZF-containing synTF fusion protein, or simply synTF) of the disclosure include at least 3 ZF, at least 4 ZF motifs, at least 5 ZF motifs, or at least 6 ZF motifs, at least 7 ZF motifs, at least 8 ZF motifs, at least 9 ZF motifs, at least 10 ZF motifs, at least 11 or at least 12 ZF motifs; and in some cases at least 18 ZF motifs. In other embodiments, the ZF synTF contains up to 6, 7, 8, 10, 11, 12, 16, 17, 18, 22, 23, 24, 28, 29, 30, 34, 35, 36, 40, 41, 42, 46, 47, 48, 54, 55, 56, 58, 59, or 60 ZF motifs. The ZF-containing synTF of the disclosure bind to contiguous orthogonal target nucleic acid binding sites. That is, the ZFs or ZFAs comprising in the ZF domain of the fusion protein binds orthogonal target nucleic acid sequences.

In one embodiment, as used herein, an "engineered synthetic transcription factor" or "engineered synTF" or "synTF" refers to an engineered ZF-containing chimeric protein having at least one of the following characteristics and may have more than one: bind target orthogonal specific DNA sequences and have, for example, reduced or minimal functional binding potential in a host eukaryotic genome; are derived from mammalian protein scaffolds, conferring minimal degree of immunogenicity over other prokaryotically-derived domains; and can be packaging in viral delivery systems, such as lentiviral delivery constructs.

In another embodiment, as used herein, the term "engineered synthetic transcription factor" or "engineered synTF," abbreviated as "synTF" or "ZF synTF," refers to an engineered ZF containing synthetic transcription factor that is a polypeptide, in other words, a ZF-containing synthetic transcription factor protein. These synTFs contain ZF arrays (ZFA) therein for binding to specific target nucleic acid sequences. The synTF is a chimeric, fusion protein that comprises a DNA-binding, ZF-containing protein domain and an effector domain through which the synTF exerts its effect on gene expression. These synTFs can modulate gene expression, wherein the modulation is by increasing or decreasing the expression of a gene that is operably linked to a promoter that is also operably linked to the specific target nucleic acid sequence to which the DNA-binding, ZF-containing protein domain of the synTF binds.

As used herein, the term "ZF array," abbreviated as "ZFA" refers to an array, or a string, or a chain of ZF motifs arranged in tandem. A ZFA can have six ZF motifs (a 6-finger ZFA), seven ZF motifs (a 7-finger ZFA), or eight ZF motifs (an 8-finger ZFA). See FIG. 2B.

As used herein, the term "engineered responsive/response promoter," "engineered promoter," or "engineered responsive/response promoter element" refers is a nucleic acid construct containing a promoter sequence that has at least one orthogonal DNA target sequence operably linked upstream of the promoter sequence such that the orthogonal DNA target sequence confer a responsive property to the promoter when the orthogonal DNA target sequence is bound by its respective transcription factor, the responsive property being whether gene transcription initiation from that promoter is enhanced or repressed when the upstream nearby orthogonal DNA target sequences are bound by a ZF-containing synthetic transcription factor. There may be more than one orthogonal DNA target sequence operably linked upstream of the promoter sequence. When there is one orthogonal DNA target sequence, the promoter is referred to a "1×" promoter, where the "1×" refers to the number of orthogonal DNA target sequence present in the promoter construct. For example, a 4× responsive promoter would be identified as having four orthogonal DNA target sequences in the engineered response protomer construct, and the four orthogonal DNA target sequences are upstream of the promoter sequence.

As used herein, the term "engineered responsive reporter" or "engineered transcription unit" is a nucleic acid construct containing an engineered promoter that is operably linked to a reporter gene, and the expression of the reporter gene is controlled by upstream regulatory elements such orthogonal DNA target sequence(s) in the engineered promoter. A reporter gene is typically one where the gene product, the transcribed protein, is easily detected and monitored, e.g., the green fluorescent protein.

As used herein, the term "promoter" as used in the art, is a region of DNA that initiates transcription of a particular gene and is at which RNA polymerase binds and initiates transcription. Promoters are located near the transcription start sites of genes, on the same strand and upstream on the DNA As used herein, the term "orthogonal" when used in DNA sequences and genome biology "orthogonal" means DNA sequences that are so dissimilar from that which is naturally occurring in nature in the eukaryotic system.

As used herein, the term "responsive" in the context of an engineered promoter or engineered transcription unit or engineered responsive reporter, the term refers to whether whether gene transcription initiation from the promoter is enhanced or repressed when upstream nearby orthogonal DNA target sequences are bound by their respective ZF-containing synthetic transcription factors.

As used herein, the term "operably linked" when used in context of the orthogonal DNA target sequences described herein or the promoter sequence (RNA polymerase binding site) in a nucleic acid construct, an engineered responsive reporter, and in an engineered transcription unit means that the orthogonal DNA target sequences and the promoters are in-frame and in proper spatial and distance away from a nucleic acid coding for a protein or peptide or an RNA to permit the effects of the respective binding by transcription factors or RNA polymerase on transcription.

The terms "nucleic acid", "polynucleotide", and "oligonucleotide" are used interchangeably and refer to a deoxyribonucleotide (DNA) or ribonucleotide (RNA) polymer, in linear or circular conformation, and in either single- or double-stranded form. For the purposes of the present disclosure such DNA or RNA polymers may include natural nucleotides, non-natural or synthetic nucleotides, and mixtures thereof. Non-natural nucleotides may include analogues of natural nucleotides, as well as nucleotides that are modified in the base, sugar and/or phosphate moieties (e.g. phosphorothioate backbones). Non-limiting examples of modified nucleic acids are PNAs and morpholino nucleic acids. Generally an analogue of a particular nucleotide has the same base-pairing specificity, i.e. an analogue of G will base-pair with C. For the purposes of the disclosure, these terms are not to be considered limiting with respect to the length of a polymer.

A "gene", as used herein, is the segment of nucleic acid (typically DNA) that is involved in producing a polypeptide or ribonucleic acid gene product. It includes regions preceding and following the coding region (leader and trailer) as well as intervening sequences (introns) between individual coding segments (exons). Conveniently, this term also includes the necessary control sequences for gene expression (e.g. enhancers, silencers, promoters, terminators etc.), which may be adjacent to or distant to the relevant coding sequence, as well as the coding and/or transcribed regions encoding the gene product.

As used herein the term "modulation", in relation to the expression of a gene refers to a change in the gene's activity. Modulation includes both activation (i.e. increase in activity or expression level) and repression or inhibition of gene activity. In preferred embodiments of the disclosure, the therapeutic molecules (e.g. peptides) of the disclosure are repressors of gene expression or activity.

A nucleic acid "target", "target site" or "target sequence" or "DNA target sequence", as used herein, is a nucleic acid sequence to which a ZFA in a synTF of the disclosure will bind, provided that conditions of the binding reaction are not prohibitive. A target site may be a nucleic acid molecule or a portion of a larger polynucleotide. In accordance with the disclosure, a target sequence for a ZFA in a synTF of the disclosure may comprise a single contiguous nucleic acid sequence. These terms may also be substituted or supplemented with the terms "binding site", "binding sequence", "recognition site" or recognition sequence", which are used interchangeably.

As used herein, "binding" refers to a non-covalent interaction between macromolecules (e.g. between a ZF-array containing protein and a nucleic acid target site). In some cases binding will be sequence-specific, such as between one or more specific nucleotides (or base pairs) and one or more specific amino acids. It will be appreciated, however, that not all components of a binding interaction need be sequence-specific (e.g. non-covalent interactions with phosphate residues in a DNA backbone). Binding interactions between a nucleic acid sequence and a ZF peptide of the disclosure may be characterised by binding affinity and/or dissociation constant (Kd). A suitable dissociation constant for a ZF peptide of the disclosure binding to its target site may be in the order of 1 $\mu$M or lower, 1 nM or lower, or 1 pM or lower. "Affinity" refers to the strength of binding, such that increased binding affinity correlates with a lower Kd value. ZF synTF of the disclosure may have DNA-binding activity, RNA-binding activity, and/or even protein-binding activity. In some embodiments, the ZF synTF of the disclosure are designed or selected to have sequence specific dsDNA-binding activity. For example, the target site for a particular ZF array or protein is a sequence to which the ZF concerned is capable of nucleotide-specific binding. It will be appreciated, however, that depending on the amino acid sequence of a ZF array or protein it may bind to or recognise more than one target sequence, although typically one sequence will be bound in preference to any other recognised sequences, depending on the relative specificity of the individual non-covalent interactions. Generally, specific binding is preferably achieved with a dissociation constant (Kd) of 1 nM or lower, 100 pM or lower; or 10 pM or lower. In some embodiments, a ZF synTF of the disclosure binds to a specific target sequence with a dissociation constant of 1 nM or lower, or 1 pM or lower, or 0.1 pM or lower, or even 10 fM or lower.

By "non-target" it is meant that the nucleic acid sequence concerned is not appreciably bound by the relevant ZF peptide. In some embodiments it may be considered that, where a ZF peptide described herein has a known sequence-specific target sequence, all other nucleic acid sequences may be considered to be non-target. From a practical perspective it can be convenient to define an interaction between a non-target sequence and a particular ZF peptide as being sub-physiological (i.e. not capable of creating a physiological response under physiological target sequence/ZF peptide concentrations). For example, if any binding can be measured between the ZF peptide and the non-target sequence, the dissociation constant (Kd) is typically weaker than 1 µM, such as 10 µM or weaker, 100 µM or weaker, or at least 1 mM.

As used herein, the term "interaction" when used in the context of a receptor and its ligand refers to the binding between the receptor and its ligand as a result of the non-covalent bonds between the ligand-binding site (or fragment) of the receptor and the receptor-binding site (or fragment) of the ligand. In the context of two entities, e.g., molecules or proteins, having some binding affinity for each other, the term "interaction" refers to the binding of the two entities as a result of the non-covalent bonds between the two entities. A term "interaction", "complexing" and "bonding" are used interchangeably when used in the context of a receptor and its ligand and in the context of two binding entities.

BRIEF DESCRIPTION OF THE DRAWINGS

FIG. 3 shows the architecture of engineered zinc finger-containing synthetic transcription factors (synTF) having a single zinc finger array (ZFA) or up to ten ZFAs.

FIGS. 4A-4C show the modular design of responsive promoters having one orthogonal target DNA site (1×) (SEQ ID NOS 104-105, respectively, in order of appearance), four orthogonal target DNA sites (4×) (SEQ ID NOS 106-110, respectively, in order of appearance), eight orthogonal target DNA sites (8×) (SEQ ID NOS 111-118, respectively, in order of appearance), and five orthogonal target DNA sites (5×) (SEQ ID NOS 119-124, respectively, in order of appearance) incorporated into the promoter. The individual orthogonal target DNA site is about 20 base pairs (bp) long and is indicated as [Target] described in the modular design shown.

FIG. 5A shows the modular designs of a DNA-binding zinc finger protein domain (ZF protein domain) suitable for constructing into a synTF with an effector domain (SEQ ID NOS 125 and 18, respectively, in order of appearance). Here, the ZF protein domain is composed of a single zinc finger array (ZFA) consisting of six zinc fingers (ZF) where each ZF is linked to the adjacent by a linker peptide having the sequence TGEKP (SEQ ID NO: 2) or TGSQKP (SEQ ID NO: 3). The single ZFA is a 6-finger ZFA. TGEKP (SEQ ID NO: 2) is a rigid linker peptide and TGSQKP (SEQ ID NO: 3) is a flexible linker peptide. Each ZF has the conserved ZF secondary structural motif of beta-beta-alpha helix of a CysHis zinc finger (ZF), and has the formula II of [X$_2$CX$_2$CX$_5$-(helix)-HX$_3$H] (SEQ ID NO: 18) or [XXCXX CXXXXX-(Variable helix)-HXXXH] (SEQ ID NO: 18). C=Cys, H=His, these are the Cys and His of the ZF.

FIG. 5B shows another DNA-binding zinc finger protein domain (ZF protein domain) having the modular design (SEQ ID NO: 126). Here, the ZF protein domain is composed of a single 6-finger zinc finger array (ZFA).

FIGS. 6A-6D show the modular design of engineered of ZF-containing synTFs (synTFs). Each synTF is composed of two main domain: (a) a first main domain which is a DNA-binding zinc finger protein domain (ZF protein domain), and (b) a second domain through which the synTF exerts its effect (effector domain). In each synTF, the ZF protein domain is composed of a single zinc finger array (ZFA) consisting of six zinc fingers (ZF) where each ZF is linked to the adjacent by a linker peptide having the sequence TGEKP (SEQ ID NO: 2) or TGSQKP (SEQ ID NO: 3). The effector domain shown in each synTF is either an activation or repression effector domain. The synTF is designed to have a nuclear localization domain so the protein is translocated into the nucleus of a cell.

FIG. 6A shows a synTF composed of a ZF protein domain covalently linked to a VP64 activation domain, the ZF protein domain is composed of having a single 6-finger ZFA (SEQ ID NO: 127). FIG. 6A also discloses SEQ ID NOS 149-152, respectively, in order of appearance.

FIG. 6B shows a synTF composed of a ZF protein domain covalently linked to a KRAB repressive domain, the ZF protein domain is composed of having a single 6-finger ZFA (SEQ ID NO: 128). FIG. 6B also discloses SEQ ID NOS 149, 153 and 151-152, respectively, in order of appearance.

FIG. 6C shows a synTF composed of a ZF protein domain covalently linked to a HP1 repressive domain, the ZF protein domain is composed of having a single 6-finger ZFA (SEQ ID NO: 129). FIG. 6C also discloses SEQ ID NOS 149, 153 and 151-152, respectively, in order of appearance.

FIG. 6D shows a synTF composed of a ZF protein domain covalently linked to a p65 activation domain of NFKB, the ZF protein domain is composed of having a single 6-finger ZFA (SEQ ID NO: 130). FIG. 6D also discloses SEQ ID NOS 149-152, respectively, in order of appearance.

DETAILED DESCRIPTION

Figure 1:
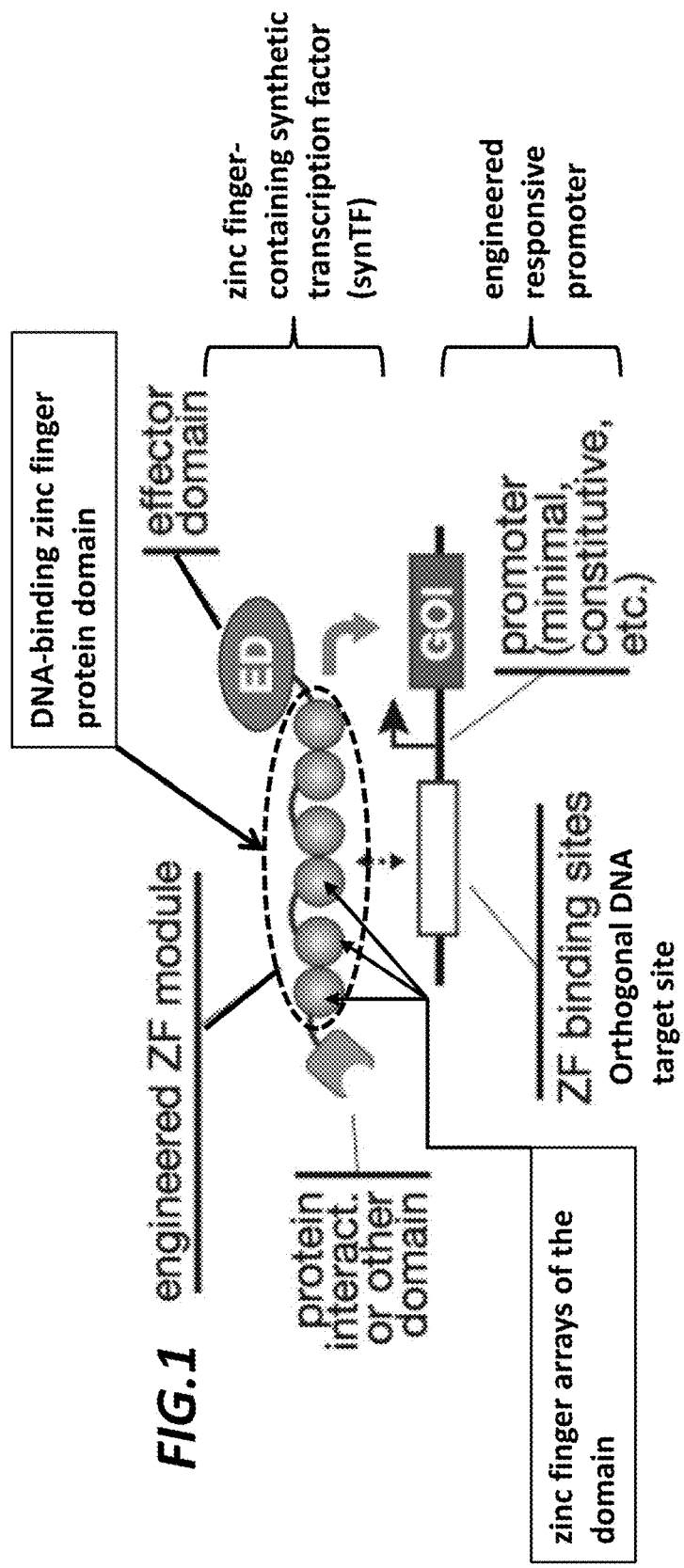
FIG. 1 show an engineered regulatable gene expression system composed of a zinc finger-containing synthetic transcription factor protein (synTF), and an engineered promoter, a nucleic acid sequence. The synTF is composed of two main domains: (a) a first main domain which is a DNA-binding zinc finger protein domain (ZF protein domain), and (b) a second domain through which the synTF exerts its effect (effector domain). The ZF protein domain is modular in design, composed zinc finger arrays (ZF arrays). The engineered protomer is composed of at least two main segment of sequences: (a) zinc finger binding target sequence (target site) and (b) a promoter sequence. The target site is specific for the particular ZF protein domain of the synTF, and constitutes the response element in the engineered regulatable gene expression system. When the target site is bound by the ZF protein domain of the respective synTF, the effector domain of that synTF would able to exert its effect on the promoter linked with the target site.

Unless otherwise explained, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Definitions of common terms in molecular biology can be found in The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Current Protocols in Molecular Biology (CPMB), Frederick M. Ausubel (ed.), John Wiley and Sons, 2014 (ISBN 047150338X, 9780471503385), and Current Protocols in Protein Science (CPPS), John E. Coligan (ed.), John Wiley and Sons, Inc., 2005, the contents of which are all incorporated by reference herein in their entireties. Further, unless otherwise required by context, singular terms shall include pluralities and plural terms shall include the singular.

Unless otherwise stated, the present disclosure was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986): Current Protocols in Molecular Biology (CPMB) (Fred M. Ausubel, et al. ed., John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, which are all herein incorporated by reference in their entireties.

It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

Disclosed herein are (1) engineered, synthetic, zinc-finger containing transcription factor proteins (synTF) that are designed to bind unique DNA sequence elements that are orthogonal to a eukaryotic genome (hereafter referred to as an "orthogonal target DNA sequence" or "orthogonal DNA sequence"). The orthogonal DNA sequence elements are also referred to as "target" DNA, "target," "target" DNA sequence or "target" DNA sequence elements in the context of the synthetic transcription factor, and are used interchangeably. These synTF are used to modulate gene expressions from promoters constructed with the orthogonal target DNA, that is, these synTF, when interacting (ie., binding) with the orthogonal target DNA, can either activate gene expression or repress gene transcription of the gene operable linked with that promoter. In essense, the promoter is responsive to the synTF. The activation or repression is executed by an effector domain that is covalently conjugated to the zinc-fingers in the synTF. (2) Engineered promoters having the orthogonal "target" DNA for the regulation of expressions of genes of interest (GOI). These are synTF responsive promoters. (3) A modulated or regulatable gene expression system comprising a synTF of (1) and an engineered promoter of (2) where there is minimal or no off-target endogenous gene modulation because of the orthogonal target DNA used in the system. (4) Engineered synTF that are further fused to a ligand binding domain or a dimerization domain. Engineered fusion protein comprising of synTF-[ligand binding domain] or [ligand binding domain]-synTF would facilitate nuclear translocation of the synTF in the presence of the ligand. (5) engineered zinc finger-containing fusion proteins, each fusion protein comprising an engineered zinc finger (ZF) arrays and a ligand binding domain or a protein interaction/dimerization domain, wherein the engineered ZF arrays are coupled to the ligand binding domain or the protein interaction/dimerization domain. The ZF-protein domain can be located at the N-terminus or the C-terminus of the described fusion containing a ligand binding domain or a protein interaction/dimerization domain. The design of the engineered zinc finger-containing fusion proteins are as follows: [ZF domain]-[ligand binding domain], [ZF domain]-[protein interaction/dimerization domain], [ligand binding domain]-[ZF domain], and [protein interaction/dimerization domain]-[ZF domain].

Provided herein are a class of engineered transcription factor proteins (synTFs) and corresponding responsive promoters capable of precisely controlling gene expression in eukaryotic cells. These synTFs are designed to have reduced or minimal binding potential in the host genome (i.e., "orthogonal" to the host mammalian genome). The synTF proteins described herein are based on engineered zinc finger arrays (ZFA), designed to bind a specific target DNA sequence that is about 10-20 nucleotide in length and that is distant (ie., orthogonal to) from host genome sequences.

Figure 2A:
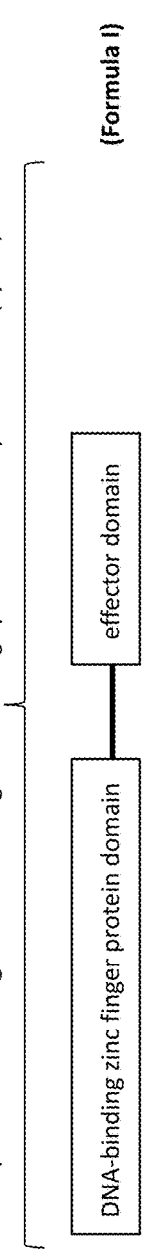
FIG. 2A shows the main components or domains of an engineered zinc finger-containing synthetic transcription factor (synTF).

Engineered, Zinc-Finger (ZF) Containing Transcription Factor Proteins (synTF) and otherZF Containing Fusion Proteins In one aspect, disclosed herein is an engineered synTF protein comprising of two main protein domains: (a) a first main domain which is a DNA-binding zinc finger protein domain, the ZF protein domain, and (b) a second domain through which the synTF exerts its effect, the effector domain, wherein the ZF protein domain and the effector domain are covalently linked together. See FIG. 2A.

In one embodiment, the engineered synTF protein further (c) a third main protein domain, a ligand binding domain or a protein interaction/dimerization domain, wherein the third main protein domain is covalently linked the synTF.

In one aspect, provided herein is a (synTF-[ligand binding domain]) fusion protein or ([ligand binding domain]-synTF) fusion protein. This design would cover any ZF-containing fused or covalently linked to a ligand binding domain, such as ERT2 (estrogen receptor ligand binding domain), thereby covering fusion proteins that are regulatable by chemical inducible systems. ERT2 is tamoxifen inducible. In one embodiment, the presence of tamoxifen or estrogen analogs induces the nuclear localization of a synTF-ERT2 or an ERT2-synTF fusion protein.

In one aspect, provided herein is a (synTF-[protein interaction domain]) or ([protein interaction domain]-synTF) fusion protein. This design would cover any ZF-containing fusion to a protein-protein interaction domain that could be used to mediate synTF multimerization. In one embodiment, the protein interaction domain allows dimerization of protein domains.

In one embodiment, the ligand binding domain is a steroid receptor ligand binding domain such as estrogen receptor. In one embodiment, the ligand is tamoxifen or other estrogen analogs. The fusion protein can have be designed as a synTF-[ligand binding domain] fusion protein or a [ligand binding domain]-synTF fusion protein, wherein the synTF is located at the N-terminus or the C-terminus of the ligand binding domain in the fusion protein, and wherein the conjugated ligand binding domain would facilitate nuclear translocation of the synTF in the presence of the ligand. Hence, the translocation of the synTF can be regulated by the presence of the ligand. The sequence of the exemplary estrogen receptor ligand binding domain is SEQ ID NO: 146.

In one embodiment, the ligand binding domain is VWF A1 domain and the corresponding ligand is the GP1bα subunit. The VWF A1 domain/GP1bα subunit forms a receptor ligand binding domain-ligand pair.

In other embodiments, the receptor ligand binding-ligand pair is selected from the group consisting of α4b7 integrin-madcam-1, αL integrin I domain-ICAM-1(D1+D2), αL integrin I domain-ICAM-3 (D1); and fimH pilin+lectin domain-N-linked carbohydrate.

Numerous receptor ligand binding-ligand pairs are known in the art, for examples, (1) the receptor-ligand pair is a WVF A1 domain and a GP1b α subunit, the template mRNAs for PCR cloning of a DNA encoding an A1 domain and a GP1b α can be the *Homo sapiens* glycoprotein Ib (platelet), alpha polypeptide (GP1BA) mRNA GENBANK™ Accession No. NM_000173.4; the von Willebrand factor A1 domain isoform 1 precursor mRNA GENBANK™ Accession No. NM_022834.4; and the von Willebrand factor A1 domain isoform 2 precursor mRNA GENBANK™ Accession No. NM_199121.2; (2) the receptor-ligand pair is an α4b7 integrin and a madcam-1, the template mRNAs for PCR cloning of a DNA encoding an α4b7 integrin and a madcam-1 can be the *Homo sapiens* integrin alpha L isoform b precursor GENBANK™ Accession No. NM_001114380.1; the integrin alpha L isoform a precursor GENBANK™ Accession No. NM_002209.2; and the intercellular adhesion molecule 1 (ICAM-1) precursor GENBANK™ Accession No. NM_000201.2; (3) the receptor-ligand pair is an aL integrin I domain and an ICAM-1(D1+D2), the template mRNAs for PCR cloning of the DNAs encoding an aL integrin I domain and an ICAM-1(D1+D2) can be the mRNA of the integrin alpha L isoform a precursor GENBANK™ Accession No. NM_002209.2 and the mRNA of the *Homo sapiens* intercellular adhesion molecule 1 precursor (ICAM-1) GENBANK™ Accession No. NM_000201.2; (4) the receptor-ligand pair is the aL integrin I domain and ICAM-3(D1), the template mRNAs for PCR cloning of the DNAs encoding an aL integrin I domain and an ICAM-3(D1) can be the mRNA of the integrin alpha L isoform a precursor GENBANK™ Accession No. NM_002209.2 and the mRNA of the *Homo sapiens* intercellular adhesion molecule 3 precursor (ICAM-3) GENBANK™ Accession No. NM_002162.3. The I domain encompasses amino acid residues 145-324 of the 1145 amino acid long mature αL integrin subunit protein (amino acid residues 26-1170 of GenBank Accession No. NP_002200); and (5) the receptor-ligand pair is a fimH pilin+lectin domain and a N-linked carbohydrates, the template mRNA for PCR cloning the DNA encoding a fimH pilin+lectin domain can be the *Escherichia coli* strain J96 type 1 fimbrial adhesin precursor (fimH) gene, GENBANK™ Accession No. AY914173, described in PCT publication WO2011103049, the contents of which are incorporated herein by reference in its entirety.

In one embodiment, the protein interaction/dimerization domain is the dimerization domain of ABI1, PYL1, FKBP (FK506 binding protein) or Frb (FKBP-Fap binding domain of mTOR). The protein interaction/dimerization domains of ABI1 and PYL1 dimerized upon the presence of ABA (Abscisic acid). FKBP and Frb dimerized upon the presence of rapamycin. Exemplary sequences of ABI1, PYL1, FKBP, and Frb are SEQ ID NO: 142-145 respectively. In some embodiments, the dimerizations are inducible by the presence of a chemical, e.g., abscisic acid induces the dimerization of ABI1 and PYL1, and rapamycin induces the dimerization of FKBP and Frb.

Alternatively, the two main protein domains (a) and (b) described herein in the engineered synTFs can be "split" into two separate and distinct fusion proteins, a first fusion protein containing the ZF protein domain and a second fusion protein containing the effector domain, wherein the ZF domains and effector domains are each fused to one half of a chemically-inducible dimerization domain.

In another aspect, provided herein is a novel class of engineered zinc finger-containing fusion proteins, each fusion protein comprising (1) an engineered zinc finger (ZF) arrays and (2) a ligand binding domain or a protein interaction/dimerization domain, wherein the engineered ZF arrays are coupled to the ligand binding domain or the protein interaction/dimerization domain. The ZF-containing protein domain (ZF protein domain) can be located at the N-terminus or the C-terminus of the described fusion containing a ligand binding domain or a protein interaction/dimerization domain. The various designs of the engineered zinc finger-containing fusion proteins are as follows: [ZF domain]-[ligand binding domain], [ZF domain]-[protein interaction/dimerization domain], [ligand binding domain]-[ZF domain], and [protein interaction/dimerization domain]-[ZF domain].

As described above, in one embodiment, the ligand binding domain is a steroid receptor ligand binding domain such as estrogen receptor. In one embodiment, the ligand is tamoxifen or other estrogen analogs. The conjugated ligand binding domain would facilitate nuclear translocation of the ZF in the presence of the ligand. Hence, the translocation of the ZF domain can be regulated by the presence of the ligand.

In one embodiment, the ligand binding domain is VWF A1 domain and the corresponding ligand is the GP1bα subunit. The VWF A1 domain/GP1bα subunit forms a receptor ligand binding domain-ligand pair.

In other embodiments, the receptor ligand binding-ligand pair is selected from the group consisting of α4b7 integrin-madcam-1, αL integrin I domain-ICAM-1(D1+D2), αL integrin I domain-ICAM-3 (D1); and fimH pilin+lectin domain-N-linked carbohydrate.

In one embodiment, provided is a first fusion protein comprising a ZF protein domain that is fused to a first protein interaction/dimerization domain, e.g., PYL1 (Abscisic Acid Receptor) or ABI1 (Abscisic Acid Insensitive 1), forming a fusion ZF-containing protein.

In another example, the ZF protein domain is fused to FKBP (FK506 Binding Protein) or Frb, each is another example of a protein interaction/dimerization domain.

In one embodiment, provided is a second fusion protein comprising an effector domain or an epigenetic effector domain that is fused to a second protein interaction/dimerization domain, e.g., PYL1 (Abscisic Acid Receptor) or ABI1 (abscisic acid Insensitive 1), forming a fusion effector-containing protein. The first and second protein interaction/dimerization domains in the first and second fusion are not the same, and that first and second protein interaction/dimerization domains can dimerize together. The inventors constructed and test a chemical inducible ZF-VP64 system, based on the ABI1/PYL1 plant abscisic acid system. SEQ ID NO: 133 shows the nucleic acid construct for the expression of a first fusion protein and second fusion protein from a single expression vector. The ZF protein domain comprising the ZF10-1 helix combo is linked to ABI1, forming the first fusion protein. A nuclear locatization signal (NLS) is included in the design. The second fusion protein comprises the VP64 transactivation effector domain linked to PYL1. A P2A sequence is include to facilate the separation of the first and second fusion proteins from each other in the primary transcript.

For example, the first fusion protein comprises the ZF protein domain that is fused to PYL1 and the second fusion protein comprises the effector domain that is fused to ABI1. When these first and second fusion proteins are mixed together in the presence of abscisic acid, the dimerization of PYL1 with ABI1 is induced and the ZF protein domain of the first fusion protein would be brought in closer proximity to the effector domain of the second fusion protein.

For another example, the first fusion protein comprises the ZF protein domain that is fused to FKBP (FK506 Binding Protein) and the second fusion protein comprises the effector domain that is fused to Frb (FKBP-Rap binding domain of mTOR). When these first and second fusion proteins are mixed together in the presence of rapamycin or rapalogs, the dimerization of FKBP with Frb is induced and the ZF protein domain of the first fusion protein would be brought in closer proximity to the effector domain of the second fusion protein.

In one embodiment of any aspect described herein, the ZF protein domain of any engineered fusion protein described herein is located at the N-terminus or the C-terminus of the effector domain (Formula I and Formula IV respectively), or the N-terminus or the C-terminus of the ligand binding domain or the protein interaction/dimerization domain. See FIGS. 2A and 3. For example, the ZF protein domain and the effector domain are covently conjugated to each other by a peptide linker to form a chimeric fusion protein.

Figure 2B:
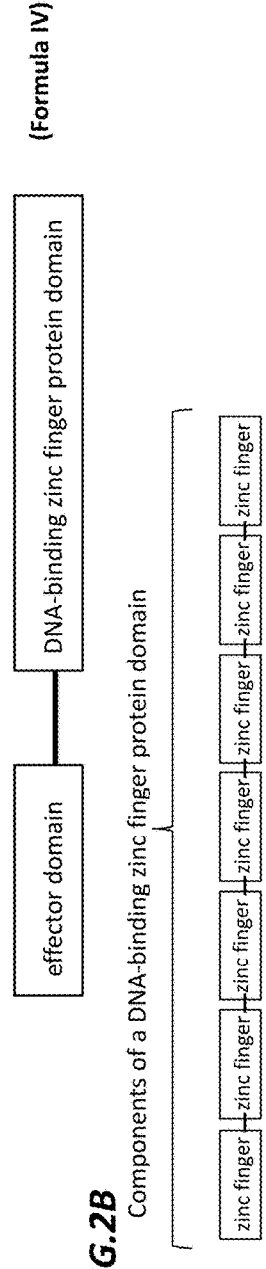
FIG. 2B shows the main components of a DNA-binding zinc finger protein domain (ZF protein domain), and a zinc finger array (ZFA) consisting of seven zinc fingers (ZFs). A ZF protein domain can have up to eight ZYs.
Figure 2C:
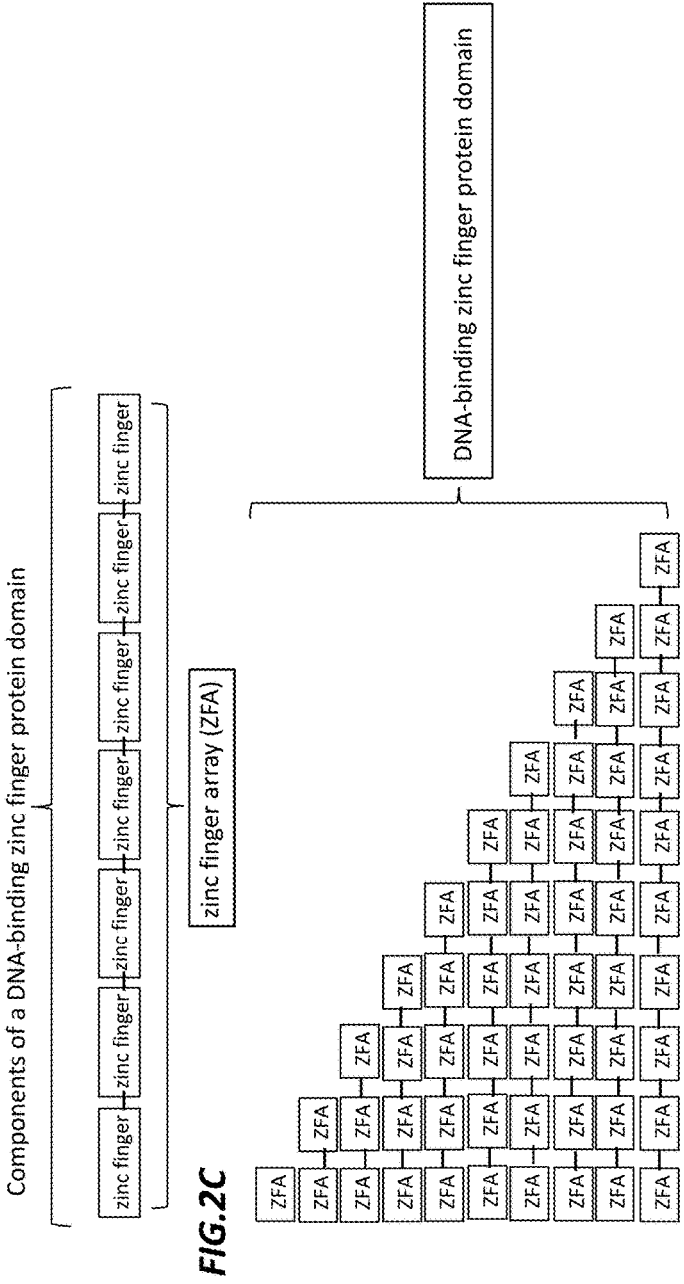
FIG. 2C shows the modular design of ZF protein domains where ZF protein domains can have a single zinc finger array (ZFA) or have as many as up to ten ZFAs.

The ZF protein domain is modular in design, with zinc finger arrays (ZFA) as the main components, and each ZFA is made of 6-8 ZF motifs. See FIG. 2B. The ZF protein domain comprises at least one ZFA, and can contain as many as up to ten ZFA. The ZF protein domain can have one and up to ten ZFA. See FIG. 2C.

In some embodiments of any aspect described herein, the effector domain is replaced with the ligand binding domain or the protein interaction/dimerization domain.

The design of the synTF or any engineered fusion protein described herein is also modular, meaning the synTF is made up of modules of ZF domains (ZFA) and modules of effector domains/protein interaction domains/ligand binding domains/dimerization domains, the individual modules are covalently conjugated together as described herein, and the individual modules function independently of each other. See FIG. 2A. The number of ZFA can range from one, two, three, four, five, six, seven, eight, nine, and up to ten. When there are two or more ZFA, the ZFAs are covalently conjugated to each other in tandem, e.g., by a peptide linker, L1, in an $NH_2$— to COOH— terminus arrangement to form an array of ZFA. See FIG. 2B. The ZFAs, as a whole, forms the ZF protein domain, is covalently linked to the N-terminus or the C-terminus of the effector domain. See FIG. 2A. There is at least one effector domain in each synTF.

According, disclosed herein is an engineered zinc-finger-containing synTF protein comprising (a) a DNA-binding zinc finger protein domain, and (b) an effector domain. In one aspect, disclosed herein is an engineered zinc-finger-containing synTF protein having the formula I: [DNA-binding zinc finger protein domain]-[effector domain] or having the formula IV: [effector domain]-[DNA-binding zinc finger protein domain]. Non-limiting examples of synTF proteins having ZF protein domains consisting of two, three, five, six, or eight ZFAs are as follows:

[(ZFA-1)-(ZFA-2)]-[effector domain];
[(ZFA-1)-(ZFA-2)-(ZFA-3)]-[effector domain];
(ZFA-1)-(ZFA-2)-(ZFA-3)-(ZFA-4)-(ZFA-5)]-[effector domain];
[(ZFA-1)-(ZFA-2)-(ZFA-3)-(ZFA-4)-(ZFA-5)-(ZFA-6)]-[effector domain]; and
[(ZFA-1)-(ZFA-2)-(ZFA-3)-(ZFA-4)-(ZFA-5)-(ZFA-6)-(ZFA-7)-(ZFA-8)]-[effector domain]

FIG. 3 shows more designs of several embodiments of synTFs encompassed in this disclosure.

When there are two or more ZFAs present in the ZF protein domain of a synTF or a ZF containing fusion protein described herein, the ZFAs can be the same, or different. For example, in a two-ZFA containing synTF, [(ZFA-1)-(ZFA-2)]-[effector domain], the ZFA-1 and ZFA-2 are the same, and have the same amino acid sequence. Alternatively, ZFA-1 and ZFA-2 are different, and have different amino acid sequence.

Each modular ZFA in the ZF protein domain of a synTF disclosed herein or a ZF containing fusion protein described herein is comprised of six to eight ZF motifs. See FIG. 2B for an example of a single ZFA having seven ZF motifs, a seven-finger ZFA. The ZF motif is a small protein structural motif consisting of an α helix and an antiparallel β sheet (αββ) and is characterized by the coordination of one zinc ion by two histidine residues and two cysteine residues in the motif in order to stabilize the finger-like protrusion fold, the "finger". The ZF motif in the ZF protein domain of a synTF disclosed herein is a $Cys_2His_2$ zinc finger motif. In one embodiment, the ZF motif comprises, consisting essentially of, or consisting of a peptide of formula II: $[X_{0-3}CX_{1-5}CX_{2-7}\text{-(helix)-}HX_{3-6}H]$ (SEQ ID NO: 19) wherein X is any amino acid, the subscript numbers indicate the possible number of amino acid residues, C is cysteine, H is histidine, and (helix) is a-six contiguous amino acid residue peptide that forms a short alpha helix. The helix is variable. This short alpha helix forms one facet of the finger formed by the coordination of the zinc ion by two histidine residues and two cysteine residues in the ZF motif. For each ZFA, the six to eight ZF motifs therein are linked to each other, $NH_2$— to COOH— terminus by a peptide linker having about four to six amino acid residues to form an array of ZF motifs or ZF. The finger-like protrusion fold of each ZF motif interacts with and binds nucleic acid sequence. Approximately a peptide sequence for two ZF motif interacts with and binds a ~six-base pair (bp) nucleic acid sequence. The multiple ZF motifs in a ZFA form finger-like protrusions that would make contact with an orthogonal target DNA sequence. Hence, for example, a ZFA with six ZF motifs or finger-like protrusions (a six-finger ZFA) interacts and binds a ~18-20 bp nucleic acid sequence, and a eight-finger ZFA would bind a ~24-26 bp nucleic acid sequence. Accordingly, in one embodiment, the ZFA in the ZF protein domain of a synTF comprises, consists essentially of, or consists of a sequence: N'-[(formula II)-$L_2$]$_{6-8}$-C', where the subscript 6-8 indicates the number of ZF motifs, the $L_2$ is a linker peptide having 4-6 amino acid residues, and the N'- and C'- indicates the N-terminus and C-terminus respectively of the peptide sequence. For example, for a ZFA consists essentially of six ZF motifs, the sequence is N'-[(formula II)-L]-[(formula II)-$L_2$]-[(formula II)-$L_2$]-[(formula II)-$L_2$]-[(formula II)-$L_2$]-[(formula II)-$L_2$]-C', and a ZFA consists essentially of eight ZF motifs, the sequence is N'-[(formula II)-$L_2$]-[(formula II)-$L_2$]-[(formula II)-$L_2$]-[(formula II)-$L_2$]-[(formula II)-$L_2$]-[(formula II)-$L_2$]-]-[(formula II)-$L_2$]-[(formula II)-$L_2$]-C'.

In another embodiment of any aspect described herein, the ZF motif comprises a peptide of formula III: $[X_3CX_2CX_5\text{-(helix)-}HX_3H]$ (SEQ ID NO: 20) wherein X is any amino acid, the subscript numbers indicate the possible number of amino acid residues, C is cysteine, H is histidine, and (helix) is a-six contiguous amino acid residue peptide that forms a short alpha helix. Accordingly, in one embodiment, the ZFA in the ZF protein domain of a synTF comprises, consists essentially of, or consists of a sequence: N'-[(formula III)-$L_2$]$_{6-8}$-C', where the subscript 6-8 indicates the number of ZF motifs, the $L_2$ is a linker peptide having 4-6 amino acid residues, and the N'- and C'- indicates the N-terminus and C-terminus respectively of the peptide sequence. For example, for a ZFA consists essentially of six ZF motifs, the sequence is N'-[(formula III)-$L_2$]-[(formula III)-$L_2$]-[(formula III)-$L_2$]-[(formula III)-$L_2$]-[(formula III)-$L_2$]-[(formula III)-$L_2$]-C' and a ZFA consists essentially of eight ZF motifs, the sequence is N'-[(formula III)-$L_2$-[(formula III)-$L_2$]-[(formula III)-$L_2$]-[(formula III)-$L_2$]-[(formula III)-L]-[(formula III)-L]-[(formula III)-$L_2$]-]-[(formula III)-$L_2$]-[(formula III)-$L_2$]-C'.

In one embodiment of any aspect described herein, for a single ZFA is the ZF protein domain of a synTF disclosed herein, the ZFA in the ZF protein domain comprises, consists essentially of, or consists of a sequence: N'-PGERPFQCRICMRNFS-(Helix 1)-HTRTHTGEKPFQCRICMRNFS-(Helix 2)-HLRTHTGSQK PFQCRICMRNFS-(Helix 3)-HTRTHTGEK PFQCRICMRNFS-(Helix 4)-HLRTHTGSQKPFQCRICMRNFS-(Helix 5)-HTRTHTGEK PFQCRICMRNFS-(Helix 6)-HLRTHLR-C' (SEQ ID NO: 21), wherein the (Helix) is a-six contiguous amino acid residue peptide that forms a short alpha helix. In one embodiment, all six of the helix 1, 2, 3, 4, 5 and 6 are distinct and different from each other. In another embodiment, all six of the helix 1, 2, 3, 4, 5 and 6 are identical to each other. Alternatively, at least two of the six helices are identical and the same with each other. In other embodiments, at least three of the six helices in a ZFA are identical and the same with each other, at least four of the six helices in a ZFA are identical and the same with each other, or at least five of the six helices in a ZFA are identical and the same with each other.

In some embodiments of any aspect described herein, the helices of the six to eight ZF motifs of an individual ZFA disclosed herein are selected from the six-amino acid residue peptide sequences disclosed in one of the following Groups 1-11. In some embodiments, at least four of the ZF motifs in an individual ZFA disclosed herein are selected from the six-amino acid residue peptide sequences disclosed in one of the following Groups 1-11. In other embodiments, all of the ZF motifs, ie. the six, seven or eight ZF motifs in an individual ZFA disclosed herein, are selected from the six amino acid residue peptide sequences disclosed in one of the following Groups 1-11. In any individual ZFA, the helix selected for a single ZF comprising the ZFA can be repeated twice or more in the ZFA. This means that for any given single ZFA, at least four or all the helices in the ZFA are selected from the same group disclosed herein. For example, wherein a ZFA consists essentially of six ZF motifs, that means there are six alpha helices. All the 6-8 helices (Helix 1; Helix 2; Helix 3; Helix 4; Helix 5; Helix 6; Helix 7; Helix 8) of the ZFs in an individual ZFA is selected from one of the following group 1-11, for example, all six helices are selected from group 2. That is, all the helices for all the ZF comprising a single ZFA come from the same group. Alternatively, at least four of the six helices are selected from the same group, a group selected from group 1-11. For example, four of the six helices are selected from group 5, and the reminder two helices of the six-ZF motif ZFA are selected from the other groups 1-4, 6-11, or can be any other helices that would form a short alpha helix. The other remaining helices making up the ZFA can those that are known in the art.

| Group 1 | SEQ ID NO: | Group 2 | SEQ ID NO: | Group 3 | SEQ ID NO: | Group 4 | SEQ ID NO: |
|---|---|---|---|---|---|---|---|
| DEANLRR | 22 | QRSSLVR | 31 | QRSSLVR | 31 | QQTNLTR | 26 |
| DPSVLKR | 23 | DMGNLGR | 32 | DKSVLAR | 40 | QGTSLAR | 46 |
| QSANLLR | 24 | RSHDLTR | 33 | QTNNLGR | 41 | VRHNLTR | 47 |
| DPSSLKR | 25 | HKSSLTR | 34 | THAVLTR | 42 | DKSVLAR | 40 |
| QQTNLTR | 26 | DSSNLRR | 35 | DRGNLTR | 38 | DSSNLRR | 35 |
| DATQLVR | 27 | DQGNLIR | 36 | TKSLLAR | 43 | DQGNLIR | 36 |
| ERRSLAR | 28 | QKQALTR | 37 | QKQALDR | 44 | EKQNLAR | 48 |
| EEANLRR | 29 | DRGNLTR | 38 | DTSVLNR | 45 | DPSNLRR | 49 |
| DHSSLKR | 30 | RSHDLTV | 39 | | | DHSNLSR | 50 |
| | | | | | | QSTSLQR | 51 |

| Group 5 | SEQ ID NO: | Group 6 | SEQ ID NO: | Group 7 | SEQ ID NO: |
|---|---|---|---|---|---|
| NMSNLTR | 52 | QQTNLTR | 26 | QRSSLVR | 31 |
| DRSVLRR | 53 | QGGNLAL | 60 | QRGNLNM | 64 |
| LQENLTR | 54 | DHSSLKR | 30 | RPQELRR | 65 |
| DRSSLRR | 55 | RADMLRR | 61 | DHSSLKR | 30 |
| QSGTLHR | 56 | DSSNLRR | 35 | RQDNLGR | 66 |
| QLANLAR | 57 | DQGNLIR | 36 | DGGNLGR | 67 |
| DQTTLRR | 58 | EKQNLAR | 48 | QQGNLQL | 68 |
| DPSNLAR | 59 | DPSNLRR | 49 | RRQELTR | 69 |
| | | QKANLGV | 62 | DPSNLRR | 49 |
| | | RLDMLAR | 63 | | |

| Group 8 | SEQ ID NO: | Group 9 | SEQ ID NO: | Group 10 | SEQ ID NO: | Group 11 | SEQ ID NO: |
|---|---|---|---|---|---|---|---|
| QASNLTR | 70 | DSSNLRR | 35 | RRHGLDR | 75 | QLSNLTR | 77 |
| DHSSLKR | 30 | DQGNLIR | 36 | DHSSLKR | 30 | DRSSLKR | 78 |
| RAHNLLL | 71 | RAHNLLL | 71 | VRHNLTR | 47 | QRSSLVR | 31 |
| QRSSLVR | 31 | QRSSLVR | 31 | DHSNLSR | 50 | RLDMLAR | 63 |
| QSTTLKR | 72 | QSTTLKR | 72 | QRSSLVR | 31 | VRHSLTR | 79 |
| DPSNLRR | 49 | DPSNLRR | 49 | ESGHLKR | 76 | ESGALRR | 80 |
| QGTTLKR | 73 | EKQNLAR | 48 | | | | |
| QRSNLAR | 74 | DSSNLRR | 35 | | | | |

Non-limiting examples of the combinations and arrangements of six helices in a single ZFA where the helices are selected from Group 1 and where the motifs are in an NH$_2$— to COOH— terminus arrangement, (Group 1 ZFA helix combo), are as follows:

ZF 1-1: N'-DEANLRR, DPSVLKR, QSANLLR, DPSSLKR, QQTNLTR, DATQLVR-C' (SEQ ID NOS 22, 23, 24, 25, 26, and 27, respectively, in order of appearance)

ZF 1-2: N'-DEANLRR, DPSVLKR, QSANLLR, DPSSLKR, QQTNLTR, ERRSLAR-C' (SEQ ID NOS 22, 23, 24, 25, 26, and 28, respectively, in order of appearance)

ZF 1-3: N'-EEANLRR, DHSSLKR, QSANLLR, DPSSLKR QQTNLTR, DATQLVR-C' (SEQ ID NOS 29, 30, 24, 25, 26, and 27, respectively, in order of appearance)

ZF 1-4: N'-EEANLRR, DHSSLKR, QSANLLR, DPSSLKR QQTNLTR, ERRSLAR-C' (SEQ ID NOS 29, 30, 24, 25, 26, and 28, respectively, in order of appearance)

ZF 1-5: N'-DEANLRR, DPSVLKR, QQTNLTR, ERRSLAR QQTNLTR, DATQLVR-C' (SEQ ID NOS 22, 23, 26, 28, 26, and 27, respectively, in order of appearance)

ZF 1-6: N'-DEANLRR, DPSVLKR, QQTNLTR, ERRSLAR QQTNLTR, ERRSLAR-C' (SEQ ID NOS 22, 23, 26, 28, 26, and 28, respectively, in order of appearance)

ZF 1-7: N'-EEANLRR, DHSSLKR, QQTNLTR, ERRSLAR QQTNLTR, DATQLVR-C' (SEQ ID NOS 29, 30, 26, 28, 26, and 27, respectively, in order of appearance)

ZF 1-8: N'-EEANLRR, DHSSLKR, QQTNLTR, ERRSLAR QQTNLTR, ERRSLAR-C' (SEQ ID NOS 29, 30, 26, 28, 26, and 28, respectively, in order of appearance)

Non-limiting examples of the combinations and arrangements of six helices in a single six-finger ZFA where the helices are selected from Group 2 and where the motifs are in an NH$_2$— to COOH— terminus arrangement, (Group 2 ZFA helix combo), are as follows:

ZF 2-1: N'-QRSSLVR, DMGNLGR, RSHDLTR, HKSSLTR, DSSNLRR, DQGNLIR-C' (SEQ ID NOS 31, 32, 33, 34, 35, and 36, respectively, in order of appearance)

ZF 2-2: N'-QKQALTR, DRGNLTR, RSHDLTR, HKSSLTR, DSSNLRR, DQGNLIR-C' (SEQ ID NOS 37, 38, 33, 34, 35, and 36, respectively, in order of appearance)

ZF 2-3: N'-QRSSLVR, DMGNLGR, RSHDLTV, HKSSLTR, DSSNLRR, DQGNLIR-C' (SEQ ID NOS 31, 32, 39, 34, 35, and 36, respectively, in order of appearance)

ZF 2-4: N'-QKQALTR, DRGNLTR, RSHDLTV, HKSSLTR, DSSNLRR, DQGNLIR-C' (SEQ ID NOS 37, 38, 39, 34, 35, and 36, respectively, in order of appearance)

ZF 2-5: N'-QRSSLVR, DMGNLGR, RSHDLTR, HKSSLTR, EKQNLAR, DPSNLRR-C' (SEQ ID NOS 31, 32, 33, 34, 48, and 49, respectively, in order of appearance)

ZF 2-6: N'-QKQALTR, DRGNLTR, RSHDLTR, HKSSLTR, EKQNLAR, DPSNLRR-C' (SEQ ID NOS 37, 38, 33, 34, 48, and 49, respectively, in order of appearance)

ZF 2-7: N'-QRSSLVR, DMGNLGR, RSHDLTV, HKSSLTR, EKQNLAR, DPSNLRR-C' (SEQ ID NOS 31, 32, 39, 34, 48, and 49, respectively, in order of appearance)

ZF 2-8: N'-QKQALTR, DRGNLTR, RSHDLTV, HKSSLTR, EKQNLAR, DPSNLRR-C' (SEQ ID NOS 37, 38, 39, 34, 48, and 49, respectively, in order of appearance)

Non-limiting examples of the combinations and arrangements of six helices in a single six-finger ZFA where the helices are selected from Group 3 and where the motifs are in an NH$_2$— to COOH— terminus arrangement, (Group 3 ZFA helix combo), are as follows:

ZF 3-1: N'-QRSSLVR, DKSVLAR, QRSSLVR, QTNNLGR, THAVLTR, DRGNLTR-C' (SEQ ID NOS 31, 40, 31, 41, 42, and 38, respectively, in order of appearance)

ZF 3-2: N'-QRSSLVR, DKSVLAR, QRSSLVR, QTNNLGR, TKSLLAR, DRGNLTR-C' (SEQ ID NOS 31, 40, 31, 41, 43, and 38, respectively, in order of appearance)

ZF 3-3: N'-QKQALDR, DTSVLNR, QRSSLVR, QTNNLGR, THAVLTR, DRGNLTR-C' (SEQ ID NOS 44, 45, 31, 41, 42, and 38, respectively, in order of appearance)

ZF 3-4: N'-QKQALDR, DTSVLNR, QRSSLVR, QTNNLGR, TKSLLAR, DRGNLTR-C' (SEQ ID NOS 44, 45, 31, 41, 43, and 38, respectively, in order of appearance)

ZF 3-5: N'-QRSSLVR, DKSVLAR, QRSSLVR, QTNNLGR, THAVLTR, DRGNLTR-C' (SEQ ID NOS 31, 40, 31, 41, 42, and 38, respectively, in order of appearance)

ZF 3-6: N'-QRSSLVR, DKSVLAR, QRSSLVR, QTNNLGR, TKSLLAR, DRGNLTR-C' (SEQ ID NOS 31, 40, 31, 41, 43, and 38, respectively, in order of appearance)

ZF 3-7: N'-QKQALDR, DTSVLNR, QRSSLVR, QTNNLGR, THAVLTR, DRGNLTR-C' (SEQ ID NOS 44, 45, 31, 41, 42, and 38, respectively, in order of appearance)

ZF 3-8: N'-QKQALDR, DTSVLNR, QRSSLVR, QTNNLGR, TKSLLAR, DRGNLTR-C' (SEQ ID NOS 44, 45, 31, 41, 43, and 38, respectively, in order of appearance)

Non-limiting examples of the combinations and arrangements of six helices in a single six-finger ZFA where the helices are selected from Group 4 and where the motifs are in an NH$_2$— to COOH— terminus arrangement, (Group 4 ZFA helix combo), are as follows:

ZF 4-1: N'-QQTNLTR, QGTSLAR, VRHNLTR, DKSVLAR, DSSNLRR, DQGNLIR-C' (SEQ ID NOS 26, 46, 47, 40, 35, and 36, respectively, in order of appearance)

ZF 4-2: N'-QQTNLTR, QGTSLAR, VRHNLTR, DKSVLAR, EKQNLAR, DPSNLRR-C' (SEQ ID NOS 26, 46, 47, 40, 48, and 49, respectively, in order of appearance)

ZF 4-3: N'-QQTNLTR, QGTSLAR, VRHNLTR, DHSNLSR, DSSNLRR, DQGNLIR-C' (SEQ ID NOS 26, 46, 47, 50, 35, and 36, respectively, in order of appearance)

ZF 4-4: N'-QQTNLTR, QGTSLAR, VRHNLTR, DHSNLSR, EKQNLAR, DPSNLRR-C' (SEQ ID NOS 26, 46, 47, 50, 48, and 49, respectively, in order of appearance)

ZF 4-5: N'-QQTNLTR, QSTSLQR, VRHNLTR, DKSVLAR, DSSNLRR, DQGNLIR-C' (SEQ ID NOS 26, 51, 47, 40, 35, and 36, respectively, in order of appearance)

ZF 4-6: N'-QQTNLTR, QSTSLQR, VRHNLTR, DKSVLAR, EKQNLAR, DPSNLRR-C' (SEQ ID NOS 26, 51, 47, 40, 48, and 49, respectively, in order of appearance)

ZF 4-7: N'-QQTNLTR, QSTSLQR, VRHNLTR, DHSNLSR, DSSNLRR, DQGNLIR-C' (SEQ ID NOS 26, 51, 47, 50, 35, and 36, respectively, in order of appearance)

ZF 4-8: N'-QQTNLTR, QSTSLQR, VRHNLTR, DHSNLSR, EKQNLAR, DPSNLRR-C' (SEQ ID NOS 26, 51, 47, 50, 48, and 49, respectively, in order of appearance)

Non-limiting examples of the combinations and arrangements of six helices in a single six-finger ZFA where the helices are selected from Group 5 and where the motifs are in an NH$_2$— to COOH— terminus arrangement, (Group 5 ZFA helix combo), are as follows:

ZF 5-1: N'-NMSNLTR, DRSVLRR, LQENLTR, DRSSLRR, QSGTLHR, QSGTLHR-C' (SEQ ID NOS 52, 53, 54, 55, 56, and 56, respectively, in order of appearance)

ZF 5-2: N'-QLANLAR, DQTTLRR, LQENLTR, DRSSLRR, QSGTLHR, QSGTLHR-C' (SEQ ID NOS 57, 58, 54, 55, 56, and 56, respectively, in order of appearance)

ZF 5-3: N'-NMSNLTR, DRSVLRR, DPSNLAR, DRSSLRR, QSGTLHR, QSGTLHR-C' (SEQ ID NOS 52, 53, 59, 55, 56, and 56, respectively, in order of appearance)

ZF 5-4: N'-QLANLAR, DQTTLRR, DPSNLAR, DRSSLRR, QSGTLHR, QSGTLHR-C' (SEQ ID NOS 57, 58, 59, 55, 56, and 56, respectively, in order of appearance)

ZF 5-5: N'-NMSNLTR, DRSVLRR, LQENLTR, DRSSLRR, QSGTLHR, QSGTLHR-C' (SEQ ID NOS 52, 53, 54, 55, 56, and 56, respectively, in order of appearance)

ZF 5-6: N'-QLANLAR, DQTTLRR, LQENLTR, DRSSLRR, QSGTLHR, QSGTLHR-C' (SEQ ID NOS 57, 58, 54, 55, 56, and 56, respectively, in order of appearance)

ZF 5-7: N'-NMSNLTR, DRSVLRR, DPSNLAR, DRSSLRR, QSGTLHR, QSGTLHR-C' (SEQ ID NOS 52, 53, 59, 55, 56, and 56, respectively, in order of appearance)

ZF 5-8: N'-QLANLAR, DQTTLRR, DPSNLAR, DRSSLRR, QSGTLHR, QSGTLHR-C' (SEQ ID NOS 57, 58, 59, 55, 56, and 56, respectively, in order of appearance)

Non-limiting examples of the combinations and arrangements of six helices in a single six-finger ZFA where the helices are selected from Group 6 and where the motifs are in an NH$_2$— to COOH— terminus arrangement, (Group 6 ZFA helix combo), are as follows:

ZF 6-1: N'-QQTNLTR, QGGNLAL, DHSSLKR, RADMLRR, DSSNLRR, DQGNLIR-C' (SEQ ID NOS 26, 60, 30, 61, 35, and 36, respectively, in order of appearance)

ZF 6-2: N'-QQTNLTR, QGGNLAL, DHSSLKR, RADMLRR, EKQNLAR, DPSNLRR-C' (SEQ ID NOS 26, 60, 30, 61, 48, and 49, respectively, in order of appearance)

ZF 6-3: N'-QQTNLTR, QKANLGV, DHSSLKR, RADMLRR, DSSNLRR, DQGNLIR-C' (SEQ ID NOS 26, 62, 30, 61, 35, and 36, respectively, in order of appearance)

ZF 6-4: N'-QQTNLTR, QKANLGV, DHSSLKR, RADMLRR, EKQNLAR, DPSNLRR-C' (SEQ ID NOS 26, 62, 30, 61, 48, and 49, respectively, in order of appearance)

ZF 6-5: N'-QQTNLTR, QGGNLAL, DHSSLKR, RLDMLAR, DSSNLRR, DQGNLIR-C' (SEQ ID NOS 26, 60, 30, 63, 35, and 36, respectively, in order of appearance)

ZF 6-6: N'-QQTNLTR, QGGNLAL, DHSSLKR, RLDMLAR, EKQNLAR, DPSNLRR-C' (SEQ ID NOS 26, 60, 30, 63, 48, and 49, respectively, in order of appearance)

ZF 6-7: N'-QQTNLTR, QKANLGV, DHSSLKR, RLDMLAR, DSSNLRR, DQGNLIR-C' (SEQ ID NOS 26, 62, 30, 63, 35, and 36, respectively, in order of appearance)

ZF 6-8: N'-QQTNLTR, QKANLGV, DHSSLKR, RLDMLAR, EKQNLAR, DPSNLRR-C' (SEQ ID NOS 26, 62, 30, 63, 48, and 49, respectively, in order of appearance)

Non-limiting examples of the combinations and arrangements of six helices in a single six-finger ZFA where the helices are selected from Group 7 and where the motifs are in an NH$_2$— to COOH— terminus arrangement, (Group 7 ZFA helix combo), are as follows:

ZF 7-1: N'-QRSSLVR, QRGNLNM, RPQELRR, DHSSLKR, RQDNLGR, DGGNLGR-C' (SEQ ID NOS 31, 64, 65, 30, 66, and 67, respectively, in order of appearance)

ZF 7-2: N'-QRSSLVR, QQGNLQL, RPQELRR, DHSSLKR, RQDNLGR, DGGNLGR-C' (SEQ ID NOS 31, 68, 65, 30, 66, and 67, respectively, in order of appearance)

ZF 7-3: N'-QRSSLVR, QRGNLNM, RRQELTR, DHSSLKR, RQDNLGR, DGGNLGR-C' (SEQ ID NOS 31, 64, 69, 30, 66, and 67, respectively, in order of appearance)

ZF 7-4: N'-QRSSLVR, QQGNLQL, RRQELTR, DHSSLKR, RQDNLGR, DGGNLGR-C' (SEQ ID NOS 31, 68, 69, 30, 66, and 67, respectively, in order of appearance)

ZF 7-5: N'-QRSSLVR, QRGNLNM, RPQELRR, DHSSLKR, RQDNLGR, DPSNLRR-C' (SEQ ID NOS 31, 64, 65, 30, 66, and 49, respectively, in order of appearance)

ZF 7-6: N'-QRSSLVR, QQGNLQL, RPQELRR, DHSSLKR, RQDNLGR, DPSNLRR-C' (SEQ ID NOS 31, 68, 65, 30, 66, and 49, respectively, in order of appearance)

ZF 7-7: N'-QRSSLVR, QRGNLNM, RRQELTR, DHSSLKR, RQDNLGR, DPSNLRR-C' (SEQ ID NOS 31, 64, 69, 30, 66, and 49, respectively, in order of appearance)

ZF 7-8: N'-QRSSLVR, QQGNLQL, RRQELTR, DHSSLKR, RQDNLGR, DPSNLRR-C' (SEQ ID NOS 31, 68, 69, 30, 66, and 49, respectively, in order of appearance)

Non-limiting examples of the combinations and arrangements of six helices in a single six-finger ZFA where the helices are selected from Group 8 and where the motifs are in an NH$_2$— to COOH— terminus arrangement, (Group 8 ZFA helix combo), are as follows:

ZF 8-1: N'-QASNLTR, DHSSLKR, RAHNLLL, QRSSLVR, QSTTLKR, DPSNLRR-C' (SEQ ID NOS 70, 30, 71, 31, 72, and 49, respectively, in order of appearance)

ZF 8-2: N'-QASNLTR, DHSSLKR, RAHNLLL, QRSSLVR, QGTTLKR, DPSNLRR-C' (SEQ ID NOS 70, 30, 71, 31, 73, and 49, respectively, in order of appearance)

ZF 8-3: N'-QRSNLAR, DHSSLKR, RAHNLLL, QRSSLVR, QSTTLKR, DPSNLRR-C' (SEQ ID NOS 74, 30, 71, 31, 72, and 49, respectively, in order of appearance)

ZF 8-4: N'-QRSNLAR, DHSSLKR, RAHNLLL, QRSSLVR, QGTTLKR, DPSNLRR-C' (SEQ ID NOS 74, 30, 71, 31, 73, and 49, respectively, in order of appearance)

Non-limiting examples of the combinations and arrangements of six helices in a single six-finger ZFA where the helices are selected from Group 9 and where the motifs are in an NH$_2$— to COOH— terminus arrangement, (Group 9 ZFA helix combo), are as follows:

ZF 9-1: N'-DSSNLRR, DQGNLIR, RAHNLLL, QRSSLVR, QSTTLKR, DPSNLRR-C' (SEQ ID NOS 35, 36, 71, 31, 72, and 49, respectively, in order of appearance)

ZF 9-2: N'-EKQNLAR, DPSNLRR, RAHNLLL, QRSSLVR, QSTTLKR, DPSNLRR-C' (SEQ ID NOS 48, 49, 71, 31, 72, and 49, respectively, in order of appearance)

ZF 9-3: N'-DSSNLRR, DQGNLIR, RAHNLLL, QRSSLVR, QGTTLKR, DPSNLRR-C' (SEQ ID NOS 35, 36, 71, 31, 73, and 49, respectively, in order of appearance)

ZF 9-4: N'-EKQNLAR, DPSNLRR, RAHNLLL, QRSSLVR, QGTTLKR, DPSNLRR-C' (SEQ ID NOS 48, 49, 71, 31, 73, and 49, respectively, in order of appearance)

A non-limiting example of the combination and arrangement of six helices in a single six-finger ZFA where the helices are selected from Group 10 and where the motif are in an NH$_2$— to COOH— terminus arrangement, (Group 10 ZFA helix combo), is as follows:

ZF 10-1: N'-RRHGLDR, DHSSLKR, VRHNLTR, DHSNLSR, QRSSLVR, ESGHLKR-C' (SEQ ID NOS 75, 30, 47, 50, 31, and 76, respectively, in order of appearance)

A non-limiting example of the combination and arrangement of six helices in a single six-finger ZFA where the helices are selected from Group 11 and where the motif are in an NH$_2$— to COOH— terminus arrangement, (Group 11 ZFA helix combo), is as follows:

ZF 11-1: N'-QLSNLTR, DRSSLKR, QRSSLVR, RLDMLAR, VRHSLTR, ESGALRR-C' (SEQ ID NOS 77, 78, 31, 63, 79, and 80, respectively, in order of appearance)

Accordingly, provided herein, in some aspects, are engineered synTF or ZF-containing fusion proteins described herein comprising a ZF protein domain and an effector domain, or comprising a ZF protein domain, an effector domain, and a ligand binding domain, or comprising a ZF protein domain and a ligand binding domain or a dimerization domain, wherein the ZF protein domain comprises at least one ZFA having the ZFA helix combo selected from one of the ZFA helix combo Groups 1-11 disclosed herein. Where there are two or more ZFAs, (i.e., a ZF array) in the ZF protein domain, each ZFAs in the domain has a ZFA helix combo selected from one of the ZFA helix combo Groups 1-11 disclosed herein, and the selected ZFA helix combo groups can be different or duplicated for the each ZFAs in the ZF protein domain of the synTF. For example, when a synTF comprises a ZF protein domain consisting essentially of three ZFAs (ZFA-1-ZFA-2-ZFA-3 in a three-ZFA array) and an effector domain, ZFA-1 has a ZFA helix combo selected from the Group 1 ZFA helix combo, ZFA-2 has a ZFA helix combo selected from the Group 5 ZFA helix combo, and ZFA-3 has a ZFA helix combo selected from the Group 7 ZFA helix combo. In other embodiments, the selected ZFA helix combo groups can be duplicated or triplicated for the ZF array in the synTF. For example, in a three-ZFA array-containing ZF protein domain of a synTF, two of the ZFAs comprises ZFA helix combo selected from the same ZFA helix combo group, e.g., Group 2, and the third ZFA has a ZFA helix combo selected from a different ZFA helix combo group, e.g., Group 4. The two ZFAs having ZFA helix combos selected from the same Group 2 ZFA helix combo can have different or the same actual combination and arrangement of the helices ZFAs. For example, when the synTF comprises of a ZF protein domain consisting essentially of five ZFAs (ZFA-1-ZFA-2-ZFA-3-ZFA-4-ZFA-5 in a five-ZFA array) and an effector domain, ZFA-1 has a ZFA helix combo selected from the Group 1 ZFA helix combo, ZFA-2 has a ZFA helix combo selected from the Group 5 ZFA helix combo, ZFA-3 has a ZFA helix combo also selected from the Group 1 ZFA helix combo, ZFA-4 has a ZFA helix combo selected from the Group 4 ZFA helix combo, and ZFA-5 has a ZFA helix combo selected from the Group 2 ZFA helix combo. While ZFA-1 and ZFA-3 both have ZFA helix combo selected from the Group 1 ZFA helix combo, the actual combination and arrangement of the helices within ZFA-1 and ZFA-3 can be different or the same. For example, ZFA-1 and ZFA-3 have the ZFA helix combo ZF 1-1 and ZF 1-5 respectively, or both ZFA-1 and ZFA-3 have the ZFA helix combo ZF 1-1.

In other aspects, provided herein are engineered synTF or a ZF-containing fusion protein described herein comprising a ZF protein domain and an effector domain, or comprising a ZF protein domain, an effector domain, and a ligand binding domain, or comprising a ZF protein domain and a ligand binding domain or a dimerization domain, wherein the ZF protein domain comprises at least one ZFA having a ZFA helix combo selected from the group consisting of ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1 disclosed herein.

In some embodiments of any aspect described herein, in the synTF described or any ZF-containing fusion protein described herein, the individual ZFA therein described are specifically designed to bind orthogonal target DNA sequences such as the following:

Target 1:
(SEQ ID NO: 81)
5' C GTC GAA GTC GAA GTC GAC C 3'

Target 2:
(SEQ ID NO: 82)
5' G GAC GAC GTT ACG GAC GTA C 3'

Target 3:
(SEQ ID NO: 83)
5' A GAC GTC GAA GTA GCC GTA G 3'

Target 4:
(SEQ ID NO: 84)
5' G GAC GAC GCC GAT GTA GAA G 3'

Target 5:
(SEQ ID NO: 85)
5' T GAA GCA GTC GAC GCC GAA G 3'

Target 6:
(SEQ ID NO: 86)
5' G GAC GAC GCG GTC TAA GAA G 3'

Target 7:
(SEQ ID NO: 87)
5' C GAC GAG GTC GCA TAA GTA G 3'

Target 8:
(SEQ ID NO: 88)
5' A GAC GCA GTA TAG GTC GAA C 3'

Target 9:
(SEQ ID NO: 89)
5' A GAC GCA GTA TAG GAC GAC G 3'

Target 10:
(SEQ ID NO: 90)
5' C GGC GTA GCC GAT GTC GCG C 3'

Target 11:
(SEQ ID NO: 91)
5' G GTC GTT GCG GTA GTC GAA G 3'

In one embodiment of any aspect described herein, provided herein is a ZFA that comprises, consists of, or consist essentially of a sequence: N'-[(formula II)-L$_2$]$_{6-8}$-C' or a sequence N'-[(formula III)-L$_2$]$_{6-8}$-C' that targets a target DNA sequence selected from Target 1-11, wherein the formula II is [X$_{0-3}$CX$_{1-5}$CX$_{2-7}$-(helix)-HX$_{3-6}$H] (SEQ ID NO: 19) and the formula III is [X$_3$CX$_2$CX$_5$-(helix)-HX$_3$H] (SEQ ID NO: 20).

In other aspects, provided herein are engineered synTF or the ZF containing fusion protein described herein comprising a ZF protein domain and an effector domain, or comprising a ZF protein domain, an effector domain, and a ligand binding domain, or comprising a ZF protein domain and a ligand binding domain or a dimerization domain, wherein the ZF protein domain comprises at least one ZFA, wherein the an least ZFA comprises, consists of, or consist essentially of a sequence: N'-[(formula II)-L$_2$]$_{6-8}$-C' or a sequence N'-[(formula III)-L$_2$]$_{6-8}$-C', and wherein the ZFA(s) therein targets a target DNA sequence selected from Target 1-11, wherein the formula II is [X$_{0-3}$CX$_{1-5}$CX$_{2-7}$-(helix)-HX$_{3-6}$H](SEQ ID NO: 19) and the formula III is [X$_3$CX$_2$CX$_5$-(helix)-HX$_3$H] (SEQ ID NO: 20).

In one embodiment of any aspect described herein, in the synTF described or the ZF-containing fusion protein described herein, the effector domain is a transcription activating domain or a transcription repressor domain. For example, the effector domain is selected from the group consisting of a Herpes Simplex Virus Protein 16 (VP16) activation domain; an activation domain consisting of four tandem copies of VP16, a VP64 activation domain; a p65 activation domain of NFκB; an Epstein-Barr virus R transactivator (Rta) activation domain; a tripartite activator consisting of the VP64, the p65, and the Rta activation domains, the tripartite activator is known as a VPR activation domain; a histone acetyltransferase (HAT) core domain of the human E1A-associated protein p300, known as a p300 HAT core activation domain; a Krüppel associated box (KRAB)

repression domain; a Repressor Element Silencing Transcription Factor (REST) repression domain; a WRPW motif of the hairy-related basic helix-loop-helix repressor proteins, the motif is known as a WRPW repression domain; a DNA (cytosine-5)-methyltransferase 3B (DNMT3B) repression domain; and an HP1 alpha chromoshadow repression domain.

In another embodiment of any aspect described herein, in the synTF described or the ZF-containing fusion protein described herein, the effector domain is an epigenetic effector domain. For example, at least one ZF protein domain is fused to one or more chromatin regulating enzymes that (1) catalyze chemical modifications of DNA or histone residues (e.g. DNA methyltransferases, histone methyltransferases, histone acetyltransferases) or (2) remove chemical modifications (e.g. DNA demethylases, DNA di-oxygenases, DNA hydroxylases, histone demethylases, histone deacetylases). For example, a DNA methyltransferase DNMT (DNMT1, DNMT3) catalyzes the transfer of methyl group to cytosine, which typically results in transcriptional repression through the recruitment of repressive regulatory proteins. Another example is CBP/p300 histone acetyltransferase, which is typically associated with transcriptional activation through the interactions with multiple transcription factors. Related epigenetic effector domains associated with the deposition of biochemical marks on DNA or histone residue(s) include HAT1, GCN5, PCAF, MLL, SET, DOT1, SUV39H, G9a, KAT2A/B and EZH1/2. Related epigenetic effector domains associated with the removal of biochemical marks from DNA or histone residue(s) include TET1/2, SIRT family, LSD1, and KDM family.

In some embodiments of any aspect described herein, in the synTF described or the ZF-containing fusion protein described herein, all the helices within a ZFA are linked by peptide linkers ($L_2$) having four to six amino acid residues.

In some embodiments of any aspect described herein, in the synTF described or the ZF-containing fusion protein described herein, all the helices within an individual ZFA are linked by rigid peptide linkers such as TGEKP (SEQ ID NO: 2) or TGSKP (SEQ ID NO: 92) or TGQKP (SEQ ID NO: 93) or TGGKP (SEQ ID NO: 94). The rigid linker aids in conferring synergistic binding of the ZF motifs to its target DNA sequence.

In one embodiment of any aspect described herein, in the synTF described or the ZF containing fusion protein described herein, the ($L_1$) or ($L_2$) is a flexible linker. Non-limiting examples include: TGSQKP (SEQ ID NO: 3) and TGGGEKP (SEQ ID NO: 1). In one embodiment, the linker flexible peptide is 1-20 amino acids long. The flexible linker aid in weakening cooperativity between adjacent ZF motifs.

In one embodiment of any aspect described herein, in the synTF described or the ZF containing fusion protein described herein, the (L1) or (L2) is a rigid linker. Non-limiting examples include: TGEKP (SEQ ID NO: 2), TGSKP (SEQ ID NO: 92), TGQKP (SEQ ID NO: 93) and TGGKP (SEQ ID NO: 94).

In some embodiments of any aspect described herein, in the synTF described or the ZF containing fusion protein described herein, where there are two or more ZFAs, the individual ZFAs are linked by flexible peptide linkers, such as TGSQKP (SEQ ID NO: 3). In another embodiment, the ZFAs are linked by chemical crosslinkers. Chemical crosslinkers are known in the art.

In some embodiments of any aspect described herein, in the synTF described or the ZF containing fusion protein described herein, all the helices within an individual ZFA are linked by a combination of rigid peptide linkers and flexible peptide linkers. See FIG. 5 for examples of rigid peptide linkers and flexible peptide linkers in a single ZFA. In FIG. 5, the rigid peptide linkers and flexible peptide linkers are used alternatingly to connect the fingers.

Additionally, provided herein, in some aspects, are compositions comprising any one or more of the engineered, ZF-containing synthetic transcription factors (synTFs) described herein or the ZF containing fusion protein described herein, the synTF comprising a DNA binding zinc finger containing protein domain (ZF protein domain) and an effector domain, or comprising a ZF protein domain, an effector domain, and a ligand binding domain, or comprising a ZF protein domain and a ligand binding domain or a dimerization domain, wherein the ZF protein domain comprises at least one ZFA.

In one embodiment of the synTF or compositions described, the synTF has a formula I: [DNA-binding zinc finger protein domain]- [effector domain]. In one embodiment of the synTF or compositions described, the synTF has a formula IV: [effector domain]-[DNA-binding zinc finger protein domain].

In one embodiment of the synTF, or the ZF-containing fusion protein described herein, or compositions described, the at least one ZFA therein comprises, consists of, or consist essentially of a sequence: N'-[(formula II)-$L_2$]$_{6-8}$-C' wherein the formula II is [$X_{0-3}CX_{1-5}CX_{2-7}$-(helix)-$HX_{3-6}H$] (SEQ ID NO: 19), wherein X is any amino acid, the subscript numbers indicate the possible number of amino acid residues, C is cysteine, H is histidine, and (helix) is a-six contiguous amino acid residue peptide that forms a short alpha helix. In one embodiment of the synTF, the at least one ZFA therein comprises, consists of, or consist essentially of a sequence: N'-[(formula III)-$L_2$]$_{6-8}$-C' wherein the formula III is [$X_3CX_2CX_5$-(helix)-$HX_3H$] (SEQ ID NO: 20), wherein X is any amino acid, the subscript numbers indicate the possible number of amino acid residues, C is cysteine, H is histidine, and (helix) is a-six contiguous amino acid residue peptide that forms a short alpha helix.

In one embodiment of the synTF, or the ZF-containing fusion protein described herein, or compositions described, the at least one ZFA therein targets (ie. binds and interact with) a target DNA sequence selected from Target 1-11.

In one embodiment of the synTF, or the ZF-containing fusion protein described herein, or compositions described, the at least one ZFA therein comprises, consists of, or consist essentially of a ZFA helix combo selected from the group consisting of ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1 disclosed herein.

In one embodiment of the synTF, or the ZF-containing fusion protein described herein, or compositions described, the at least one ZFA therein comprises, consists of, or consist essentially of the ZFA helix combo selected from one of the ZFA helix combo Groups 1-11 disclosed herein.

In one embodiment of the synTF, or the ZF-containing fusion protein described herein, or compositions described, the at least one ZFA therein comprises, consists of, or consist essentially of the ZF motif helices selected from the six contiguous amino acid residue peptide sequences disclosed in one of the following Groups 1-11.

In one embodiment of the synTF, or the ZF-containing fusion protein described herein, or compositions described, the at least one ZFA therein comprises, consists of, or consist essentially of the ZFA helix combo, ZF 1-3: EEANLRR (SEQ ID NO: 29), DHSSLKR (SEQ ID NO: 30), QSANLLR (SEQ ID NO: 24), DPSSLKR (SEQ ID NO: 25), QQTNLTR (SEQ ID NO: 26), DATQLVR (SEQ ID NO: 27) from Group 1, and the at least one ZFA specifically binds the DNA sequence Target 1: 5' C GTC GAA GTC GAA GTC GAC C 3' (SEQ. ID. NO: 81).

In one embodiment of the synTF, or the ZF-containing fusion protein described herein, or compositions described, the at least one ZFA therein comprises, consists of, or consist essentially of the ZFA helix combo, ZF 1-1, ZF 1-2, ZF 1-3, ZF 1-4, ZF 1-5, ZF 1-6, ZF 1-7, or ZF 1-8 selected from Group 1 ZFA helix combo, and the at least one ZFA specifically binds the DNA sequence Target 1: 5' C GTC GAA GTC GAA GTC GAC C 3' (SEQ. ID. NO: 81).

In one embodiment of the synTF, or the ZF-containing fusion protein described herein, or compositions described, the at least one ZFA therein comprises, consists of, or consist essentially of the Zf motif helices selected from helices disclosed in Group 1, and the at least one ZFA specifically binds the DNA sequence Target 1: 5' C GTC GAA GTC GAA GTC GAC C 3' (SEQ. ID. NO: 81).

In one embodiment of the synTF, or the ZF-containing fusion protein described herein, or compositions described, the at least one ZFA therein comprises, consists of, or consist essentially of the ZFA helix combo, ZF 2-6: QKQALTR (SEQ ID NO: 37), DRGNLTR, (SEQ ID NO: 38) RSHDLTR (SEQ ID NO: 33), HKSSLTR (SEQ ID NO: 34), EKQNLAR (SEQ ID NO: 48), DPSNLRR (SEQ ID NO: 49) from Group 2, and the at least one ZFA specifically binds the DNA sequence Target 2: 5' G GAC GAC GTT ACG GAC GTA C 3' (SEQ. ID. NO: 82).

In one embodiment of the synTF, or the ZF-containing fusion protein described herein, or compositions described, the at least one ZFA therein comprises, consists of, or consist essentially of the ZFA helix combo, ZF 2-1, ZF 2-2, ZF 2-3, ZF 2-4, ZF 2-5, ZF 2-6, ZF 2-7, or ZF 2-8 selected from Group 2 ZFA helix combo, and the at least one ZFA specifically binds the DNA sequence Target 2: 5' G GAC GAC GTT ACG GAC GTA C 3' (SEQ. ID. NO: 82).

In one embodiment of the synTF, or the ZF-containing fusion protein described herein, or compositions described, the at least one ZFA therein comprises, consists of, or consist essentially of the ZF motif helices selected from the helices disclosed in Group 2, and the at least one ZFA specifically binds the DNA sequence Target 2: 5' G GAC GAC GTT ACG GAC GTA C 3' (SEQ. ID. NO: 82).

In one embodiment of the synTF, or the ZF-containing fusion protein described herein, or compositions described, the at least one ZFA therein comprises, consists of, or consist essentially of the ZFA helix combo, ZF 3-5: QRSSLVR (SEQ ID NO: 31), DKSVLAR (SEQ ID NO: 40), QRSSLVR (SEQ ID NO: 31), QTNNLGR (SEQ ID NO: 41), THAVLTR (SEQ ID NO: 42), DRGNLTR (SEQ ID NO: 38) from Group 3, and the at least one ZFA specifically binds the DNA sequence Target 3: 5' A GAC GTC GAA GTA GCC GTA G 3' (SEQ. ID. NO: 83).

In one embodiment of the synTF, or the ZF-containing fusion protein described herein, or compositions described, the at least one ZFA therein comprises, consists of, or consist essentially of the ZFA helix combo, ZF 3-1, ZF 3-2, ZF 3-3, ZF 3-4, ZF 3-5, ZF 3-6, ZF 3-7, or ZF 3-8, selected from Group 3 ZFA helix combo, and the at least one ZFA specifically binds the DNA sequence Target 3: 5' A GAC GTC GAA GTA GCC GTA G 3' (SEQ. ID. NO: 83).

In one embodiment of the synTF, or the ZF-containing fusion protein described herein, or compositions described, the at least one ZFA therein comprises, consists of, or consist essentially of the ZF motif helices disclosed in Group 3, and the at least one ZFA specifically binds the DNA sequence Target 3: 5' A GAC GTC GAA GTA GCC GTA G 3' (SEQ. ID. NO: 83).

In one embodiment of the synTF, or the ZF-containing fusion protein described herein or compositions described, the at least one ZFA therein comprises, consists of, or consist essentially of the ZFA helix combo, ZF 4-8: QQTNLTR (SEQ ID NO: 26), QSTSLQR (SEQ ID NO: 51), VRHNLTR (SEQ ID NO: 47), DHSNLSR (SEQ ID NO: 50), EKQNLAR (SEQ ID NO: 48), DPSNLRR (SEQ ID NO: 49) from Group 4, and the at least one ZFA specifically binds the DNA sequence Target 4: 5' G GAC GAC GCC GAT GTA GAA G 3' (SEQ. ID. NO: 84).

In one embodiment of the synTF, or the ZF-containing fusion protein described herein, or compositions described, the at least one ZFA therein comprises, consists of, or consist essentially of the ZFA helix combo, ZF 4-1, ZF 4-2, ZF 4-3, ZF 4-4, ZF 4-5, ZF 4-6, ZF 4-7, or ZF 4-8, selected from Group 4 ZFA helix combo, and the at least one ZFA specifically binds the DNA sequence Target 4: 5' G GAC GAC GCC GAT GTA GAA G 3' (SEQ. ID. NO: 84).

In one embodiment of the synTF, or the ZF-containing fusion protein described herein, or compositions described, the at least one ZFA therein comprises, consists of, or consist essentially of the ZF motif helices selected from the helices disclosed in Group 4, and the at least one ZFA specifically binds the DNA sequence Target 4: 5' G GAC GAC GCC GAT GTA GAA G 3' (SEQ. ID. NO: 84).

In one embodiment of the synTF, or the ZF-containing fusion protein described herein, or compositions described, the at least one ZFA therein comprises, consists of, or consist essentially of the ZFA helix combo, ZF 5-7: NMSNLTR (SEQ ID NO: 52), DRSVLRR (SEQ ID NO: 53), DPSNLAR (SEQ ID NO: 59), DRSSLRR (SEQ ID NO: 55), QSGTLHR (SEQ ID NO: 56), QSGTLHR (SEQ ID NO: 56) from Group 5, and the at least one ZFA specifically binds the DNA sequence Target 5: 5' T GAA GCA GTC GAC GCC GAA G 3' (SEQ. ID. NO: 85).

In one embodiment of the synTF, or the ZF-containing fusion protein described herein, or compositions described, the at least one ZFA therein comprises, consists of, or consist essentially of the ZFA helix combo, ZF 5-1, ZF 5-2, ZF 5-3, ZF 5-4, ZF 5-5, ZF 5-6, ZF 5-7, or ZF 5-8, selected from Group 5 ZFA helix combo, and the at least one ZFA specifically binds the DNA sequence Target 5: 5' T GAA GCA GTC GAC GCC GAA G 3' (SEQ. ID. NO: 85).

In one embodiment of the synTF, or the ZF-containing fusion protein described herein, or compositions described, the at least one ZFA therein comprises, consists of, or consist essentially of the ZF motif helices selected from the helices disclosed in Group 5, and the at least one ZFA specifically binds the DNA sequence Target 5: 5' T GAA GCA GTC GAC GCC GAA G 3' (SEQ. ID. NO: 85).

In one embodiment of the synTF, or the ZF-containing fusion protein described herein, or compositions described, the at least one ZFA therein comprises, consists of, or consist essentially of the ZFA helix combo, ZF 6-4: QQTNLTR (SEQ ID NO: 26), QKANLGV (SEQ ID NO: 62), DHSSLKR (SEQ ID NO: 30), RADMLRR (SEQ ID NO: 61), EKQNLAR (SEQ ID NO: 48), DPSNLRR (SEQ ID NO: 49) from Group 6, and the at least one ZFA specifically binds the DNA sequence Target 6: 5' G GAC GAC GCG GTC TAA GAA G 3' (SEQ. ID. NO: 86).

In one embodiment of the synTF, or the ZF-containing fusion protein described herein, or compositions described, the at least one ZFA therein comprises, consists of, or consist essentially of the ZFA helix combo, ZF 6-1, ZF 6-2, ZF 6-3, ZF 6-4, ZF 6-5, ZF 6-6, ZF 6-7, or ZF 6-8, selected from Group 6 ZFA helix combo, and the at least one ZFA specifically binds the DNA sequence Target 6: 5' G GAC GAC GCG GTC TAA GAA G 3' (SEQ. ID. NO: 86).

In one embodiment of the synTF, or the ZF-containing fusion protein described herein, or compositions described, the at least one ZFA therein comprises, consists of, or consist essentially of the ZF motif helices selected from the helices disclosed in Group 6, and the at least one ZFA specifically binds the DNA sequence Target 6: 5' G GAC GAC GCG GTC TAA GAA G 3' (SEQ. ID. NO: 86).

In one embodiment of the synTF, or the ZF-containing fusion protein described herein, or compositions described, the at least one ZFA therein comprises, consists of, or consist essentially of the ZFA helix combo, ZF 7-3: QRSSLVR (SEQ ID NO: 31), QRGNLNM (SEQ ID NO: 64), RRQELTR (SEQ ID NO: 69), DHSSLKR (SEQ ID NO: 30), RQDNLGR (SEQ ID NO: 66), DGGNLGR (SEQ ID NO: 67) from Group 7, and the at least one ZFA specifically binds the DNA sequence Target 7: 5' C GAC GAG GTC GCA TAA GTA G 3' (SEQ. ID. NO: 87).

In one embodiment of the synTF, or the ZF-containing fusion protein described herein, or compositions described, the at least one ZFA therein comprises, consists of, or consist essentially of the ZFA helix combo, ZF 7-1, ZF 7-2, ZF 7-3, ZF 7-4, ZF 7-5, ZF 7-6, ZF 7-7, or ZF 7-8, selected from Group 7 ZFA helix combo, and the at least one ZFA specifically binds the DNA sequence Target 7: 5' C GAC GAG GTC GCA TAA GTA G 3' (SEQ. ID. NO: 87).

In one embodiment of the synTF, or the ZF-containing fusion protein described herein, or compositions described, the at least one ZFA therein comprises, consists of, or consist essentially of the ZF motif helices selected the helices disclosed in Group 7, and the at least one ZFA specifically binds the DNA sequence Target 7: 5' C GAC GAG GTC GCA TAA GTA G 3' (SEQ. ID. NO: 87).

In one embodiment of the synTF, or the ZF-containing fusion protein described herein, or compositions described, the at least one ZFA therein comprises, consists of, or consist essentially of the ZFA helix combo, ZF 8-1: QASNLTR (SEQ ID NO: 70), DHSSLKR (SEQ ID NO: 30), RAHNLLL (SEQ ID NO: 71), QRSSLVR (SEQ ID NO: 31), QSTTLKR (SEQ ID NO: 72), DPSNLRR (SEQ ID NO: 49), from Group 8, and the at least one ZFA specifically binds the DNA sequence Target 8: 5' A GAC GCA GTA TAG GTC GAA C 3' (SEQ. ID. NO: 88).

In one embodiment of the synTF, or the ZF-containing fusion protein described herein, or compositions described, the at least one ZFA therein comprises, consists of, or consist essentially of the ZFA helix combo, ZF 8-1, ZF 8-2, ZF 8-3, or ZF 8-4, selected from Group 8 ZFA helix combo, and the at least one ZFA specifically binds the DNA sequence Target 8: 5' A GAC GCA GTA TAG GTC GAA C 3' (SEQ. ID. NO: 88).

In one embodiment of the synTF, or the ZF-containing fusion protein described herein, or compositions described, the at least one ZFA therein comprises, consists of, or consist essentially of the ZF motif helices selected from the helices disclosed in Group 8, and the at least one ZFA specifically binds the DNA sequence Target 8: 5' A GAC GCA GTA TAG GTC GAA C 3' (SEQ. ID. NO: 88).

In one embodiment of the synTF, or the ZF-containing fusion protein described herein, or compositions described, the at least one ZFA therein comprises, consists of, or consist essentially of the ZFA helix combo, ZF 9-2: EKQNLAR (SEQ ID NO: 48), DPSNLRR (SEQ ID NO: 49), RAHNLLL (SEQ ID NO: 71), QRSSLVR (SEQ ID NO: 31), QSTTLKR (SEQ ID NO: 72), DPSNLRR (SEQ ID NO: 49) from Group 9, and the at least one ZFA specifically binds the DNA sequence Target 9: 5' A GAC GCA GTA TAG GAC GAC G 3' (SEQ. ID. NO: 89).

In one embodiment of the synTF, or the ZF-containing fusion protein described herein, or compositions described, the at least one ZFA therein comprises, consists of, or consist essentially of the ZFA helix combo, ZF 9-1, ZF 9-2, ZF 9-3, or ZF 9-4, selected from Group 9 ZFA helix combo, and the at least one ZFA specifically binds the DNA sequence Target 9: 5' A GAC GCA GTA TAG GAC GAC G 3' (SEQ. ID. NO: 89).

In one embodiment of the synTF, or the ZF-containing fusion protein described herein, or compositions described, the at least one ZFA therein comprises, consists of, or consist essentially of the ZF motif helices selected from the helices disclosed in Group 9, and the at least one ZFA specifically binds the DNA sequence Target 9: 5' A GAC GCA GTA TAG GAC GAC G 3' (SEQ. ID. NO: 89).

In one embodiment of the synTF, or the ZF-containing fusion protein described herein, or compositions described, the at least one ZFA therein comprises, consists of, or consist essentially of the ZFA helix combo, ZF 10-1: RRHGLDR (SEQ ID NO: 75), DHSSLKR (SEQ ID NO: 30), VRHNLTR (SEQ ID NO: 47), DHSNLSR (SEQ ID NO: 50), QRSSLVR (SEQ ID NO: 31), ESGHLKR (SEQ ID NO: 76) from Group 10, and the at least one ZFA specifically binds the DNA sequence Target 10: 5' C GGC GTA GCC GAT GTC GCG C 3' (SEQ. ID. NO: 90).

In one embodiment of the synTF, or the ZF-containing fusion protein described herein, or compositions described, the at least one ZFA therein comprises, consists of, or consist essentially of the ZFA helix combo, ZF 11-1: QLSNLTR (SEQ ID NO: 77), DRSSLKR (SEQ ID NO: 78), QRSSLVR (SEQ ID NO: 31), RLDMLAR (SEQ ID NO: 63), VRHSLTR (SEQ ID NO: 79), ESGALRR (SEQ ID NO: 80), from Group 11, and the at least one ZFA specifically binds the DNA sequence Target 11: 5' G GTC GTT GCG GTA GTC GAA G 3' (SEQ. ID. NO: 91).

In one embodiment of the synTF, or the ZF-containing fusion protein described herein, or compositions described, the at least one ZFA therein comprises, consists of, or consist essentially of a sequence: N'-PGERPFQCRICMRNFS-(Helix 1)-HTRTHTGEKPFQCRICMRNFS-(Helix 2)-HLRTHTGSQK PFQCRICMRNFS-(Helix 3)-HTRTHTGEK PFQCRICMRNFS-(Helix 4)-HLRTHTGSQKPFQCRICMRNFS-(Helix 5)-HTRTHTGEK PFQCRICMRNFS-(Helix 6)-HLRTHLR-C' (SEQ ID NO: 21), wherein the (Helix) is a-six contiguous amino acid residue peptide that forms a short alpha helix. In one embodiment, the (Helix) is selected from those helices disclosed in groups 1-11.

In one embodiment of the synTF, or the ZF-containing fusion protein described herein, or compositions described, the at least one ZFA therein of the ZF protein domain is a six-finger ZFA, a seven-finger ZFA or an eight-finger ZFA. Where there are more than one ZFA making up the ZF protein domain, the ZF protein domain may comprise of a combination of a six-finger ZFA, a seven-finger ZFA and an eight-finger ZFA, or comprise of all six-finger ZFAs, or comprise of all seven-finger ZFAs, or comprise of all eight-finger ZFAs.

In one embodiment of the synTF, or the ZF-containing fusion protein described herein, or compositions described, the effector domain is located at the N'-terminus of the synTF, ie., attached to the N-terminus of the ZF protein domain. In another embodiment, the effector domain is located at the C'-terminus of the synTF, ie., attached to the C-terminus of the ZF protein domain.

In one embodiment of the synTF, or the ZF-containing fusion protein described herein, or compositions described, the ligand binding domain or the protein interaction domain/dimerization domain is located at the N'-terminus of the ZF protein domain. In another embodiment, the ligand binding domain or the protein interaction domain/dimerization domain is located at the C'-terminus of the ZF protein domain.

In one embodiment of the synTF, or the ZF-containing fusion protein described herein, or compositions described, the effector domain is a transcription activating domain or a transcription repressor domain or an epigenetic effector domain.

In one embodiment of the synTF, or the ZF-containing fusion protein described herein, or compositions described, the effector domain of the synTF is the VP64 activation domain comprising the sequence: GRADALDDFDLDM-LGSDALDDFDLDMLGSDALDDFDLDMLGSDALDD-FDLDML (SEQ. ID. NO: 95).

In one embodiment of the synTF, or the ZF-containing fusion protein described herein, or compositions described, the effector domain of the synTF is the p65 activation domain of NFκB comprising the sequence:

(SEQ. ID. NO: 96)
DEFPTMVFPSGQISQASALAPAPPQVLPQAPAPAPAPAMVSALAQAPAPV

PVLAPGPPQAVAPPAPKPTQAGEGTLSEALLQLQFDDEDLGALLGNSTDP

AVFTDLASVDNSEFQQLLNQGIPVAPHTTEPMLMEYPEAITRLVTGAQRP

PDPAPAPLGAPGLPNGLLSGDEDFSSIADMDFSALLSQISS.

In one embodiment of the synTF, or the ZF-containing fusion protein described herein, or compositions described, the effector domain of the synTF is the p300 HAT Core activation domain comprising the sequence: IFKPEEL-RQALMPTLEALYRQDPESLPFRQPVDPQLLGIPDYF-DIVKSPMDLSTIKRKLDTGQYQE PWQYVDDIWLMF-NNAWLYNRKTSRVYKYCSKLSEVFEQEIDPVMQSL-GYCCGRKLEFSPQTLC CYGKQLCTIPRDATYYSY-QNRYHFCEKCFNEIQGESVSLGDDPSQPQTTINKEQF-SKRKNDTLDP ELFVECTECGRKMHQICVLHHEIIW-PAGFVCDGCLKKSARTRKENKFSAKRLPSTRLGTF-LENRV NDFLRRQNHPESGEVTVRVVHASDKTVEVK-PGMKARFVDSGEMAESFPYRTKALFAFEEIDGV DLCFFGMHVQEYGSDCPPPNQRRVYISYLDSVHF-FRPKCLRTAVYHEILIGYLEYVKKLGYTTG HIWACPPSEGDDYIFHCHPPDQKIPKPKRLQEWYK-KMLDKAVSERIVHDYKDIFKQATEDRLTS AKELPY-FEGDFWPNVLEESIKELEQEEEERKREENTSNESTD-VTKGDSKNAKKKNNKKTSKNKS SLSRGNK-KKPGMPNVSNDLSQKLYATMEKHKEVFFVIRLIAG-PAANSLPPIVDPDPLIPCDLMDG RDAFLTLARD-KHLEFSSLRRAQWSTMCMLVELHTQSQD (SEQ. ID. NO: 147). The nucleic acid sequence is known in the art and is SEQ. ID. NO: 131 of this present patent application.

In one embodiment of the synTF, or the ZF-containing fusion protein described herein, or compositions described, the effector domain of the synTF is the KRAB repressive domain comprising the sequence:

(SEQ. ID. NO: 97)
MDAKSLTAWSRTLVTFKDVFVDFTREEWKLLDTAQQILYRNVMLENYKNL
VSLGYQLTKPDVILRLEKGEEPWLVEREIHQETHPDSETAFEIKSSV.

In one embodiment of the synTF, or the ZF-containing fusion protein described herein, or compositions described, the effector domain of the synTF is the HP1 alpha chromo-shadow repressive domain comprising the sequence:

(SEQ. ID. NO: 98)
MKKREQSNDIARGFERGLEPEKIIGATDSCGDLMFLMKWKDTDEADLVL
AKEANVKCPQIVIAFYEERLTWHAYPEDAENKEK.

In one embodiment of the synTF, or the ZF-containing fusion protein described herein, or compositions described, the effector domain of the synTF is the DNMT3B repression domain comprising the sequence: MKGDTRHLNGEED-AGGREDSILVNGACSDQSSDSPPILEAIRTPEIR-GRRSSSRLSKREVSSLLSYT QDLTGDGDGEDGDGS-DTPVMPKLFRETRTRSESPAVRTRNNNSVSSRERHRP-SPRSTRGRQGRN HVDESPVEFPATRSLRRRAT-ASAGTPWPSPPSSYLTIDLTDDTEDTHGTPQSSSTP-YARLAQDSQQ GGMESPQVEADSGDGDSSEYQDG-KEFGIGDLVWGKIKGFSWWPAMVVSWKATSKR-QAMSGM RWVQWFGDGKFSEVSADKLVALGLF-SQHFNLATFNKLVSYRKAMYHALEKARVRAGKT-FPSS PGDSLEDQLKPMLEWAHGGFKPTGIEGLK-PNNTQPENKTRRRTADDSATSDYCPAPKRLKTNC YNNGKDRGDEDQSREQMASDVANNKSSLEDG-CLSCGRKNPVSFHPLFEGGLCQTCRDRFLELF YMYDDDGYQSYCTVCCEGRELLLCSNTSC-CRCFCVECLEVLVGTGTAAEAKLQEPWSCYMCLP QRCHGVLRRRKDWNVRLQAFFTSDTGLEYEAPKLY-PAIPAARRRPIRVLSLFDGIATGYLVLKEL GIKVGKY-VASEVCEESIAVGTVKHEGNIKYVNDVRNITKKNIEE-WGPFDLVIGGSPCNDLSNVNP ARKGLYEGTGR-LFFEFYHLLNYSRPKEGDDRPFFWMFENVVAMK-VGDKRDISRFLECNPVMID AIKVSAAHRARYFWGN-LPGMNRPVIASKNDKLELQDCLEYNRIAKDLWLS-CALHRRVQHGPW CPPEAAGKVLERACHPTPLRPSEGLLCM (SEQ. ID. NO: 148). The nucleic acid sequence is known in the art and is SEQ. ID. NO: 132 of this present patent application.

FIGS. 6A-6D show the general modular design of an engineered synTFs having a ZFA (having a six ZF motif) covalently linked to an effector domain such as a VP64 activation (FIG. 6A), a KRAB repressive domain (FIG. 6B), a HP1 repressive domain (FIG. 6C), and a p65 activation domain ((FIG. 6D).

In one embodiment of the synTF, or the ZF-containing fusion protein described herein, or compositions described, where there are more than one ZFA, the ZFAs are connected covalently in tandem, N-terminus to C-terminus, into a ZFA array forming the ZF protein domain, and the ZF protein domain is covalently linked to the N-terminus or C-terminus of the effector domain.

In one embodiment of the synTF, or the ZF-containing fusion protein described herein, or compositions described, where there is only one ZFA, the ZFA is covalently linked to the N-terminus or the C-terminus of the effector domain.

In one embodiment of the synTF, or the ZF-containing fusion protein described herein, or compositions described, the ZFA(s) and the effector domain are covalently linked by peptide linkers or by chemical crosslinkers.

In one embodiment of the synTF, or the ZF-containing fusion protein described herein, or compositions described, the peptide linkers are flexible or rigid peptide linkers.

In one embodiment of the synTF, or the ZF-containing fusion protein described herein, or compositions described, the ZF motifs within a ZFA are covalently connected with peptide linkers. In one embodiment, the peptide linkers are flexible or rigid linkers. In one embodiment, a combination of flexible peptide and rigid peptide linkers are used in covalently connected the ZF motifs within a ZFA. In one embodiment, alternating flexible peptide and rigid peptide linkers are used to covalently connect the ZF motifs within a ZFA, as shown in FIGS. 5A, 5B, 6A-6D.

In one embodiment of the synTF, or the ZF-containing fusion protein described herein, or compositions described, where there are more than one ZFA in the ZF protein domain, the peptide linkers connecting the ZFAs are rigid peptide linkers. In one embodiment, these rigid peptides are about 4-6 amino acid residues long. In one embodiment, these rigid peptides are selected from the group consisting of TGEKP (SEQ ID NO: 2), TGGKP (SEQ ID NO: 94), TGSKP (SEQ ID NO: 92), TGQKP (SEQ ID NO: 93), SGEKP (SEQ ID NO: 99), SGSKP (SEQ ID NO: 100), SGQKP (SEQ ID NO: 101), and SGGKP (SEQ ID NO: 102).

In one embodiment of the synTF, or the ZF-containing fusion protein described herein, or compositions described, where there are more than one ZFA in the ZF protein domain, the peptide linkers connecting the ZFAs are flexible linkers. In one embodiment, the flexible linkers are peptide linkers. In one embodiment, the flexible peptide linkers at 1-20 amino acid residues long.

In one embodiment of the synTF, or the ZF-containing fusion protein described herein, or compositions described, where there are more than one ZFA in the ZF protein domain, the peptide linkers connecting the ZFAs are flexible peptide linkers. In one embodiment, these flexible peptides are about 1-20 amino acid residues long. In one embodiment, the flexible peptide is about 1-20 amino acid residues long. In other embodiments, the flexible peptide is about 6, about 10, about 12, about 15, about 18, and about 20 amino acid residues long.

In one embodiment of the synTF, or the ZF-containing fusion protein described herein, or compositions described, where there are more than one ZFAs and the synTF in the ZF protein domain, the peptide linker connecting the ZF protein domain to the effector domain is a flexible peptide linker. In one embodiment, the flexible peptide is about 1-20 amino acid residues long. In other embodiments, the flexible peptide is about 6, about 10, about 12, about 15, about 18, and about 20 amino acid residues long.

Additionally, provided herein, in some aspects, are nucleic acid molecules or nucleic acid sequences encoding any one or more of the engineered, ZF-containing synthetic transcription factors (synTFs) described herein or the ZF-containing fusion protein described herein.

Additionally, provided herein, in some aspects, is a vector comprising nucleic acid sequence(s) encoding any one or more of the engineered, ZF-containing synTFs described herein or the ZF containing fusion protein described herein. For example, the vector facilitate the replication of the described nucleic acid sequence(s) in a cell and also enable the expression of the described synTF from the nucleic acid sequence(s) in a cell.

Additionally, provided herein, in some aspects, is a cell carrying a vector comprising nucleic acid sequence(s) encoding any one or more of the engineered, ZF-containing synthetic transcription factors (synTFs) described herein or the ZF-containing fusion protein described herein. For example, the cell facilitate the replication of the described vector comprising the nucleic acid sequence(s) in a cell and also enable the expression of the described synTF or the ZF containing fusion protein described herein from the nucleic acid sequence(s) in a cell. In one embodiment, the vector is a lentiviral vector or an adenoviral vector or a retroviral vector.

Engineered Responsive Promoters Having the Orthogonal Target DNA

Provided herein, in some aspects, are methods and assays to identify DNA sequences for zinc finger arrays that have reduced binding potential in a host genome.

In some aspects, provided herein are methods and assays for designing and constructing 6-finger ZFA, or 7-finger ZFA, or 8-finger ZFA capable of targeting the identified DNA sequences.

In some aspects, provided herein are methods and assays for designing and constructing synthetic transcription factors (synTFs): zinc finger arrays coupled to transcriptional effector domains (including VP64, p65, KRAB and HP1).

In some aspects, provided herein are methods and assays for designing and constructing partner synthetic promoters that pairs with the previously described synTFs to form an expression system. The partner synthetic promoters comprise zinc finger binding sites of different number placed upstream of minimal core promoters (e.g., minimal CMV promoter (minCMV), minimal thymidine kinase promoter (minTK)) or constitutive promoters (e.g. CMV promoter, Ubiquitin promoter).

Provided herein is a nucleic acid sequence comprising a DNA sequence element selected from the group consisting of: Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91). These DNA sequence elements are specially designed to be orthogonal to a eukaryotic genome. The orthogonal DNA sequence elements are also referred to as "target" DNA, "target," "target" DNA sequence or "target" DNA sequence elements in the context of the synthetic transcription factor, and are used interchangeably. Moreover, these DNA sequence elements are specially designed to be recognized and bound specially by engineered synthetic transcription factors. When used together in vivo, these DNA sequence elements and their specially engineered synthetic transcription factors form the basic components of a regulatable, programmable gene expression system that allows the modulation of gene expression in vivo.

In one embodiment, this orthogonal nucleic acid sequence is part of an engineered responsive protomer or transcriptional unit, where the sequence is located upstream of the promoter sequence. Upstream as is conventionally used in the art means 5' of the promoter sequence.

In one embodiment, this orthogonal nucleic acid sequence is operably linked to the the promoter sequence to influence the transcription initiation when the orthogonal nucleic acid sequence is occupied by the described synTF having an effector domain.

Also provided herein is a vector comprising a nucleic acid sequence comprising a DNA sequence element selected from the group consisting of: Target 1: 5'-CGTCGAAGTC-GAAGTCGACC-3' (SEQ ID NO: 81), 5'-GGACGACGT-TACGGACGTAC-3' (SEQ ID NO: 82), 5'-A GACGTC-GAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91). The vector can comprise more than one of these DNA sequence elements. When there are more than one, the DNA sequence elements may be the same (ie, repeated) or different.

Additionally, provided herein is a cell comprising a vector comprising a nucleic acid sequence comprising a DNA sequence element selected from the group consisting of: Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91). The vector can comprise more than one of these DNA sequence elements. When there are more than one, the DNA sequence elements may be the same (ie, repeated) or different.

Described herein is the identification of "orthogonal" DNA target sequences and methods and assays for designing an array of ZFA, forming the ZF protein domain, which would be used in engineering the DNA binding and ZF-containing synTF described. A ZF protein domain comprises of one or a plurality of ZFA joined by a non-rigid linker (e.g., "TGGGEKP" (SEQ ID NO: 1). A ZFA is comprised of one or a plurality of ZF mofits joined by a rigid linker (e.g. "TGEKP" (SEQ ID NO: 2)) that have been pre-defined (e.g., via selection) to recognize DNA sequence elements and joined by a rigid linker.

Adjacent ZF motifs joined by rigid linkers (e.g. "TGEKP" (SEQ ID NO: 2)) have been demonstrated to have the capacity to bind their targets synergistically. In comparison, finger set's joined by flexible linkers (e.g. "TGSQKP" (SEQ ID NO: 3)) exhibit a lesser cooperativity. However, their flexibility permits greater context independence between ZFAs. Based upon this, it is inferred, without wishing to be bound or limited by theory, that the binding specificity of a ZF protein domain to be dominated by the recognition of the ZFAs for their individual ZFA specific target sites within the context permitted by the linkers joining ZFAs.

To identify orthogonal target DNA sequence element (DNA target) for the binding ZFA and ZF protein domain wherein the ZFA are designed to have reduced binding potential in a host genome, the following concepts and goals were considered: (step 1) Use ZF motifs that target DNA sequences that are known to under-represented DNA sequences in the eukaryotic host genome. Table 1 show some examples of ~6 bp (6 mers) in human genome and their respective occurrences in the human genome calculated from GRCh37. This strategy aims at decreasing the number of individual ZF locations expected to dominate high affinity interactions. It also has the benefit of generally reducing the number of regions with a high degree of overall identity. (step 2) Pick DNA target sequences that are highly distinct from genomic sequence. These would preferentially have no identical in the host genome and few sites that share a high degree of identity. (step 3) Use DNA target sequences of ZF motifs where there are more than one ZF target sequences that are positioned such that the available amino acid in the ZFA linkers specifically enforce the distances between ZF targets. This minimizes the number of binding modalities that are tolerated and intrinsically increases the overall specificity profile. For example, the inventors looked for DNA target sequences of two 2-finger ZF motifs where the respective 2-finger ZF target sequences sites are immediately adjacent to each other. Then when these two 2-finger ZF motifs are covalently conjugated with a flexible linker such as "TGSQKP," (SEQ ID NO: 3) the flexible linker would allow the two 2-finger ZF motifs to bind their respective ZF DNA target sequence that are immediately adjacent to each other. Alternatively, the inventors looked for DNA target sequences of two 2-finger ZF motifs where the respective 2-finger ZF target sequences sites are separated by a single base. Here, when these two 2-finger ZF motifs are covalently conjugated with an amino acid linker "TGGGGSQKP," (SEQ ID NO: 103) this linker would allow the two 2-finger ZF motifs to bind their respective ZF DNA target sequence that are either adjacent or separated by a single base pair.

The inventors have a library of 2-finger ZF motifs, which have been pre-selected to bind ~6 bp DNA sequences, these are the target DNA sequences, target with reference to the ZF motifs binding. These are a priori known. Then, the inventors screen and identify which of these known target sequences for these 2-finger units are the most underrepresented in the host genome. The inventors then combined three of the identified and selected ~6 bp target sites that are the most underrepresented in the genome to arrive at a most "orthogonal" 18-bp DNA sequences. The combination of these underrepresented "2-finger unit" sites would be predicted to (a) not occur in the host genome and (b) have the least possibility of having sub-sites lead to functional binding (i.e. most "distant"). The inventors then verified that these artificially created ~18-20 bp target sites do not occur in the genome by scanning them against the genome sequences.

In some embodiments of the aspects described herein to identify DNA sequences for zinc finger arrays designed to have reduced binding potential in a host genome, the following method was employed: Target sequence are defined as 18 bp. Targets are represented by three 2-finger units (each 2-finger unit recognizes ~6 bp), meaning targets are made up of three ~6 bp (6 mers) DNA sequences. The three ~6 bp for the three 2-finger units are immediately adjacent to each other, forming the ~18 bp. Human genome is screened to determine the number of times each of the 6 bp DNA sequences for the respective 2-finger units occurs. The ones with rare or no occurrences are selected and used for combining together to form the ~18 bp DNA target sequences for a corresponding three 2-finger units that make up a ZFA that would bind the ~18 bp. All potential 18 bp sequences that can be made from these 6 bp sequence were generated.

In some embodiments, to pare down this large list while simultaneously enriching for sequences highly amenable to zinc finger binding/design, the list was filtered to meet one or more of the following conditions:

a) No single nucleotide could account for more than 35% of the sequence.

b) Sequence start with a G c) Sequence does not end with two pyrimidines d) The sequence must have no homo-polymers of 4 or more nucleotides e) Not stretch of TTT f) Sequence comprise at least 5 GNNs individual zinc finger targets g) Sequence comprises at least 10 purines.

Human genome is screened to determine the number of times each 6 bp site occurs.

All 18 bp DNA sequences from step 2 were scored according to the product of the propensity of the three 6 bp ZF motif target sites to occur in the human genome.

An initial set of sequences with low probability scores of occurring naturally were selected also considering complexity and distinctness from each other. This was done by ranking the sites according to their score and the manually screening the list starting with sequences with the lowest score.

For the 18 bp sequences selected in the previous step, a comprehensive analysis was done for each site against the human genome to identify all sites with an identity of 14-18 with the targets.

Sequences were expertly selected such that they had no exact matches or off by is and greatly fewer off by 2, 3 and 4 than other sites in the list.

Zinc fingers were designed according to established guidelines. For example, to optimize activity variants can be designed where the residues shown to make non-specific contacts with the DNA phosphate backbone could be altered to eliminate these non-specific interactions.

The orthogonal DNA target sequences were used as the starting set of eleven 20-bp target sites (6 triplets recognized by ZF helices+2 bp flanking) that were subsequently used to create responsive promoters. Accordingly, provided herein, in some aspects, are engineered responsive promoter elements comprising at least one target DNA sequence element selected from the group consisting of Target 1: 5'-CGTCGAAGTCGAAGTCGACC-3' (SEQ ID NO: 81), 5'-GGACGACGTT ACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91).

Engineered responsive promoter elements are regulatory sequence within or directly upstream of a promoter that is recognized by a transcriptional regulator (in this case our synTF).

Also provided herein, in some aspects, are engineered promoter comprising (a) at least one target DNA sequence element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91) and (b) a promoter.

In one embodiment of the engineered responsive promoter element or engineered promoter described, there is more than one target DNA sequence element. For example, there can be two, three, four, five, six, seven, eight, nine and up to ten target DNA sequence elements. The multiple target DNA sequence elements can be the same or different in the engineered responsive promoter element or engineered promoter.

In one embodiment of the engineered responsive promoter element or engineered promoter, where there are more than one target DNA sequence elements, the target DNA sequence elements are separated by nucleic acid spacers. In some embodiments, the nucleic acid spacers are about 4-10 bps long. In one embodiment, the nucleic acid spacers are no more than 6 bps long.

In one embodiment of the engineered responsive promoter described, the target DNA sequence element(s) is/are located and attached at the 5' end of promoter.

In one embodiment of the engineered responsive promoter described, the target DNA sequence element(s) and the minimum promoter are are separated by nucleic acid spacers. In some embodiments, the nucleic acid spacers are about 4-10 bps long. In one embodiment, the nucleic acid spacers are no more than 6 bps long.

FIG. 4A shows two embodiments of engineered responsive promoter elements comprising target DNA sequence elements (ie. 1× promoter), the top engineered responsive promoter element has one target DNA sequence element, and bottom engineered responsive promoter element has four target DNA sequence element (ie. 4× promoter). The described eleven 20-bp target DNA sequence element can be incorporated into responsive promoter architectures, and different DNA sequence elements can be used incorporated multiple times when there are more than one DNA sequence element in the engineered responsive promoter elements.

FIG. 4B shows an engineered responsive promoter comprising eight target DNA sequence elements and a full-length promoter. Such a promoter is useful for gene repression.

FIG. 4C shows an engineered responsive promoter comprising five target DNA sequence elements and a minimal promoter.

Also provided herein, in some aspects, are synthetic transcription unit comprising (a) at least one target DNA sequence element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91), (b) a promoter, and (c) at least a gene of interest (GOI), the least one target DNA sequence element is operably linked upstream of the promoter which is itself operably linked upstream of the (GOI).

In some embodiments of engineered responsive promoter described, the promoter described herein can be a full-length functional promoter or a minimal promoter having very limited or no transcription initiation therefrom absent the assistance of added transcription factors. Non-limiting examples of full-length functional promoters include CMV, UBCbc, EF1 alpha, SV40, PGK, CAG, beta actin, U6 and H1. Non-limiting examples of minimal promoters include minimal CMV, and minimal TK and any synthetically designed promoters composed of core minimal promoter elements and regulating enhancer elements (e.g. HSE, TRE, NFAT/AP-1 binding elements).

Also provided herein is a vector comprising an engineered responsive promoter elements comprising at least one target DNA sequence element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91).

Additionally, provided herein is a cell comprising a vector comprising an engineered responsive promoter elements comprising at least one target DNA sequence element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91).

Also provided herein is a vector comprising an engineered promoter comprising (a) at least one target DNA sequence promoter element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91) and (b) a promoter, wherein the at least one target DNA sequence element is operably linked to the promoter.

Additionally, provided herein is a cell comprising a vector comprising an engineered promoter comprising (a) at least one target DNA sequence element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91) and (b) a promoter, wherein the at least one target DNA sequence element is operably linked to the promoter.

Also provided herein is a vector comprising a synthetic transcription unit comprising (a) at least one target DNA sequence element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91), (b) a promoter, and (c) at least a gene of interest (GOI), the least one target DNA sequence element is operably linked upstream to the promoter, and wherein the promoter is operably linked upstream to the GOI.

Additionally, provided herein is a cell comprising a vector comprising a synthetic transcription unit comprising (a) at least one target DNA sequence element selected from the group consisting of Target 1: 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91), (b) a promoter, and (c) at least a gene of interest (GOI), the least one target DNA sequence element is operably linked upstream to the promoter, and wherein the promoter is operably linked upstream to the GOI.

Engineered Regulatable Gene Expression Systems and Uses

Provided herein, in some aspects, is an engineered gene expression system for in vivo or in vitro regulation of the expression of an exogenous gene, comprising: a synthetic transcription factor (synTF) described herein and an engineered promoter described herein. The synTF comprises one or more Zinc-finger domain and an effector domain, wherein the Zn-finger domain is located N- or C-terminus of the effector domain. The engineered promoter comprises one or more orthogonal DNA target sequences and a promoter sequence described herein. The one or more orthogonal DNA target sequences are operably linked to the promoter. The orthogonal DNA target sequences enable the promoter to be responsive to the synTF. When the engineered promoter is operably linked linked upstream of a sequence coding a protein, (e.g. a gene), a synthetic transcription unit is thus formed. The Zn-finger domain of synTF are designed to binds the one or more orthogonal DNA target sequences of the synthetic transcription unit to modulate gene transcription and thus gene expression, namely, initiate gene transcription or repress gene transcription. The Zn-finger domain in the synTF consists a plurality of ZFA and the engineered promoter can contain a plurality of orthogonal DNA target sequences. A ZFA within the ZF protein domain of the synTF and a orthologus DNA target sequence form a specific interaction pairs such that the ZFA only binds a specific orthogonal DNA target sequence and not other orthologus DNA target sequences. In the system, in one embodiment, the number of ZFAs in the ZF protein domain on a synTF matches the number of orthologus DNA target sequences on the engineered promoter. In the system, in one embodiment, when there are a plurality of ZFA in the ZF protein domain in a synTF and a corresponding plurality number of orthologus DNA target sequences on the engineered promoter in the transcription unit, each ZFA in the synTF is arranged so that the ZFA domain binds corresponding orthologus DNA target sequence of its specific interaction pair. See FIGS. 4A, 9 and 10.

Provided herein, in some aspects, is a kit for regulating gene activation or repression comprising a vector comprising a synthetic transcription factor (synTF) described herein and a vector comprising an engineered promoter described herein.

Provided herein, in some aspects, is a method of regulating gene activation or repression comprising contacting a cell with an engineered gene expression system comprising a synthetic transcription factor (synTF) described herein and an engineered promoter described herein. In another aspect, provided herein is a method of regulating gene activation or repression comprising contacting a cell with a composition comprising one or more engineered synthetic transcription factors (synTFs) described herein and one or more corresponding engineered transcription units comprising the gene of interest.

In some aspects, provided herein are methods and assays to identify DNA sequences for zinc finger arrays that have reduced binding potential in a host genome.

In some aspects, provided herein are methods and assays for designing and constructing 6-finger ZFA or 7-finger ZFA or 8-finger ZFA containing ZF protein domains capable of targeting the identified DNA sequences.

In some aspects, provided herein are methods and assays for designing and constructing synthetic transcription factors (synTFs): zinc finger arrays coupled to transcriptional effector domains (including VP64, p65, KRAB and HP1). See FIGS. 6A-6D.

In some aspects, provided herein are methods and assays for designing and constructing partner synthetic responsive promoters: zinc finger binding sites of different number placed upstream of minimal crippled promoters (e.g., minCMV).

The present invention can be defined in any of the following numbered paragraphs:

[1]. An engineered gene expression system for the in vivo or in vitro regulatable expression of an exogenous gene, the system comprising:
  a) an engineered zinc-finger-containing synthetic transcription factor (synTF) protein comprising two main domains: (i) a first main domain which is a DNA-binding zinc finger protein domain (ZF protein domain), and (ii) a second domain through which the synTF exerts its effect (effector domain), wherein the synTF having the formula I: [ZF protein domain]-[effector domain] or the formula IV: [effector domain]-[ZF protein domain], wherein the ZF protein domain is modular in design and is composed zinc finger arrays (ZFA), wherein there is one or more and up to ten ZFAs, wherein the ZFA comprising a sequence: N'-[(formula II)-$L_2$]$_{6-8}$-C', wherein formula II is that of a ZF motif and is [$X_{0-3}CX_{1-5}CX_{2-7}$-(helix)-$HX_{3-6}H$], where the subscript 6-8 indicates the number of ZF motifs in a ZFA, the ZF motifs that are linked together by the linker $L_2$, the $L_2$ is a linker peptide having 4-6 amino acid residues, and the N'- and C'- indicates the N-terminus and C-terminus respectively of the peptide sequence, and
  b) an engineered responsive promoter comprising
    i). at least one orthogonal target DNA sequence element selected from the group consisting of 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGC-CGTAG-3' (SEQ ID NO: 83), 5'-GGACGACGC-CGATGTAGAAG-3' (SEQ ID NO: 84), 5'-TGAAGCAGTCGACGCCGAAG-3' (SEQ ID NO: 85), 5'-GGACGACGCG GTCTAAGAAG-3' (SEQ ID NO: 86), 5'-CGACGAGGTCG-CATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGAT-GTCGCGC-3' (SEQ ID NO: 90), and 5'-GGTCGTTGCGGTAGTCGAAG-3' (SEQ ID NO: 91) and,
    ii). a promoter sequence, wherein the at least one target DNA sequence element is operably linked to the 5' end of the promoter sequence in order to influence transcription initiation of a nearby coding sequence, wherein the influence is to upregulate or downregulate transcription initiation, and wherein the gene is operably linked to the promoter in the engineered responsive promoter, wherein the ZFA of the synTF binds the at least one orthogonal target DNA sequence element in the engineered responsive promoter.

[2]. The system of paragraph 1, wherein formula II is [$X_3CX_2CX_5$-(helix)-$HX_3H$] (SEQ ID NO: 20).

[3]. The system of paragraph 1 or 2, wherein the sequences of all the helices of each ZFA are selected from within a group selected from the Groups 1-11.

[4]. The system of any one of the preceeding paragraphs, wherein at least four of the helices in a ZFA are selected from the Groups 1-11.

[5]. The system of any one of the preceeding paragraphs, wherein at least four of the helices in a ZF are selected from the same group, the group is selected from the Groups 1-11.

[6]. The system of any one of the preceeding paragraphs, wherein all the helices within a ZFA of the synTF are linked by peptide linkers ($L_2$) having four to six amino acid residues.

[7]. The system of any one of the preceeding paragraphs, where there are a plurality of ZFAs, the ZFAs of the synTF are linked by peptides having 1-20 amino acid residues.

[8]. The system of any one of the preceeding paragraph s, wherein the effector domain of the synTF is a transcription activating domain or a transcription repressor domain.

[9]. The system of any one of the preceeding paragraph s, wherein the effector domain of the synTF is an epigenetic effector domain.

[10]. The system of any one of the preceeding paragraphs, wherein the ZFA of the synTF comprises, consists of, or consist essentially of the ZF motif helices selected from helices disclosed in Group 1, and the ZFA specifically binds the orthogonal DNA sequence Target 1: 5' C GTC GAA GTC GAA GTC GAC C 3' (SEQ ID NO: 81).

[11]. The system of any one of the preceeding paragraphs, wherein the ZFA of the synTF comprises, consists of, or consist essentially of the ZFA helix combo: ZF 1-1, ZF 1-2, ZF 1-3, ZF 1-4, ZF 1-5, ZF 1-6, ZF 1-7, or ZF 1-8 selected from Group 1 ZFA helix combo, and the one ZFA specifically binds the orthogonal DNA sequence Target 1: 5' C GTC GAA GTC GAA GTC GAC C 3' (SEQ ID NO: 81).

[12]. The system of any one of the preceeding paragraphs, wherein the ZFA of the synTF comprises, consists of, or consist essentially of the ZF motif helices selected from the helices disclosed in Group 2, and the ZFA specifically binds the orthogonal DNA sequence Target 2: 5' G GAC GAC GTT ACG GAC GTA C 3' (SEQ ID NO: 82).

[13]. The system of any one of the preceeding paragraphs, wherein the ZFA of the synTF comprises, consists of, or consist essentially of the ZFA helix combo, ZF 2-1, ZF 2-2, ZF 2-3, ZF 2-4, ZF 2-5, ZF 2-6, ZF 2-7, or ZF 2-8 selected from Group 2 ZFA helix combo, and the ZFA specifically binds the orthogonal DNA sequence Target 2: 5' G GAC GAC GTT ACG GAC GTA C 3' (SEQ ID NO: 82).

[14]. The system of any one of the preceeding paragraphs, wherein the ZFA of the synTF comprises, consists of, or consist essentially of the ZF motif helices disclosed in Group 3, and the ZFA specifically binds the orthogonal DNA sequence Target 3: 5' A GAC GTC GAA GTA GCC GTA G 3' (SEQ ID NO: 83).

[15]. The system of any one of the preceeding paragraphs, wherein the ZFA of the synTF comprises, consists of, or consist essentially of the ZFA helix combo, ZF 3-1, ZF 3-2, ZF 3-3, ZF 3-4, ZF 3-5, ZF 3-6, ZF 3-7, or ZF 3-8, selected from Group 3 ZFA helix combo, and the ZFA specifically binds the orthogonal DNA sequence Target 3: 5' A GAC GTC GAA GTA GCC GTA G 3' (SEQ ID NO: 83).

[16]. The system of any one of the preceeding paragraphs, wherein the ZFA of the synTF comprises, consists of, or consist essentially of the ZF motif helices selected from the helices disclosed in Group 4, and the ZFA specifically binds the orthogonal DNA sequence Target 4: 5' G GAC GAC GCC GAT GTA GAA G 3' (SEQ ID NO: 84).

[17]. The system of any one of the preceeding paragraphs, wherein the ZFA of the synTF comprises, consists of, or consist essentially of the ZFA helix combo, ZF 4-1, ZF 4-2, ZF 4-3, ZF 4-4, ZF 4-5, ZF 4-6, ZF 4-7, or ZF 4-8, selected from Group 4 ZFA helix combo, and the ZFA specifically binds the orthogonal DNA sequence Target 4: 5' G GAC GAC GCC GAT GTA GAA G 3' (SEQ ID NO: 84).

[18]. The system of any one of the preceeding paragraphs, wherein the ZFA of the synTF comprises, consists of, or consist essentially of the ZFA helix combo, ZF 5-1, ZF 5-2, ZF 5-3, ZF 5-4, ZF 5-5, ZF 5-6, ZF 5-7, or ZF 5-8, selected from Group 5 ZFA helix combo, and the ZFA specifically binds the orthogonal DNA sequence Target 5: 5' T GAA GCA GTC GAC GCC GAA G 3' (SEQ ID NO: 85).

[19]. The system of any one of the preceeding paragraphs, wherein the ZFA of the synTF comprises, consists of, or consist essentially of the ZF motif helices selected from the helices disclosed in Group 5, and the ZFA specifically binds the orthogonal DNA sequence Target 5: 5' T GAA GCA GTC GAC GCC GAA G 3' (SEQ ID NO: 85).

[20]. The system of any one of the preceeding paragraphs, wherein the ZFA of the synTF comprises, consists of, or consist essentially of the ZFA helix combo, ZF 6-1, ZF 6-2, ZF 6-3, ZF 6-4, ZF 6-5, ZF 6-6, ZF 6-7, or ZF 6-8, selected from Group 6 ZFA helix combo, and the ZFA specifically binds the orthogonal DNA sequence Target 6: 5' G GAC GAC GCG GTC TAA GAA G 3' (SEQ ID NO: 86).

[21]. The system of any one of the preceeding paragraphs, wherein the ZFA of the synTF comprises, consists of, or consist essentially of the ZF motif helices selected from the helices disclosed in Group 6, and the ZFA specifically binds the orthogonal DNA sequence Target 6: 5' G GAC GAC GCG GTC TAA GAA G 3' (SEQ ID NO: 86).

[22]. The system of any one of the preceeding paragraphs, wherein the ZFA of the synTF comprises, consists of, or consist essentially of the ZFA helix combo, ZF 7-1, ZF 7-2, ZF 7-3, ZF 7-4, ZF 7-5, ZF 7-6, ZF 7-7, or ZF 7-8, selected from Group 7 ZFA helix combo, and the ZFA specifically binds the orthogonal DNA sequence Target 7: 5' C GAC GAG GTC GCA TAA GTA G 3' (SEQ ID NO: 87).

[23]. The system of any one of the preceeding paragraphs, wherein the ZFA of the synTF comprises, consists of, or consist essentially of the ZF motif helices selected the helices disclosed in Group 7, and the ZFA specifically binds the orthogonal DNA sequence Target 7: 5' C GAC GAG GTC GCA TAA GTA G 3' (SEQ ID NO: 87).

[24]. The system of any one of the preceeding paragraphs, wherein the ZFA of the synTF comprises, consists of, or consist essentially of the ZFA helix combo, ZF 8-1, ZF 8-2, ZF 8-3, or ZF 8-4, selected from Group 8 ZFA helix combo, and the ZFA specifically binds the orthogonal DNA sequence Target 8: 5' A GAC GCA GTA TAG GTC GAA C 3' (SEQ ID NO: 88).

[25]. The system of any one of the preceeding paragraphs, wherein the ZFA of the synTF comprises, consists of, or consist essentially of the ZF motif helices selected from the helices disclosed in Group 8, and the ZFA specifically binds the orthogonal DNA sequence Target 8: 5' A GAC GCA GTA TAG GTC GAA C 3' (SEQ ID NO: 88).

[26]. The system of any one of the preceeding paragraphs, wherein the ZFA of the synTF comprises, consists of, or consist essentially of the ZFA helix combo, ZF 9-1, ZF 9-2, ZF 9-3, or ZF 9-4, selected from Group 9 ZFA helix combo, and the ZFA specifically binds the orthogonal DNA sequence Target 9: 5' A GAC GCA GTA TAG GAC GAC G 3' (SEQ ID NO: 89).

[27]. The system of any one of the preceeding paragraphs, wherein the ZFA of the synTF comprises, consists of, or consist essentially of the ZF motif helices selected from the helices disclosed in Group 9, and the ZFA specifically binds the orthogonal DNA sequence Target 9: 5' A GAC GCA GTA TAG GAC GAC G 3' (SEQ ID NO: 89).

[28]. The system of any one of the preceeding paragraphs, wherein the ZFA of the synTF comprises, consists of, or consist essentially of the ZFA helix combo, ZF 10, from Group 10, and the at least one ZFA specifically binds the orthogonal DNA sequence Target 10: 5' C GGC GTA GCC GAT GTC GCG C 3' (SEQ ID NO: 90).

[29]. The system of any one of the preceeding paragraphs, wherein the ZFA of the synTF comprises, consists of, or consist essentially of the ZFA helix combo, ZF 11-1, from Group 11, and the at least one ZFA specifically binds the orthogonal DNA sequence Target 11: 5' G GTC GTT GCG GTA GTC GAA G 3' (SEQ ID NO: 91).

[30]. A method of regulating gene activation or repression comprising contacting a cell with an engineered gene expression system of any one of the preceeding claims.

[31]. A kit for regulating gene activation or repression comprising an engineered expression system of any one of the preceeding claims.

[32]. An engineered zinc-finger-containing synthetic transcription factor (synTF) protein comprising two main domains: (a) a first main domain which is a DNA-binding zinc finger protein domain (ZF protein domain), and (b) a second domain through which the synTF exerts its effect (effector domain), wherein the synTF having the formula I: [ZF protein domain]-[effector domain] or the formula IV: [effector domain]-[ZF protein domain], wherein the ZF protein domain is modular in design and is composed zinc finger arrays (ZFA), wherein there is one or more and up to ten ZFAs, wherein the ZFA comprising a sequence: N'-[(formula II)-$L_2$]$_{6-8}$-C', wherein formula II is that of a ZF motif and is [$X_{0-3}CX_{1-5}CX_{2-7}$-(helix)-$HX_{3-6}H$] (SEQ ID NO: 19), where the subscript 6-8 indicates the number of ZF motifs in a ZFA, the ZF motifs that are linked together by the linker $L_2$, the $L_2$ is a linker peptide having 4-6 amino acid residues, and the N'- and C'- indicates the N-terminus and C-terminus respectively of the peptide sequence. The protein optionally further comprises a ligand binding domain or a protein interaction/dimerization domain.

[33]. The protein of paragraph 32, wherein formula II is [$X_3CX_2CX_5$-(helix)-$HX_3H$] (SEQ ID NO: 20).

[34]. The protein of paragraph 32 or 33, wherein the sequences of all the helices of each ZFA are selected from within a group selected from the Groups 1-11.

[35]. The protein of paragraph 32, 33 or 34, wherein at least four of the helices in a ZFA are selected from the Groups 1-11.

[36]. The protein of any one of paragraphs 32-35, wherein at least four of the helices in a ZF are selected from the same group, selected from the Groups 1-11.

[37]. The protein of any one of paragraphs 32-36, wherein the ZFA binds an orthogonal target DNA sequence selected from the group selected from:

a) Target 1:
(SEQ ID NO: 81)
5' C GTC GAA GTC GAA GTC GAC C 3', b) Target 2:
(SEQ ID NO: 82)
5' G GAC GAC GTT ACG GAC GTA C 3', c) Target 3:
(SEQ ID NO: 83)
5' A GAC GTC GAA GTA GCC GTA G 3', d) Target 4:
(SEQ ID NO: 84)
5' G GAC GAC GCC GAT GTA GAA G 3', e) Target 5:
(SEQ ID NO: 85)
5' T GAA GCA GTC GAC GCC GAA G 3', f) Target 6:
(SEQ ID NO: 86)
5' G GAC GAC GCG GTC TAA GAA G 3', g) Target 7:
(SEQ ID NO: 87)
5' C GAC GAG GTC GCA TAA GTA G 3', h) Target 8:
(SEQ ID NO: 88)
5' A GAC GCA GTA TAG GTC GAA C 3', i) Target 9:
(SEQ ID NO: 89)
5' A GAC GCA GTA TAG GAC GAC G 3', j) Target 10:
(SEQ ID NO: 90)
5' C GGC GTA GCC GAT GTC GCG C 3'
and, k) Target 11:
(SEQ ID NO: 91)
5' G GTC GTT GCG GTA GTC GAA G 3'.

[38]. The protein of of any one of paragraphs 32-37, wherein all the helices within a ZFA are linked by peptide linkers ($L_2$) having four to six amino acid residues.

[39]. The protein of of any one of paragraphs 32-38, where there is a plurality of ZFAs, the ZFAs are linked by peptides having 1-20 amino acid residues.

[40]. The protein of of any one of paragraphs 32-39, wherein the effector domain is a transcription activating domain or a transcription repressor domain.

[41]. The protein of of any one of paragraphs 32-40, wherein the effector domain is an epigenetic effector domain.

[42]. The protein of of any one of paragraphs 32-41, wherein the ZFA comprises, consists of, or consist essentially of the ZF motif helices selected from helices disclosed in Group 1, and the ZFA specifically binds the orthogonal DNA sequence Target 1: 5' C GTC GAA GTC GAA GTC GAC C 3' (SEQ ID NO: 81).

[43]. The protein of any one of paragraphs 32-42, wherein the ZFA comprises, consists of, or consist essentially of the ZFA helix combo: ZF 1-1, ZF 1-2, ZF 1-3, ZF 1-4, ZF 1-5, ZF 1-6, ZF 1-7, or ZF 1-8 selected from Group 1 ZFA helix combo, and the one ZFA specifically binds the orthogonal DNA sequence Target 1: 5' C GTC GAA GTC GAA GTC GAC C 3' (SEQ ID NO: 81).

[44]. The protein of any one of paragraphs 32-42, wherein the ZFA therein comprises, consists of, or consist essentially of the ZF motif helices selected from the helices disclosed in Group 2, and the ZFA specifically binds the orthogonal DNA sequence Target 2: 5' G GAC GAC GTT ACG GAC GTA C 3' (SEQ ID NO: 82).

[45]. The protein of any one of paragraphs 32-44, wherein the ZFA comprises, consists of, or consist essentially of the ZFA helix combo, ZF 2-1, ZF 2-2, ZF 2-3, ZF 2-4, ZF 2-5, ZF 2-6, ZF 2-7, or ZF 2-8 selected from Group 2 ZFA helix combo, and the ZFA specifically binds the orthogonal DNA sequence Target 2: 5' G GAC GAC GTT ACG GAC GTA C 3' (SEQ ID NO: 82).

[46]. The protein of any one of paragraphs 32-45, wherein the ZFA comprises, consists of, or consist essentially of the ZF motif helices disclosed in Group 3, and the ZFA specifically binds the orthogonal DNA sequence Target 3: 5' A GAC GTC GAA GTA GCC GTA G 3' (SEQ ID NO: 83).

[47]. The protein of any one of paragraphs 32-46, wherein the ZFA comprises, consists of, or consist essentially of the ZFA helix combo, ZF 3-1, ZF 3-2, ZF 3-3, ZF 3-4, ZF 3-5, ZF 3-6, ZF 3-7, or ZF 3-8, selected from Group 3 ZFA helix combo, and the ZFA specifically binds the orthogonal DNA sequence Target 3: 5' A GAC GTC GAA GTA GCC GTA G 3' (SEQ ID NO: 83).

[48]. The protein of any one of paragraphs 32-47, wherein the ZFA comprises, consists of, or consist essentially of the ZF motif helices selected from the helices disclosed in Group 4, and the ZFA specifically binds the orthogonal DNA sequence Target 4: 5' G GAC GAC GCC GAT GTA GAA G 3' (SEQ ID NO: 84).

[49]. The protein of any one of paragraphs 32-48, wherein the ZFA comprises, consists of, or consist essentially of the ZFA helix combo, ZF 4-1, ZF 4-2, ZF 4-3, ZF 4-4, ZF 4-5, ZF 4-6, ZF 4-7, or ZF 4-8, selected from Group 4 ZFA helix combo, and the ZFA specifically binds the orthogonal DNA sequence Target 4: 5' G GAC GAC GCC GAT GTA GAA G 3' (SEQ ID NO: 84).

[50]. The protein of any one of paragraphs 32-49, wherein the ZFA comprises, consists of, or consist essentially of the ZFA helix combo, ZF 5-1, ZF 5-2, ZF 5-3, ZF 5-4, ZF 5-5, ZF 5-6, ZF 5-7, or ZF 5-8, selected from Group 5 ZFA helix combo, and the ZFA specifically binds the orthogonal DNA sequence Target 5: 5' T GAA GCA GTC GAC GCC GAA G 3' (SEQ ID NO: 85).

[51]. The protein of any one of paragraphs 32-50, wherein the ZFA comprises, consists of, or consist essentially of the ZF motif helices selected from the helices disclosed in Group 5, and the ZFA specifically binds the orthogonal DNA sequence Target 5: 5' T GAA GCA GTC GAC GCC GAA G 3' (SEQ ID NO: 85).

[52]. The protein of any one of paragraphs 32-51, wherein the ZFA therein comprises, consists of, or consist essentially of the ZFA helix combo, ZF 6-1, ZF 6-2, ZF 6-3, ZF 6-4, ZF 6-5, ZF 6-6, ZF 6-7, or ZF 6-8, selected from Group 6 ZFA helix combo, and the ZFA specifically binds the orthogonal DNA sequence Target 6: 5' G GAC GAC GCG GTC TAA GAA G 3' (SEQ ID NO: 86).

[53]. The protein of any one of paragraphs 32-52, wherein the ZFA comprises, consists of, or consist essentially of the ZF motif helices selected from the helices disclosed in Group 6, and the ZFA specifically binds the orthogonal DNA sequence Target 6: 5' G GAC GAC GCG GTC TAA GAA G 3' (SEQ ID NO: 86).

[54]. The protein of any one of paragraphs 32-53, wherein the ZFA comprises, consists of, or consist essentially of the ZFA helix combo, ZF 7-1, ZF 7-2, ZF 7-3, ZF 7-4, ZF 7-5, ZF 7-6, ZF 7-7, or ZF 7-8, selected from Group 7 ZFA helix combo, and the ZFA specifically binds the orthogonal DNA sequence Target 7: 5' C GAC GAG GTC GCA TAA GTA G 3' (SEQ ID NO: 87).

[55]. The protein of any one of paragraphs 32-54, wherein the ZFA therein comprises, consists of, or consist essentially of the ZF motif helices selected the helices disclosed in Group 7, and the ZFA specifically binds the orthogonal DNA sequence Target 7: 5' C GAC GAG GTC GCA TAA GTA G 3' (SEQ ID NO: 87).

[56]. The protein of any one of paragraphs 32-55, wherein the ZFA comprises, consists of, or consist essentially of the ZFA helix combo, ZF 8-1, ZF 8-2, ZF 8-3, or ZF 8-4, selected from Group 8 ZFA helix combo, and the ZFA specifically binds the orthogonal DNA sequence Target 8: 5' A GAC GCA GTA TAG GTC GAA C 3' (SEQ ID NO: 88).

[57]. The protein of any one of paragraphs 32-56, wherein the ZFA comprises, consists of, or consist essentially of the ZF motif helices selected from the helices disclosed in Group 8, and the ZFA specifically binds the orthogonal DNA sequence Target 8: 5' A GAC GCA GTA TAG GTC GAA C 3' (SEQ ID NO: 88).

[58]. The protein of any one of paragraphs 32-57, wherein the ZFA comprises, consists of, or consist essentially of the ZFA helix combo, ZF 9-1, ZF 9-2, ZF 9-3, or ZF 9-4, selected from Group 9 ZFA helix combo, and the ZFA specifically binds the DNA sequence Target 9: 5' A GAC GCA GTA TAG GAC GAC G 3' (SEQ ID NO: 89).

[59]. The protein of any one of paragraphs 32-58, wherein the ZFA comprises, consists of, or consist essentially of the ZF motif helices selected from the helices disclosed in Group 9, and the ZFA specifically binds the orthogonal DNA sequence Target 9: 5' A GAC GCA GTA TAG GAC GAC G 3' (SEQ ID NO: 89).

[60]. The protein of any one of paragraphs 32-59, wherein the ZFA comprises, consists of, or consist essentially of the ZFA helix combo, ZF 10, from Group 10, and the at least one ZFA specifically binds the DNA sequence Target 10: 5' C GGC GTA GCC GAT GTC GCG C 3' (SEQ ID NO: 90).

[61]. The protein of any one of paragraphs 32-60, wherein the ZFA comprises, consists of, or consist essentially of the ZFA helix combo, ZF 11-1, from Group 11, and the at least one ZFA specifically binds the orthogonal DNA sequence Target 11: 5' G GTC GTT GCG GTA GTC GAA G 3' (SEQ ID NO: 91).

[62]. An engineered responsive promoter comprising (a) at least one target DNA sequence element selected from the group consisting of 5'-CGTCGAAGTCGAAGTC-GACC-3' (SEQ ID NO: 81), 5'-GGACGACGTTACG-GACGTAC-3' (SEQ ID NO: 82), 5'-AGACGTC-GAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAG-TAG-3' (SEQ ID NO: 87), 5'-AGACGCAGTATAG-GTCGAAC-3' (SEQ ID NO: 88), 5'-AGACGCAG-TATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91) and (b) a promoter sequence, wherein the at least one target DNA sequence element is operably linked 5' end of the promoter sequence in order to influence transcription initiation of a nearby coding sequence.

[63]. The engineered promoter of paragraph 62 comprising at least one and up to ten target DNA sequence elements.

[64]. The engineered promoter of paragraph 62 or 63, wherein the promoter is a full-length functional promoter or a minimal promoter.

[65]. A kit for regulating gene activation or repression comprising a vector comprising nucleic acid for the expression of (a) a synthetic transcription factor (synTF) of paragraph 32-60 or ZF-containing fusion protein of paragraph 66-95, and (b) a vector comprising an engineered promoter of paragraph 61-64.

[66]. An engineered zinc-finger-containing fusion protein comprising two main domains: (a) a first main domain which is a DNA-binding zinc finger protein domain (ZF protein domain), and (b) a second main domain comprising a ligand binding domain or a protein interaction/dimerization domain, wherein the synTF having the configuration: [ZF protein domain]-[ligand binding domain or a protein interaction/dimerization domain] or the the configuration: [ligand binding domain or a protein interaction/dimerization domain]-[ZF protein domain], wherein the ZF protein domain is modular in design and is composed zinc finger arrays (ZFA), wherein there is one or more and up to ten ZFAs, wherein the ZFA comprising a sequence: N'-[(formula II)-L2]$_{6-8}$-C', wherein formula II is that of a ZF motif and is [X$_{0-3}$CX$_{1-5}$CX$_{2-7}$-(helix)-HX$_{3-6}$H] (SEQ ID NO: 19), where the subscript 6-8 indicates the number of ZF motifs in a ZFA, the ZF motifs that are linked together by the linker L$_2$, the L$_2$ is a linker peptide having 4-6 amino acid residues, and the N'- and C'- indicates the N-terminus and C-terminus respectively of the peptide sequence.

[67]. The protein of paragraph 66, wherein formula II is [X$_3$CX$_2$CX$_5$-(helix)-HX$_3$H] (SEQ ID NO: 20).

[68]. The protein of paragraph 66 or 67, wherein the sequences of all the helices of each ZFA are selected from within a group selected from the Groups 1-11.

[69]. The protein of paragraph 66, 67 or 68, wherein at least four of the helices in a ZFA are selected from the Groups 1-11.

[70]. The protein of any one of paragraphs 66-69, wherein at least four of the helices in a ZF are selected from the same group, selected from the Groups 1-11.

[71]. The protein of any one of paragraphs 66-70, wherein the ZFA binds an orthogonal target DNA sequence selected from the group selected from:

a) Target 1:
                                    (SEQ ID NO: 81)
5' C GTC GAA GTC GAA GTC GAC C 3', b) Target 2:
                                    (SEQ ID NO: 82)
5' G GAC GAC GTT ACG GAC GTA C 3', c) Target 3:
                                    (SEQ ID NO: 83)
5' A GAC GTC GAA GTA GCC GTA G 3', d) Target 4:
                                    (SEQ ID NO: 84)
5' G GAC GAC GCC GAT GTA GAA G 3', e) Target 5:
                                    (SEQ ID NO: 85)
5' T GAA GCA GTC GAC GCC GAA G 3', f) Target 6:
                                    (SEQ ID NO: 86)
5' G GAC GAC GCG GTC TAA GAA G 3', g) Target 7:
                                    (SEQ ID NO: 87)
5' C GAC GAG GTC GCA TAA GTA G 3', h) Target 8:
                                    (SEQ ID NO: 88)
5' A GAC GCA GTA TAG GTC GAA C 3', i) Target 9:
                                    (SEQ ID NO: 89)
5' A GAC GCA GTA TAG GAC GAC G 3', j) Target 10:
                                    (SEQ ID NO: 90)
5' C GGC GTA GCC GAT GTC GCG C 3'
and, k) Target 11:
                                    (SEQ ID NO: 91)
5' G GTC GTT GCG GTA GTC GAA G 3'.

[72]. The protein of of any one of paragraphs 66-72, wherein all the helices within a ZFA are linked by peptide linkers (L$_2$) having four to six amino acid residues.

[73]. The protein of of any one of paragraphs 66-72, where there is a plurality of ZFAs, the ZFAs are linked by peptides having 1-20 amino acid residues.

[74]. The protein of of any one of paragraphs 66-73, wherein the ligand binding domain is a receptor ligand binding domain.

[75]. The protein of of any one of paragraphs 74, wherein the ligand binding domain is an estrogen receptor ligand binding domain.

[76]. The protein of of any one of paragraphs 66-75, wherein the ZFA comprises, consists of, or consist essentially of the ZF motif helices selected from helices disclosed in Group 1, and the ZFA specifically binds the orthogonal DNA sequence Target 1: 5' C GTC GAA GTC GAA GTC GAC C 3' (SEQ ID NO: 81).

[77]. The protein of any one of paragraphs 66-76, wherein the ZFA comprises, consists of, or consist essentially of the ZFA helix combo: ZF 1-1, ZF 1-2, ZF 1-3, ZF 1-4, ZF 1-5, ZF 1-6, ZF 1-7, or ZF 1-8 selected from Group 1 ZFA helix combo, and the one ZFA specifically binds the orthogonal DNA sequence Target 1: 5' C GTC GAA GTC GAA GTC GAC C 3' (SEQ ID NO: 81).

[78]. The protein of any one of paragraphs 66-77, wherein the ZFA therein comprises, consists of, or consist essentially of the ZF motif helices selected from the helices disclosed in Group 2, and the ZFA specifically binds the orthogonal DNA sequence Target 2: 5' G GAC GAC GTT ACG GAC GTA C 3' (SEQ ID NO: 82).

[79]. The protein of any one of paragraphs 66-78, wherein the ZFA comprises, consists of, or consist essentially of the ZFA helix combo, ZF 2-1, ZF 2-2, ZF 2-3, ZF 2-4, ZF 2-5, ZF 2-6, ZF 2-7, or ZF 2-8 selected from Group 2 ZFA helix combo, and the ZFA specifically binds the orthogonal DNA sequence Target 2: 5' G GAC GAC GTT ACG GAC GTA C 3' (SEQ ID NO: 82).

[80]. The protein of any one of paragraphs 66-79, wherein the ZFA comprises, consists of, or consist essentially of the ZF motif helices disclosed in Group 3, and the ZFA specifically binds the orthogonal DNA sequence Target 3: 5' A GAC GTC GAA GTA GCC GTA G 3' (SEQ ID NO: 83).

[81]. The protein of any one of paragraphs 66-80, wherein the ZFA comprises, consists of, or consist essentially of the ZFA helix combo, ZF 3-1, ZF 3-2, ZF 3-3, ZF 3-4, ZF 3-5, ZF 3-6, ZF 3-7, or ZF 3-8, selected from Group 3 ZFA helix combo, and the ZFA specifically binds the orthogonal DNA sequence Target 3: 5' A GAC GTC GAA GTA GCC GTA G 3' (SEQ ID NO: 83).

[82]. The protein of any one of paragraphs 66-81, wherein the ZFA comprises, consists of, or consist essentially of the ZF motif helices selected from the helices disclosed in Group 4, and the ZFA specifically binds the orthogonal DNA sequence Target 4: 5' G GAC GAC GCC GAT GTA GAA G 3' (SEQ ID NO: 84).

[83]. The protein of any one of paragraphs 66-82, wherein the ZFA comprises, consists of, or consist essentially of the ZFA helix combo, ZF 4-1, ZF 4-2, ZF 4-3, ZF 4-4, ZF 4-5, ZF 4-6, ZF 4-7, or ZF 4-8, selected from Group 4 ZFA helix combo, and the ZFA specifically binds the orthogonal DNA sequence Target 4: 5' G GAC GAC GCC GAT GTA GAA G 3' (SEQ ID NO: 84).

[84]. The protein of any one of paragraphs 66-83, wherein the ZFA comprises, consists of, or consist essentially of the ZFA helix combo, ZF 5-1, ZF 5-2, ZF 5-3, ZF 5-4, ZF 5-5, ZF 5-6, ZF 5-7, or ZF 5-8, selected from Group 5 ZFA helix combo, and the ZFA specifically binds the orthogonal DNA sequence Target 5: 5' T GAA GCA GTC GAC GCC GAA G 3' (SEQ ID NO: 85).

[85]. The protein of any one of paragraphs 66-84, wherein the ZFA comprises, consists of, or consist essentially of the ZF motif helices selected from the helices disclosed in Group 5, and the ZFA specifically binds the orthogonal DNA sequence Target 5: 5' T GAA GCA GTC GAC GCC GAA G 3' (SEQ ID NO: 85).

[86]. The protein of any one of paragraphs 66-85, wherein the ZFA therein comprises, consists of, or consist essentially of the ZFA helix combo, ZF 6-1, ZF 6-2, ZF 6-3, ZF 6-4, ZF 6-5, ZF 6-6, ZF 6-7, or ZF 6-8, selected from Group 6 ZFA helix combo, and the ZFA specifically binds the orthogonal DNA sequence Target 6: 5' G GAC GAC GCG GTC TAA GAA G 3' (SEQ ID NO: 86).

[87]. The protein of any one of paragraphs 66-86, wherein the ZFA comprises, consists of, or consist essentially of the ZF motif helices selected from the helices disclosed in Group 6, and the ZFA specifically binds the orthogonal DNA sequence Target 6: 5' G GAC GAC GCG GTC TAA GAA G 3' (SEQ ID NO: 86).

[88]. The protein of any one of paragraphs 66-87, wherein the ZFA comprises, consists of, or consist essentially of the ZFA helix combo, ZF 7-1, ZF 7-2, ZF 7-3, ZF 7-4, ZF 7-5, ZF 7-6, ZF 7-7, or ZF 7-8, selected from Group 7 ZFA helix combo, and the ZFA specifically binds the orthogonal DNA sequence Target 7: 5' C GAC GAG GTC GCA TAA GTA G 3' (SEQ ID NO: 87).

[89]. The protein of any one of paragraphs 66-88, wherein the ZFA therein comprises, consists of, or consist essentially of the ZF motif helices selected the helices disclosed in Group 7, and the ZFA specifically binds the orthogonal DNA sequence Target 7: 5' C GAC GAG GTC GCA TAA GTA G 3' (SEQ ID NO: 87).

[90]. The protein of any one of paragraphs 66-89, wherein the ZFA comprises, consists of, or consist essentially of the ZFA helix combo, ZF 8-1, ZF 8-2, ZF 8-3, or ZF 8-4, selected from Group 8 ZFA helix combo, and the ZFA specifically binds the orthogonal DNA sequence Target 8: 5' A GAC GCA GTA TAG GTC GAA C 3' (SEQ ID NO: 88).

[91]. The protein of any one of paragraphs 66-90, wherein the ZFA comprises, consists of, or consist essentially of the ZF motif helices selected from the helices disclosed in Group 8, and the ZFA specifically binds the orthogonal DNA sequence Target 8: 5' A GAC GCA GTA TAG GTC GAA C 3' (SEQ ID NO: 88).

[92]. The protein of any one of paragraphs 66-91, wherein the ZFA comprises, consists of, or consist essentially of the ZFA helix combo, ZF 9-1, ZF 9-2, ZF 9-3, or ZF 9-4, selected from Group 9 ZFA helix combo, and the ZFA specifically binds the DNA sequence Target 9: 5' A GAC GCA GTA TAG GAC GAC G 3' (SEQ ID NO: 89).

[93]. The protein of any one of paragraphs 66-92, wherein the ZFA comprises, consists of, or consist essentially of the ZF motif helices selected from the helices disclosed in Group 9, and the ZFA specifically binds the orthogonal DNA sequence Target 9: 5' A GAC GCA GTA TAG GAC GAC G 3' (SEQ ID NO: 89).

[94]. The protein of any one of paragraphs 66-93, wherein the ZFA comprises, consists of, or consist essentially of the ZFA helix combo, ZF 10, from Group 10, and the at least one ZFA specifically binds the DNA sequence Target 10: 5' C GGC GTA GCC GAT GTC GCG C 3' (SEQ ID NO: 90).

[95]. The protein of any one of paragraphs 66-94, wherein the ZFA comprises, consists of, or consist essentially of the ZFA helix combo, ZF 11-1, from Group 11, and the at least one ZFA specifically binds the orthogonal DNA sequence Target 11: 5' G GTC GTT GCG GTA GTC GAA G 3' (SEQ ID NO: 91).

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLE

In some aspects, provided herein are methods and assays for characterization of synTF activity using, for example, reporter assays in mammalian cell lines, including HEK293 cells and TE671/RD human rhabdomyosarcoma cells. The characterization can include, for example, assaying cross-activity of synTFs with different (non-cognate) promoter pairs.

Exemplary assays for characterization of 6-finger ZFA containing synTFs and responsive promoter elements are described herein. RNA-seq experiments can also be performed to measure the entire transcriptome of host cells in the context of synTFs. These experiments are aimed at characterizing the extent to which the synTFs are functionally orthogonal to host genomes.

Cell Culture Conditions

HEK293FT (American Type Culture Collection, ATCC) cells were cultured in DMEM supplemented with 10% FBS, 1% Glutamax, 1% Non-essential amino acids solution and 1% penicillin-streptomycin. Cells were incubated at 37° C. and 5% $CO_2$.

Transient Transfection Experimental Conditions

Seeded 40,000 HEK293FT cells/well in 1×DMEM in 48-well plates. Incubated at 37° C.+5% $CO_2$ for 24 hours. Transfected 300 ng total DNA per well (1:1:1 ratio of TF:Reporter:Alexa Fluor Transfection Marker) using 3 uL DNA, 3.6 uL PEI, and 18.4 uL NaCl. Incubated at 37° C.+5% $CO_2$ for 48 hours. Trypsinized cells and ran on a BD LSR FORTESSA flow cytometer using FSC: 260, SSC: 225, and PMTVs: FITC: 260, TxRed: 350, Alexa Fluor: 350. Gated populations via FSC and SSC, and obtained geometric means of fluorescence.

Plasmids encoding synthetic reporters and synTFs were transfected into HEK293FT cells by PEI. 40K HEK293FT cells were seeded into 48-well plates and transfected the following day with total of 300 ng of DNA (with equal ratio of testing constructs including IR fluorescent protein (iRFP) as a transfection marker). Flow cytometry analysis after 48 hours, using a BD LSR Fortessa flow cytometer, showed ~80-90% of transfected cells were iRFP+ under these conditions. Populations were gated via forward-scatter (FSC) and side-scatter (SSC) and geometric means of fluorescence were obtained.

Integration Experimental Conditions

To singly integrate reporters into the human genome, plasmids encoding synthetic reporters (cloned within AAVS1 homology arm sequences) were transfected into HEK293FT cells by PEI, along with plasmids encoding Cas9-HF1 and AAVS1-targeting gRNA. 40K HEK293FT cells were seeded into 48-well plates and transfected the following day with total of 300 ng of DNA. Cells were selected under 2 ug/mL Puromycin for 12-14 days to generate polyclonal integrated lines. Transient transfection of plasmids encoding synTFs into the stable reporter lines was subsequently conducted using the above transient transfection protocol.

SynTF VP64 Activator Screen

Each synTF (as fusions to VP64) was tested with its corresponding 1× responsive reporter (green fluorescent protein, GFP) using transient transfection to determine the most potent activator.

Each synTF was also tested with its corresponding 4×- or 5×-responsive reporter using transient transfection to determine the most potent activator. Data not shown.

Figure 7:
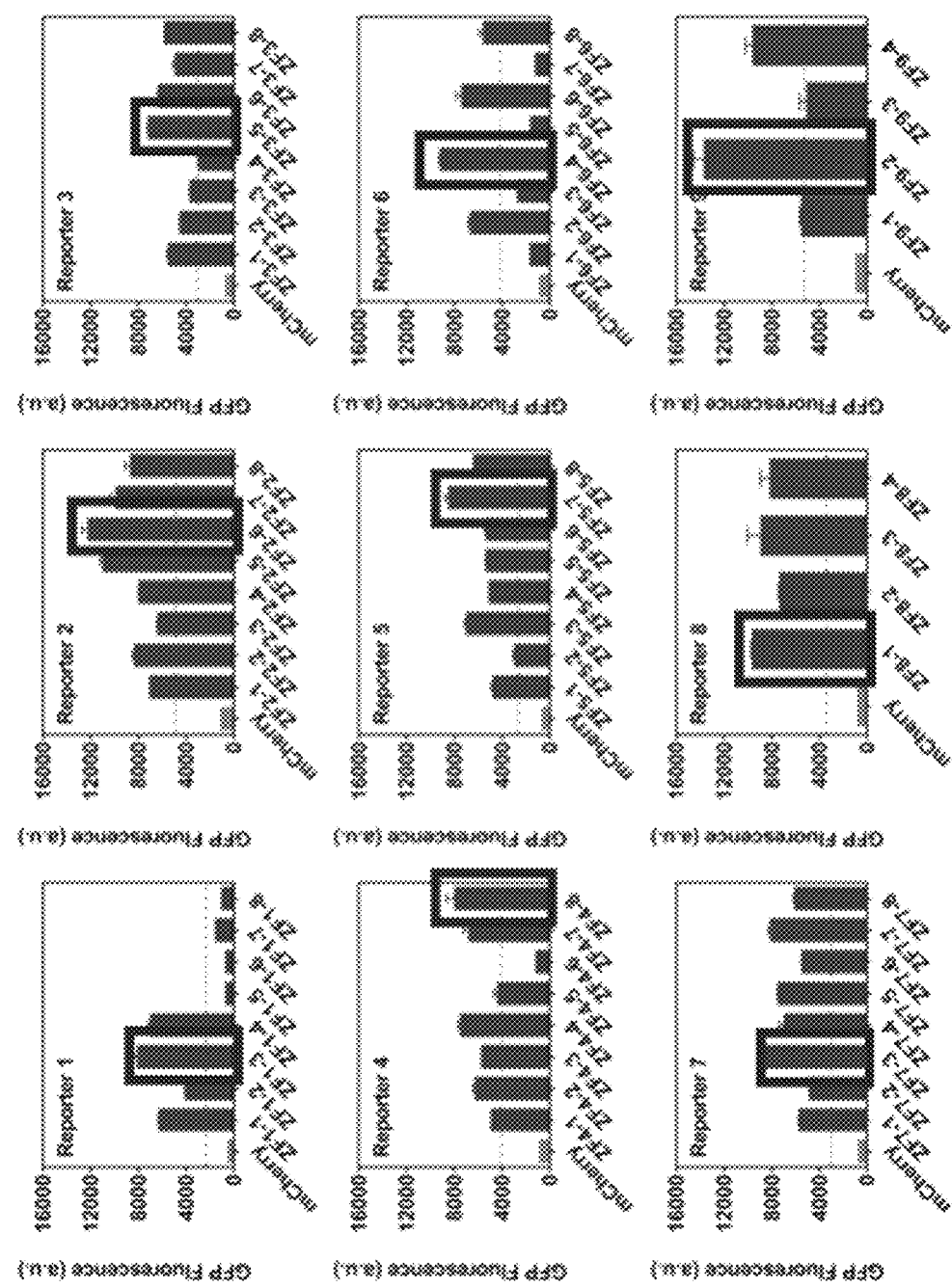
FIG. 7 demonstrates results obtained where each synTF having VP64 as the effector domain described herein was tested with its corresponding 1× responsive reporter in HEK 293 cells to determine the most potent activators. In addition, each synTF was tested with its corresponding 4× responsive reporter to determine the most potent activators. Experiments were done using transient transfection. A 1× responsive reporter is a reporter gene operable linked to a responsive promoter engineered with one orthogonal DNA target site for the zinc finger binding of a synTF having a single zinc finger array. A 4× responsive reporter is a reporter gene operable linked to a responsive promoter engineered with one orthogonal DNA target site for the zinc finger binding of a synTF having four zinc finger arrays.
Figure 7:
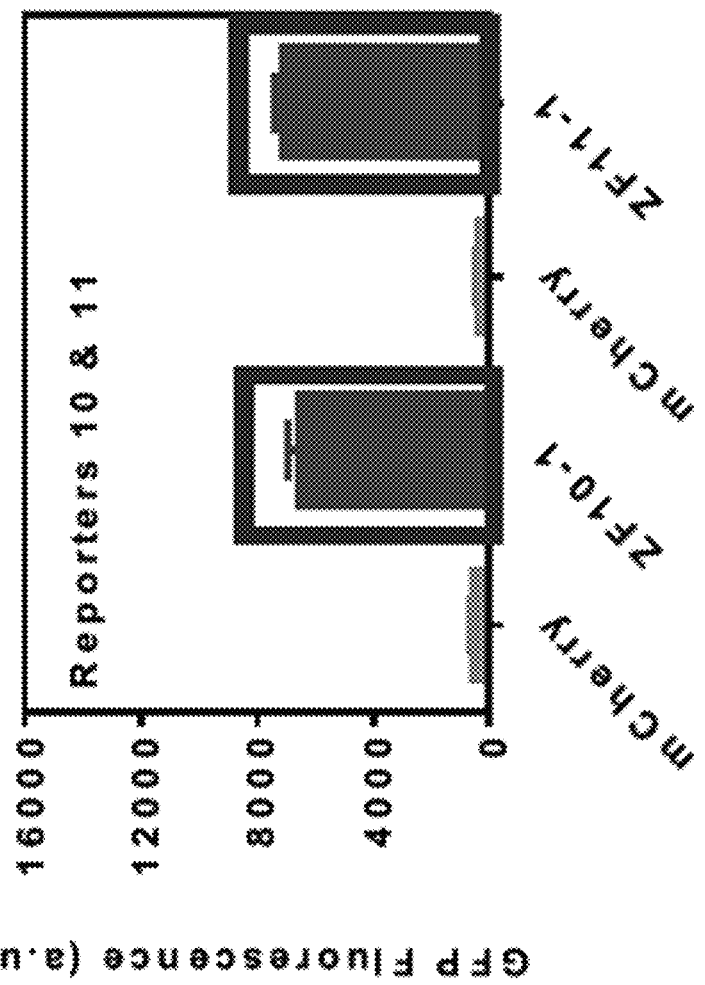
Figure 8:
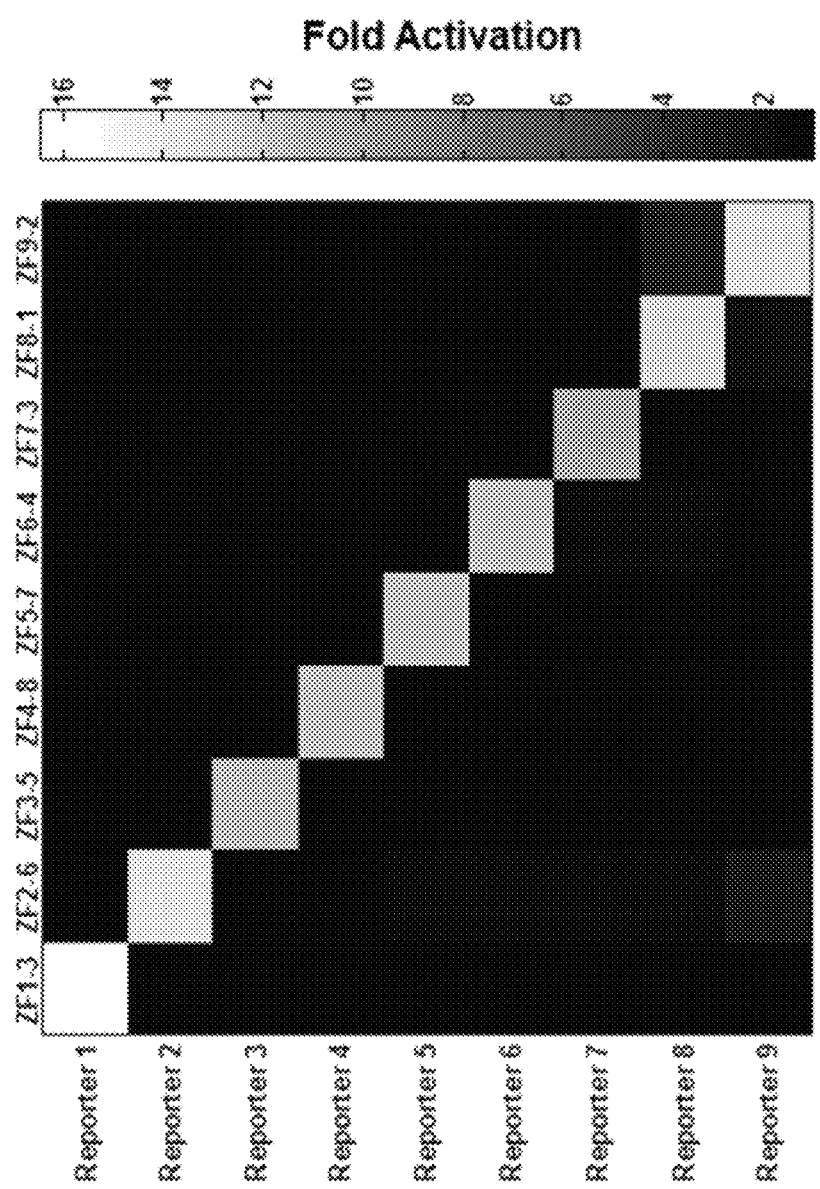
FIG. 8 shows results obtained for designated synTFs 1-3, 2-6, 3-5, 4-8, 5-7, 6-4, 7-3, 8-1, and 9-2 (fusions to VP64) were tested against all respective 1× responsive reporters using transient transfection to assay for cross-activity.

Exemplary results from these assays are provided herein in FIGS. 7-8.

FIG. 7 shows the effectiveness of different ZF helix combinations in a six-finger ZFA synTF having the VY64 activation domain, activating gene expression in a 1× target promoter operable linked to a green fluorescent protein as the GOI. SynTFs having the ZF helix combo: ZF1-3, 2-6, 3-5, 4-8, 5-7, 6-4, 7-3, 8-1, and 9-2 are shown to be very effective.

SynTFs having the ZF helix combo: ZF1-3, 2-6, 3-5, 4-8, 5-7, 6-4, 7-3, 8-1, and 9-2, and fusioned to VP64 activation domain were further were tested against all respective 1× target responsive reporters using transient transfection to assay for cross-activity. FIG. 8 shows more than 10 fold GFP activation with the respective target responsive reporters and non-detectable GFP activation with non-specific target responsive reporters, supporting the orthologonal design of the ZFA and target sequence.

SynTF KRAB Repressor Activity

Figure 12:
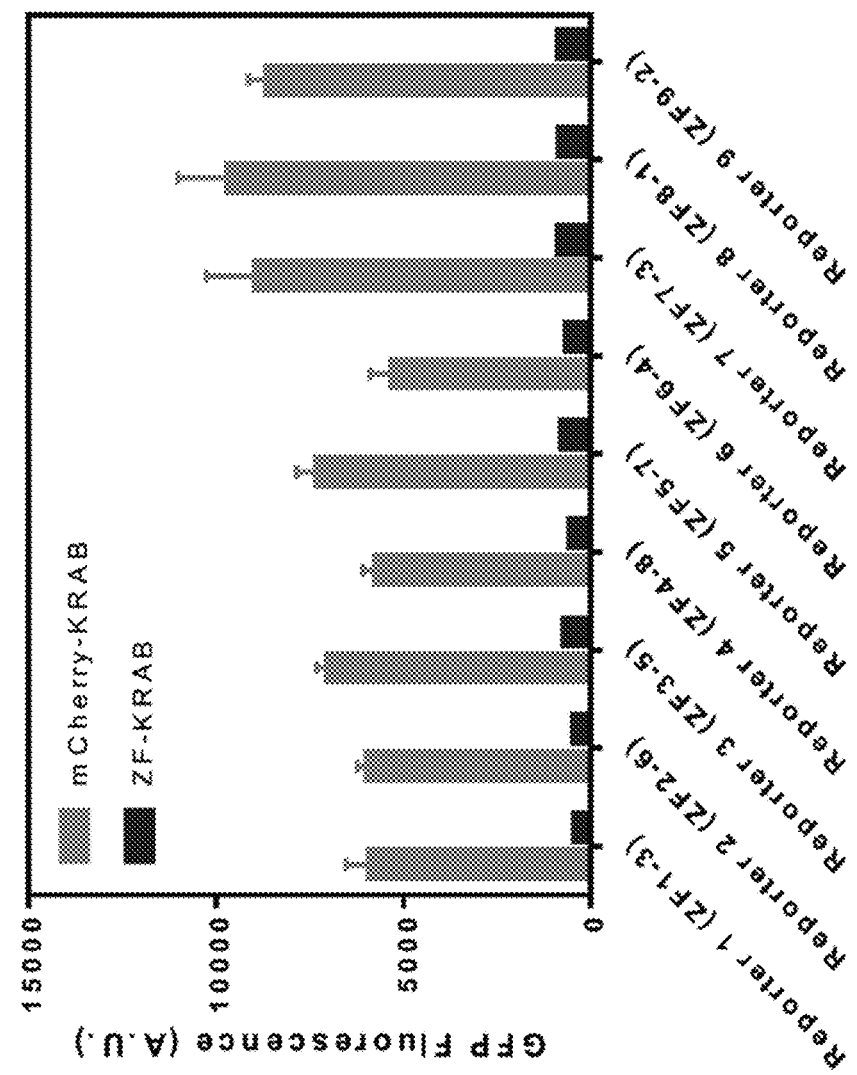
FIG. 12 demonstrates one example of synTF KRAB repressor activity in an engineered gene expression system. Repressor can silence strong promoters such as full-length CMV promoter.

SynTF transcriptional repressors using the KRAB repression domain can silence the (strong) full length CMV promoter in HEK293 cells. Experiment was done using transient transfection. Data shown in FIG. 12. All synTFs having the ZF helix combo: ZF1-3, 2-6, 3-5, 4-8, 5-7, 6-4, 7-3, 8-1, and 9-2, and fusioned to KRAB repression domain effectively repressed the GPF expression from a 1× target promoter operable linked to a green fluorescent protein as the GOI.

SynTF HP1 Repressor Activity

Figure 13:
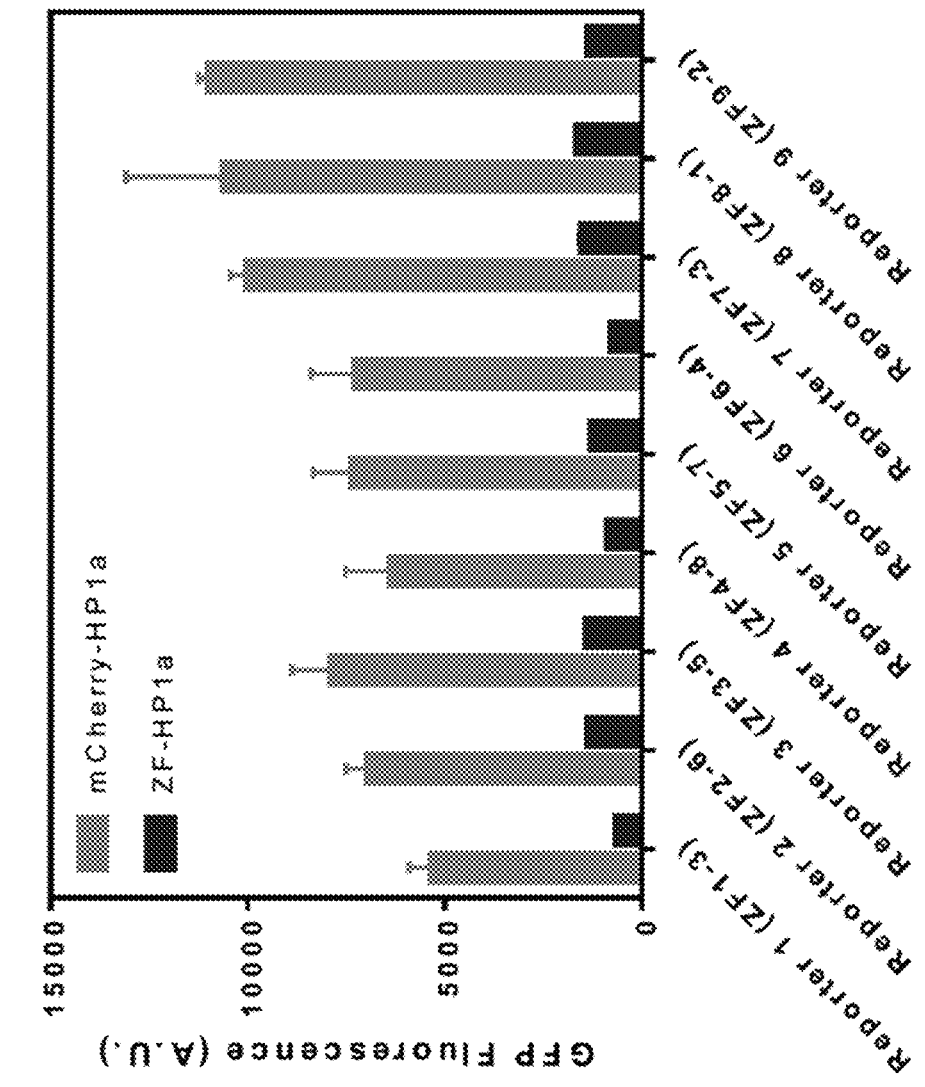
FIG. 13 demonstrates another example of synTF HP1 repressor activity in an engineered gene expression system. Repressor can silence strong promoters such as full-length CMV promoter.

SynTF transcriptional repressors using the HP1 repression domain can silence the (strong) full length CMV promoter in HEK293 cells. Experiment was done using transient transfection. Data shown FIG. 13. Similar to the synTFs having the KRAB repression domain, All synTFs having the ZF helix combo: ZF1-3, 2-6, 3-5, 4-8, 5-7, 6-4, 7-3, 8-1, and 9-2, and fusioned to HP1 repression domain effectively repressed the GPF expression from a 1× target promoter operable linked to a green fluorescent protein as the GOI.

SynTF p65 Activation Activity

Genome-wide transcriptome (RNA-seq) experiment with the ZF-p65 fusions, ZF fused to the activation domain of NFκB shows minimal genome-wide off-target gene expression events. Data not shown.

Figure 14:
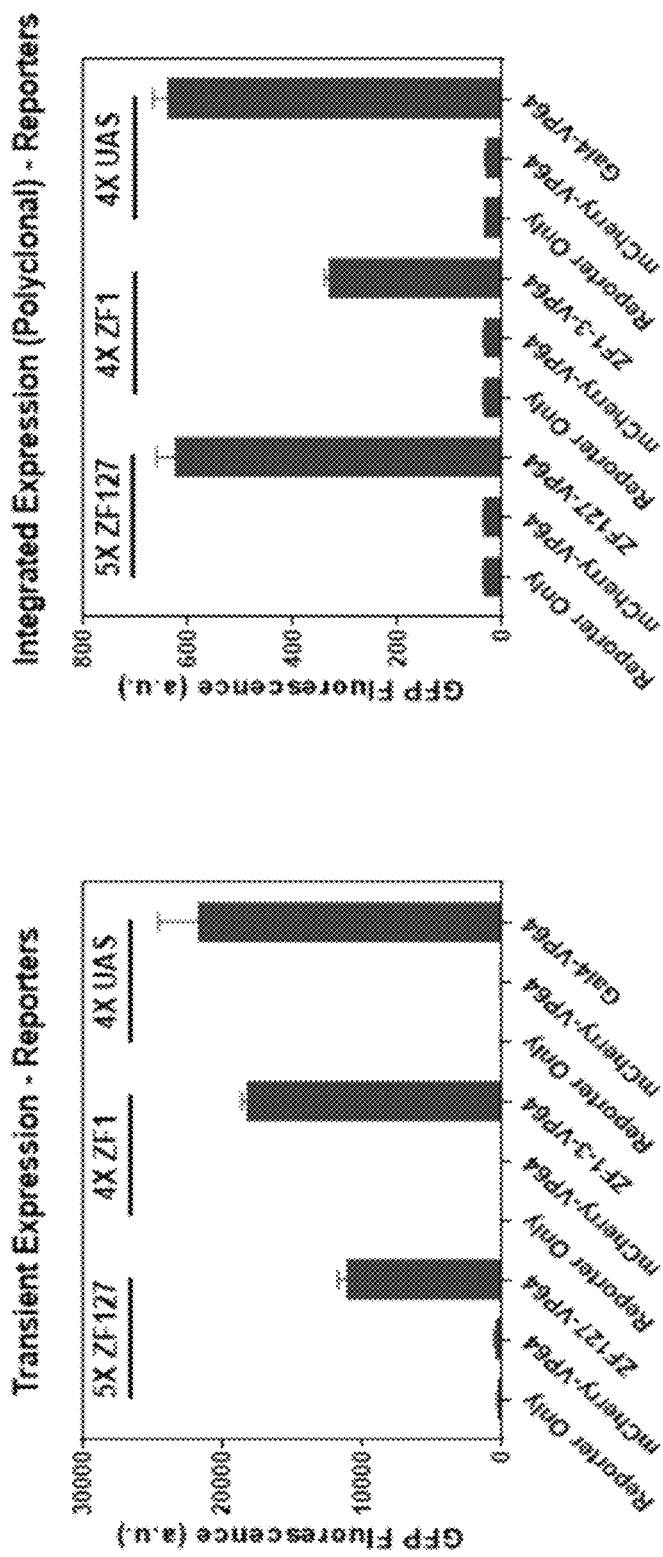
FIG. 14 demonstrates that the synTF can robustly activate responsive promoters in both transfected plasmid and genome integrated synthetic reporters.

SynTF Activation for Plasmid (Transient) Vs. Integrated Synthetic Reporters synTF transcriptional activators are capable of activating stably and singly integrated synthetic reporters in HEK293 cells. Data shown is shown in FIG. 14. Experiment on the left was done using transient transfection of synTFs and reporters. Experiment on the right was done using transient transfection of synTFs into stable integration reporter lines. The synTF transcriptional activators of this disclosure are able to activate gene expressions in both plasmids and integrated synthetic reporters.

SynTF Activation Vs. Constitutive Full Length CMV Promoter

Figure 9:
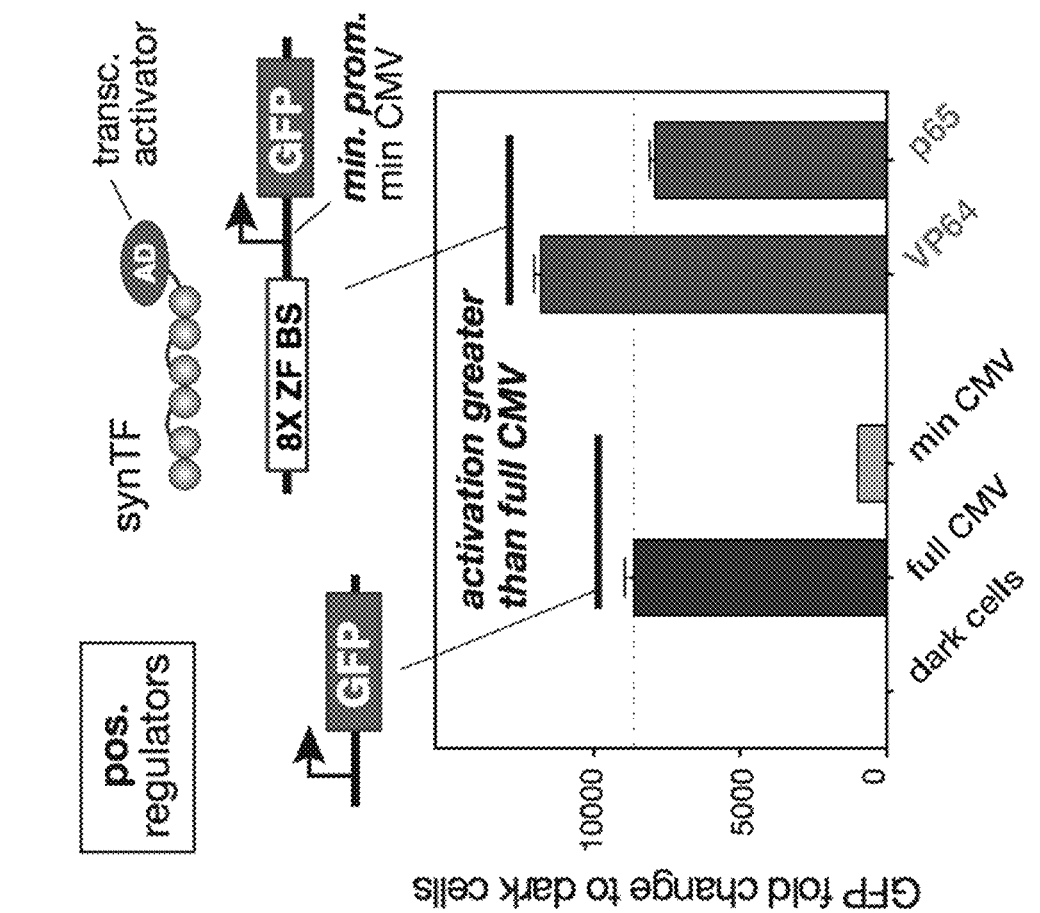
FIG. 9 shows a comparison of synTF transcriptional activation versus full length (strong) CMV promoter in HEK293 cells. The figure shows that synTF transcriptional activators can achieve activation levels greater than that of the (strong) full length CMV promoter in HEK293 cells. Experiment was done using transient transfection.

SynTF transcriptional activators can achieve activation levels greater than that of the (strong) full length CMV promoter in HEK293 cells. Experiment was done using transient transfection. Data are shown in FIG. 9.

SynTF Repression Vs. Constitutive Full Length CMV Promoter

Figure 10:
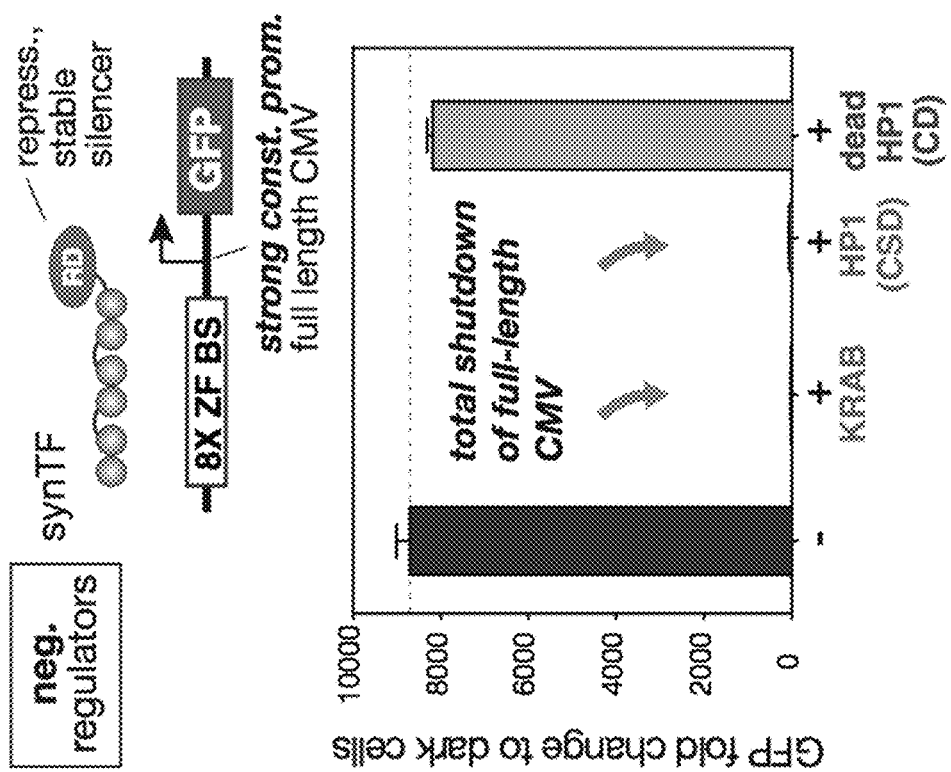
FIG. 10 shows that synTF transcriptional repressors can fully silence full length CMV promoter in HEK293 cells. Experiment was done using transient transfection.

SynTF transcriptional repressors can silence the (strong) full length CMV promoter in HEK293 cells. Experiment was done using transient transfection. Data is shown in FIG. 10.

SynTF Functionality Across Mammalian Cell Lines and Eukaryotic Systems

Figure 11:
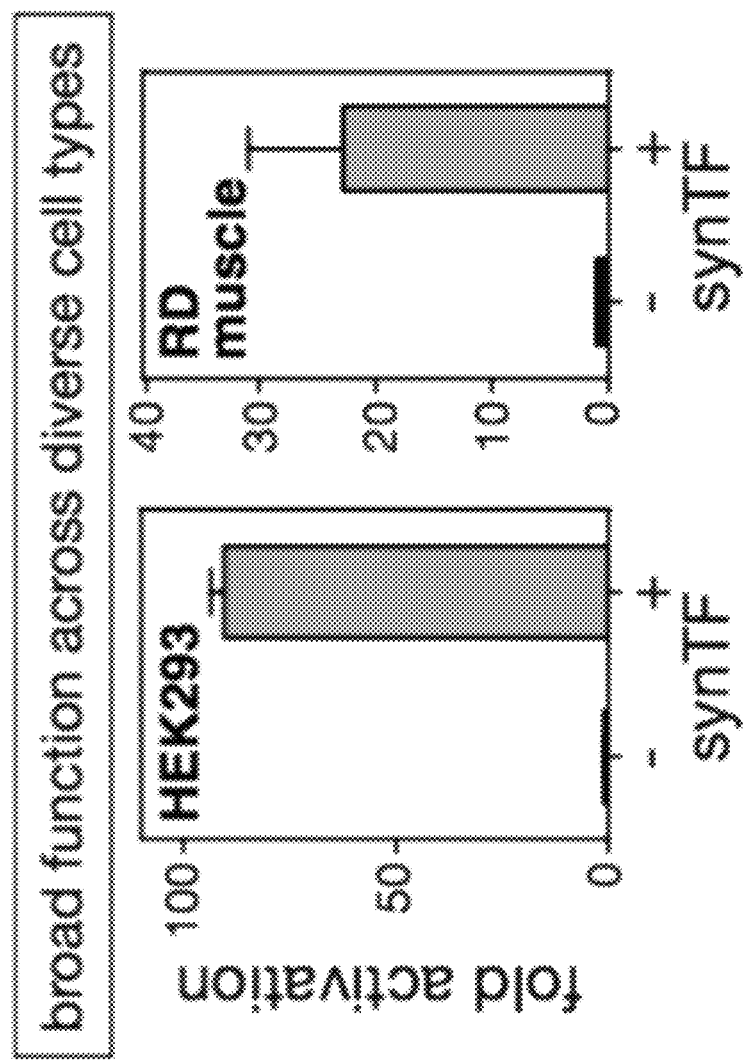
FIG. 11 demonstrates that synTFs have broad functionality across mammalian cell lines and eukaryotic systems. Data shown is for HEK293 cells and TE671/RD cells.

SynTFs are broadly functional across eukaryotic systems. Experiment was done using transient transfection. Data is shown in FIG. 11 with HEK293 cells and TE671/RD cells as representative eukaryotic cells.

Figure 15:
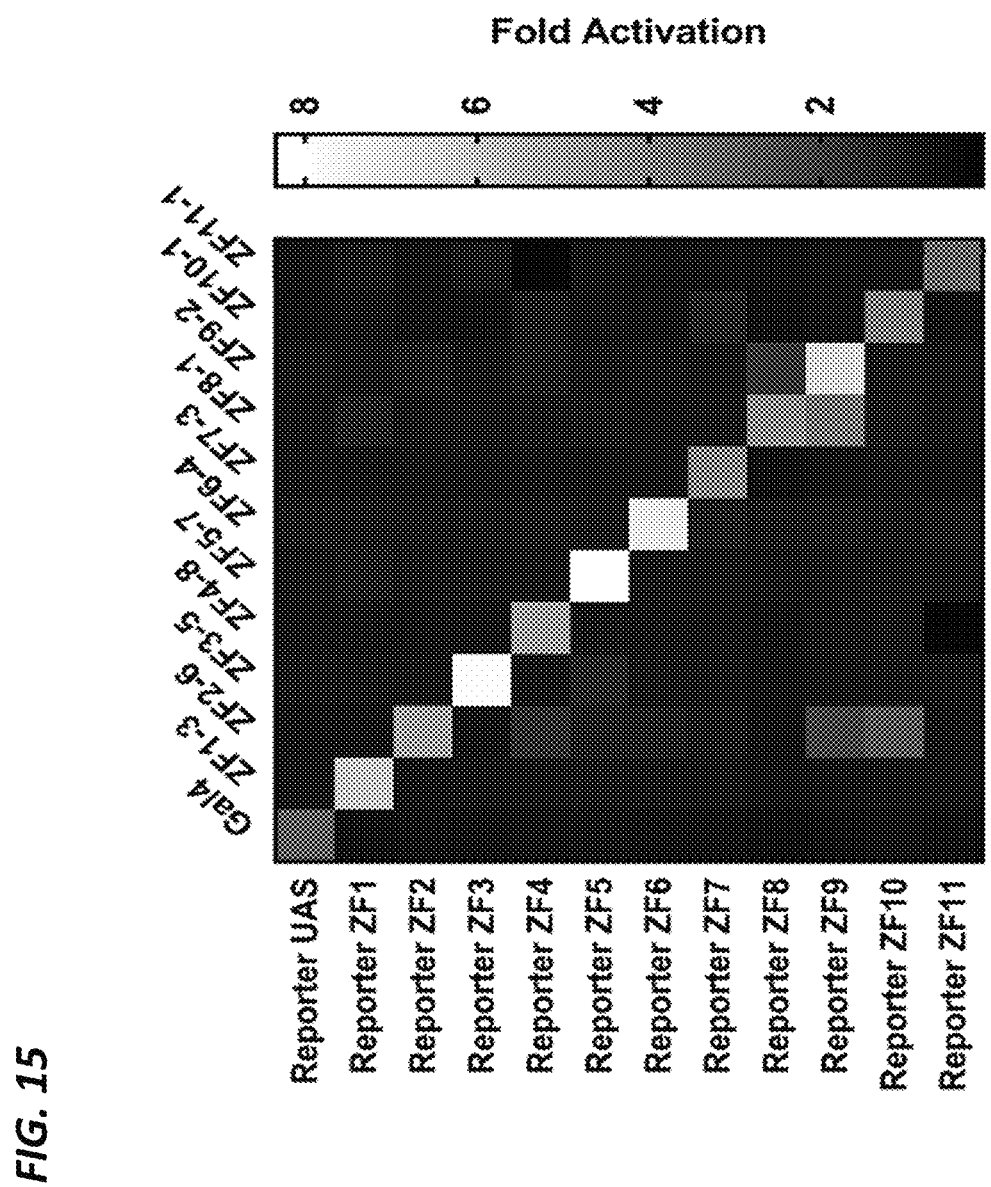
FIG. 15 demonstrates that the synTF transcriptional activators specifically activate their respective responsive promoters in genome integrated reporters in HEK293 cells (promoters consisting of 4× ZF binding sites). The synTF transcriptional activators are fusion proteins with the p65 activation domain as the effector domain. The x-axis on the top indicates the various synTF transcriptional activators having the respective ZF combination. The y-axis on the left indicates the various responsive promoters for the respective ZF protein in the synTF transcriptional activators. Experiment was done using synTFs transient transfection into stable integration reporter cell lines (AAVS1-integrated). Control experiment was conducted with Gal4 transcriptional activator and UAS responsive promoter. The ZF-containing synTF transcriptional activators were compared to the control Gal4-UAS activation.

Additionally, the inventors performed a more comprehensive and cleaner orthogonality screen. See FIG. 15 for the complied data. It differs from FIG. 8 in a few ways: (1) it includes ZF10-1 and ZF11-1 (the existing one does not have these ZF-TFs), (2) it includes Gal4 as a control, (3) each synTF is a p65 fusion, (4) 4× reporters for each line were AAVS1-integrated and the synTFs tested were transiently transfected into these lines.

The inventors also conducted genome-wide transcriptome (RNA-seq) experiments using the ZF-p65 fusions, testing for the activation of transcription. The data showed minimal genome-wide off-target gene expression events with the synTFs activators.

REFERENCES

Khalil et al., "A Synthetic Biology Framework for Programming Eukaryotic Transcription Functions", Cell 150 (2012).

Sander et al., "In silico abstraction of zinc finger nuclease cleavage profiles reveals an expanded landscape of off target sites." Nucleic Acids Res. 2013 Oct. 1; 41(19): e181.

Pattanayak V, Ramrirez C L, Joung J K, Liu D R. Revealing off-target cleavage specificities of zinc-finger nucleases by in vitro selection. Nat Methods. 2011 Aug. 7; 8(9): 765-70.

Sander J D, Dahlborg E J, Goodwin M J, Cade L, Zhang F, Cifuentes D, Curtin S J, Blackburn J S, Thibodeau-Beganny S, Qi Y, Pierick C J, Hoffman E, Macder M L, Khayter C, Reyon D, Dobbs D, Langenau D M, Stupar R M, Giraldez A J, Voytas D F, Peterson R T, Yeh J R, Joung J K. Selection-free zinc-finger-nuclease engineering by context-dependent assembly (CoDA). Nat Methods. 2010 Dec. 12; doi: 10.1038/nmeth.1542.

Sander J D, Maeder M L, Reyon L, Voytas D F, Joung J K, Dobbs D. ZiFiT (Zinc Finger Targeter): an updated zinc finger engineering tool. Nucleic Acids Res. 2010 Jul. 11; 38 Suppl:W462-8.

Maeder M L, Thibodeau-Beganny S, Sander J D, Voytas D F, Joung J K. Oligomerized Pool ENgineering (OPEN): An "Open-Source" Protocol for Making Customized Zinc Finger Arrays, Nat Protocols, 2009, 4: 1471-1501.

Maeder M L, Thibodeau-Beganny S, Osiak A, Wright D A, Anthony R M, Eichtinger M, Jiang T, Foley J E, Winfrey R J, Townsend J A, Unger-Wallace E, Sander J D, Muller-Lerch F, Fu F, Pearlberg J, Gobel C, Dassie J, Pruett-Miller S M, Porteus M H, Sgroi D C, Iafrate A J, Dobbs D, McCray P B, Cathomen T, Voytas D F, Joung J K. Rapid "open-source" engineering of customized zinc-finger nucleases for highly efficient gene modification, Mol Cell, 2008, 31: 294-301.

Garg et al., "Engineering synthetic TAL effectors with orthogonal target sites." Nucleic Acids Res. 2012

Beerli, R. R., and Barbas, C. F., III. (2002). Engineering polydactyl zinc-finger transcription factors. Nat. Biotechnol. 20, 135-141.

TABLE 1

| 6mer | # occurances in Human Genome Build 37 | 6mer | # occurances in Human Genome Build 37 |
|---|---|---|---|
| GCGACG | 44969 | GCTGTC | 1040969 |
| GACGAC | 107501 | TAAGGT | 1084864 |
| GACGAT | 143718 | GTTGGC | 1106181 |
| TGCGTA | 158568 | GACTTG | 1154843 |
| TGCGTC | 169501 | GCCTGC | 1393464 |
| TCGGAA | 179274 | GAGGGG | 1487400 |
| TCGGTG | 199414 | TAAGTG | 1529627 |
| GTCACG | 201114 | GAGTCT | 1587854 |
| GACACG | 242310 | TGGGGT | 1766352 |
| GGCGAC | 260231 | TGGGTT | 1805533 |
| GCTGCG | 279949 | GATGAA | 1971926 |
| GGCGCG | 293359 | GGAGGG | 2067820 |
| GGTGCG | 319174 | TCTGGG | 2122422 |
| GCCGCC | 347210 | GGTGGG | 2243231 |
| TCGGCT | 468698 | GTGGTG | 2406362 |
| GCGTGG | 526164 | GGCTGA | 2483117 |
| TGGGCG | 604619 | GAAGGA | 2504910 |
| GAGACG | 639756 | TGGGAA | 2570736 |
| GGTTAG | 694780 | TGGGAT | 2642429 |
| GTAGGG | 760348 | GAGGCA | 2671646 |
| GTAGGT | 866278 | GAATTT | 2827108 |
| GCCTAG | 909272 | GCTGAG | 2982694 |
| GGGTAA | 925700 | GTGTGT | 3565452 |
| TAAGGG | 947952 | GCTGGG | 3664942 |
| GATGAC | 989073 | TGTGTG | 4258659 |

We claim:

1. An engineered responsive promoter comprising (a) at least one target DNA sequence element selected from the group consisting of 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTC-GAAG-3' (SEQ ID NO: 91) and (b) a promoter sequence, wherein the at least one target DNA sequence element is operably linked at the 5' end of the promoter sequence in order to influence transcription initiation of a nearby coding sequence.

2. An engineered gene expression system for the in vivo or in vitro regulatable expression of an exogenous gene, the system comprising:
   a) an engineered zinc-finger-containing synthetic transcription factor (synTF) protein comprising two main domains: (a) a first main domain which is a DNA-binding zinc finger protein domain (ZF protein domain), and (b) a second domain through which the synTF exerts its effect (effector domain) having the formula I: [ZF protein domain]-[effector domain] or the formula IV: [effector domain]-[ZF protein domain], wherein the ZF protein domain is modular in design and is composed zinc finger arrays (ZFA), wherein there is one to ten ZFAs, wherein the ZFA comprises the sequence: N'-[(formula II)-$L_2]_{6-8}$-C', wherein formula II is that of a ZF motif and is [$X_{0-3}CX_{1-5}CX_{2-7}$-(helix)-$HX_{3-6}H$] (SEQ ID NO: 19), where the subscript 6-8 indicates the number of ZF motifs in a ZFA, wherein the ZF motifs are linked together by $L_2$, wherein $L_2$ is a linker peptide having 4-6 amino acid residues, and wherein N'- and C'- indicates the N-terminus and C-terminus, respectively, of the sequence, and b) an engineered responsive promoter comprising
   i) at least one orthogonal target DNA sequence element selected from the group consisting of 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGAC-GACG-3' (SEQ ID NO: 89), 5'-CGGCGTAGC-CGATGTCGCGC-3' (SEQ ID NO: 90), and 5'-GGTCGTTGCGGTAGTCGAAG-3' (SEQ ID NO: 91), and,
   ii) a promoter sequence, wherein the at least one target DNA sequence element is operably linked to the 5' end of the promoter sequence in order to influence transcription initiation of a nearby coding sequence, wherein the influence is to upregulate or downregulate transcription initiation, and wherein the gene is operably linked to the promoter in the engineered responsive promoter,
   wherein the ZFA of the synTF is capable of binding the at least one orthogonal target DNA sequence element in the engineered responsive promoter.

3. The system of claim 2, wherein formula II is [$X_3CX_2CX_5$-(helix)-$HX_3H$] (SEQ ID NO: 20).

4. The system of claim 2, wherein all of the helices of each ZFA or at least four of the helices in each ZFA comprise a sequence selected from the group consisting of: SEQ ID NO: 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80.

5. The system of claim 2, wherein the effector domain of the synTF is a transcription activating domain, or a transcription repressor domain, or an epigenetic effector domain.

6. The system of claim 2, wherein the ZFA of the synTF comprises, consists of, or consist essentially of ZF motif helices selected from the group consisting of: SEQ ID NO: 22, 23, 24, 25, 26, 27, 28, 29, and 30, and the ZFA is capable of binding the sequence of SEQ ID NO: 81.

7. The system of claim 2, wherein the ZFA of the synTF comprises, consists of, or consist essentially of ZF motif helices selected from the group consisting of: SEQ ID NO: 31, 32, 33, 34, 35, 36, 37, 38 and 39, and the ZFA is capable of binding the sequence of SEQ ID NO: 82.

8. The system of claim 2, wherein the ZFA of the synTF comprises, consists of, or consist essentially of ZF motif helices selected from the group consisting of: SEQ ID NO: 31, 38, 40, 41, 42, 43, 44, and 45, and the ZFA is capable of binding the sequence of SEQ ID NO: 83.

9. The system of claim 2, wherein the ZFA of the synTF comprises, consists of, or consist essentially of ZF motif helices selected from the group consisting of: SEQ ID NO: 26, 35, 36, 46, 47, 40, 48, 49, 50, and 51, and the ZFA is capable of binding the sequence of SEQ ID NO: 84.

10. The system of claim 2, wherein the ZFA of the synTF comprises, consists of, or consist essentially of ZF motif helices selected from the group consisting of: SEQ ID NO: 52, 53, 54, 55, 56, 57, 58, and 59, and the ZFA is capable of binding the sequence of SEQ ID NO: 85.

11. The system of claim 2, wherein the ZFA of the synTF comprises, consists of, or consist essentially of ZF motif helices selected from the group consisting of: SEQ ID NO: 26, 30, 35, 36, 48, 49, 60, 61, 62, and 63, and the ZFA is capable of binding the sequence of SEQ ID NO: 86.

12. The system of claim 2, wherein the ZFA of the synTF comprises, consists of, or consist essentially of ZF motif helices selected from the group consisting of: SEQ ID NO: 30, 31, 49, 64, 65, 66, 67, 68, and 69, and the ZFA is capable of binding the sequence of SEQ ID NO: 87.

13. The system of claim 2, wherein the ZFA of the synTF comprises, consists of, or consist essentially of ZF motif helices selected from the group consisting of: SEQ ID NO: 30, 31, 49, 70, 71, 72, 73, and 74, and the ZFA is capable of binding the sequence of SEQ ID NO: 88.

14. The system of claim 2, wherein the ZFA of the synTF comprises, consists of, or consist essentially of ZF motif helices selected from the group consisting of: SEQ ID NO: 31, 35, 36, 48, 49, 71, and 72, and the ZFA is capable of binding the sequence of SEQ ID NO: 89.

15. The system of claim 2, wherein the ZFA of the synTF comprises, consists of, or consist essentially of a ZFA helix combo, comprising ZF 10, selected from the group consisting of: SEQ ID NO: 30, 31, 47, 50, 75 and 76, and the at least one ZFA is capable of binding the sequence of SEQ ID NO: 90.

16. The system of claim 2, wherein the ZFA of the synTF comprises, consists of, or consist essentially of a ZFA helix combo, ZF 11-1, selected from the group consisting of: SEQ ID NO: 31, 63, 77, 78, 79, and 80, and the at least one ZFA is capable of binding the sequence of SEQ ID NO: 91.

17. A method of regulating gene activation or repression comprising contacting a cell with an engineered gene expression system of claim 2.

18. A kit for regulating gene activation or repression, the kit comprising an engineered expression system comprising
   a) an engineered zinc-finger-containing synthetic transcription factor (synTF) protein comprising two main domains: (a) a first main domain which is a DNA-binding zinc finger protein domain (ZF protein domain), and (b) a second domain through which the synTF exerts its effect (effector domain) having the formula I: [ZF protein domain]-[effector domain] or the formula IV: [effector domain]-[ZF protein domain], wherein the ZF protein domain is modular in design and is composed zinc finger arrays (ZFA), wherein there is one to ten ZFAs, wherein the ZFA comprises the sequence: N'-[(formula II)-$L_2]_{6-8}$-C', wherein formula II is that of a ZF motif and is [$X_{0-3}CX_{1-5}CX_{2-7}$-(helix)-$HX_{3-6}H$] (SEQ ID NO: 19), where the subscript 6-8 indicates the number of ZF motifs in a ZFA, wherein the ZF motifs are linked together by $L_2$, wherein L$_2$ is a linker peptide having 4-6 amino acid residues, and wherein N'- and C'- indicates the N-terminus and C-terminus, respectively, of the sequence, and b) an engineered responsive promoter comprising
   i) at least one orthogonal target DNA sequence element selected from the group consisting of 5'-CGTCGAAGTCGAAGTCGACC-3' (SEQ ID NO: 81), 5'-GGACGACGTTACGGACGTAC-3' (SEQ ID NO: 82), 5'-A GACGTCGAAGTAGCCGTAG-3' (SEQ ID NO: 83), 5'-GGACGACGCCGATGTAGAAG-3' (SEQ ID NO: 84), 5'-TGAAGCAGTCGACGCCGAAG-3' (SEQ ID NO: 85), 5'-GGACGACGCGGTCTAAGAAG-3' (SEQ ID NO: 86), 5'-CGACGAGGTCGCATAAGTAG-3' (SEQ ID NO: 87), 5'-AGACGCAGTATAGGTCGAAC-3' (SEQ ID NO: 88), 5'-AGACGCAGTATAGGACGACG-3' (SEQ ID NO: 89), 5'-CGGCGTAGCCGATGTCGCGC-3' (SEQ ID NO: 90), and 5'-GGTCGTTGCGGTAGTCGAAG-3' (SEQ ID NO: 91), and
   ii) a promoter sequence, wherein the at least one target DNA sequence element is operably linked to the 5' end of the promoter sequence in order to influence transcription initiation of a nearby coding sequence, wherein the influence is to upregulate or downregulate transcription initiation, and wherein the gene is operably linked to the promoter in the engineered responsive promoter,
   wherein the ZFA of the synTF is capable of binding the at least one orthogonal target DNA sequence element in the engineered responsive promoter, and c) reagents and instructions for use thereof.

* * * * *

SEQUENCE LISTING

<160> NUMBER OF SEQ ID NOS: 153

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Thr Gly Gly Gly Glu Lys Pro
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Thr Gly Glu Lys Pro

```
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Gly Ser Gln Lys Pro
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Gly Glu Arg
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Gly Ser Gln Lys
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr His Leu Arg
1

<210> SEQ ID NO 7
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
                20                  25                  30

Leu Leu Asn Ile Asp Lys Asp Ile Arg Lys Ile Leu Ser Gly Tyr Ile
            35                  40                  45

Val Glu Ile Glu Asp Thr Glu
```

```
                50                  55

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Glu Ile Glu Asp Thr Glu
1               5

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Asp Ile Arg Lys Ile Leu Ser Gly Tyr Ile Val Glu Ile Glu Asp
1               5                   10                  15

Thr Glu

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Thr Glu Gly Leu Leu Leu Asn Ile Asp Lys Asp Ile Arg Lys Ile
1               5                   10                  15

Leu Ser Gly Tyr Ile Val Glu Ile Glu Asp Thr Glu
            20                  25

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Val Lys Gln Glu Asn Arg Leu Leu Asn Glu Ser Glu Ser
1               5                   10

<210> SEQ ID NO 12
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Gly Ala Asp Glu Ser Val Val Lys Glu Ala His Arg Glu Val Ile
1               5                   10                  15

Asn Ser Ser Thr Glu Gly Leu Leu Leu Asn Ile Asp Lys Asp Ile Arg
            20                  25                  30
```

```
Lys Ile Leu Ser Gly Tyr Ile Val Glu Ile Glu Asp Thr Glu
        35                  40                  45

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Ser Gly Gly Ser
1               5

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(24)
<223> OTHER INFORMATION: This sequence may encompass 1-8 "Gly Gly Ser"
      repeating units
<220> FEATURE:
<223> OTHER INFORMATION: See specification as filed for detailed
      description of substitutions and preferred embodiments

<400> SEQUENCE: 14

Gly Gly Ser Gly Gly Ser Gly Gly Ser Gly Gly Ser Gly Gly Ser Gly
1               5                   10                  15

Gly Ser Gly Gly Ser Gly Gly Ser
            20

<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-8 "Gly Gly Gly
      Gly Ser"
      repeating units
<220> FEATURE:
<223> OTHER INFORMATION: See specification as filed for detailed
      description of substitutions and preferred embodiments

<400> SEQUENCE: 15

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 16

Gly Gly Gly Gly Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Ser Gly Gly Ser
1               5

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(17)
<223> OTHER INFORMATION: Any amino acid
<220> FEATURE:
<221> NAME/KEY: MOD_RES
<222> LOCATION: (19)..(21)
<223> OTHER INFORMATION: Any amino acid

<400> SEQUENCE: 18

Xaa Xaa Cys Xaa Xaa Cys Xaa Xaa Xaa Xaa Xaa Xaa Xaa Xaa Xaa Xaa
1               5                   10                  15

Xaa His Xaa Xaa Xaa His
            20

<210> SEQ ID NO 19
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MISC_FEATURE
<222> LOCATION: (1)..(3)
<223> OTHER INFORMATION: This region may encompass 0-3 residues
<220> FEATURE:
<221> NAME/KEY: MOD_RES
<222> LOCATION: (5)..(9)
<223> OTHER INFORMATION: Any amino acid
<220> FEATURE:
<221> NAME/KEY: MISC_FEATURE
<222> LOCATION: (5)..(9)
<223> OTHER INFORMATION: This region may encompass 1-5 residues
<220> FEATURE:
```

```
<221> NAME/KEY: MOD_RES
<222> LOCATION: (11)..(17)
<223> OTHER INFORMATION: Any amino acid
<220> FEATURE:
<221> NAME/KEY: MISC_FEATURE
<222> LOCATION: (11)..(17)
<223> OTHER INFORMATION: This region may encompass 2-7 residues
<220> FEATURE:
<221> NAME/KEY: MOD_RES
<222> LOCATION: (18)..(23)
<223> OTHER INFORMATION: Any amino acid
<220> FEATURE:
<221> NAME/KEY: MOD_RES
<222> LOCATION: (25)..(30)
<223> OTHER INFORMATION: Any amino acid
<220> FEATURE:
<221> NAME/KEY: MISC_FEATURE
<222> LOCATION: (25)..(30)
<223> OTHER INFORMATION: This region may encompass 3-6 residues

<400> SEQUENCE: 19

Xaa Xaa Xaa Cys Xaa Xaa Xaa Xaa Xaa Cys Xaa Xaa Xaa Xaa Xaa Xaa
1               5                   10                  15

Xaa Xaa Xaa Xaa Xaa Xaa Xaa His Xaa Xaa Xaa Xaa Xaa Xaa His
            20                  25                  30

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid

<400> SEQUENCE: 20

Xaa Xaa Xaa Cys Xaa Xaa Cys Xaa Xaa Xaa Xaa Xaa Xaa Xaa Xaa Xaa
1               5                   10                  15

Xaa Xaa His Xaa Xaa Xaa His
            20

<210> SEQ ID NO 21
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(22)
<223> OTHER INFORMATION: Any amino acid
<220> FEATURE:
<221> NAME/KEY: MOD_RES
<222> LOCATION: (44)..(49)
<223> OTHER INFORMATION: Any amino acid
<220> FEATURE:
<221> NAME/KEY: MOD_RES
```

<222> LOCATION: (72)..(77)
<223> OTHER INFORMATION: Any amino acid
<220> FEATURE:
<221> NAME/KEY: MOD_RES
<222> LOCATION: (99)..(104)
<223> OTHER INFORMATION: Any amino acid
<220> FEATURE:
<221> NAME/KEY: MOD_RES
<222> LOCATION: (127)..(132)
<223> OTHER INFORMATION: Any amino acid
<220> FEATURE:
<221> NAME/KEY: MOD_RES
<222> LOCATION: (154)..(159)
<223> OTHER INFORMATION: Any amino acid

<400> SEQUENCE: 21

Pro Gly Glu Arg Pro Phe Gln Cys Arg Ile Cys Met Arg Asn Phe Ser
1               5                   10                  15

Xaa Xaa Xaa Xaa Xaa Xaa His Thr Arg Thr His Thr Gly Glu Lys Pro
            20                  25                  30

Phe Gln Cys Arg Ile Cys Met Arg Asn Phe Ser Xaa Xaa Xaa Xaa Xaa
        35                  40                  45

Xaa His Leu Arg Thr His Thr Gly Ser Gln Lys Pro Phe Gln Cys Arg
    50                  55                  60

Ile Cys Met Arg Asn Phe Ser Xaa Xaa Xaa Xaa Xaa Xaa His Thr Arg
65                  70                  75                  80

Thr His Thr Gly Glu Lys Pro Phe Gln Cys Arg Ile Cys Met Arg Asn
                85                  90                  95

Phe Ser Xaa Xaa Xaa Xaa Xaa Xaa His Leu Arg Thr His Thr Gly Ser
            100                 105                 110

Gln Lys Pro Phe Gln Cys Arg Ile Cys Met Arg Asn Phe Ser Xaa Xaa
        115                 120                 125

Xaa Xaa Xaa Xaa His Thr Arg Thr His Thr Gly Glu Lys Pro Phe Gln
    130                 135                 140

Cys Arg Ile Cys Met Arg Asn Phe Ser Xaa Xaa Xaa Xaa Xaa Xaa His
145                 150                 155                 160

Leu Arg Thr His Leu Arg
                165

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Glu Ala Asn Leu Arg Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Pro Ser Val Leu Lys Arg
1               5

```
<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Ala Asn Leu Leu Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Pro Ser Ser Leu Lys Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Thr Asn Leu Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ala Thr Gln Leu Val Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Arg Arg Ser Leu Ala Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

```
Glu Glu Ala Asn Leu Arg Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp His Ser Ser Leu Lys Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Arg Ser Ser Leu Val Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Met Gly Asn Leu Gly Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser His Asp Leu Thr Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Lys Ser Ser Leu Thr Arg
1               5

<210> SEQ ID NO 35
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Asp Ser Ser Asn Leu Arg Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Gln Gly Asn Leu Ile Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Lys Gln Ala Leu Thr Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Arg Gly Asn Leu Thr Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser His Asp Leu Thr Val
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Lys Ser Val Leu Ala Arg
1               5
```

```
<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Thr Asn Asn Leu Gly Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr His Ala Val Leu Thr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Lys Ser Leu Leu Ala Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Lys Gln Ala Leu Asp Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Thr Ser Val Leu Asn Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 46

Gln Gly Thr Ser Leu Ala Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Arg His Asn Leu Thr Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Lys Gln Asn Leu Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Pro Ser Asn Leu Arg Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp His Ser Asn Leu Ser Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ser Thr Ser Leu Gln Arg
1               5

<210> SEQ ID NO 52
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 52

Asn Met Ser Asn Leu Thr Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Ser Val Leu Arg Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Gln Glu Asn Leu Thr Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Arg Ser Ser Leu Arg Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ser Gly Thr Leu His Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Leu Ala Asn Leu Ala Arg
1               5
```

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Gln Thr Thr Leu Arg Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Pro Ser Asn Leu Ala Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gly Gly Asn Leu Ala Leu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ala Asp Met Leu Arg Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Lys Ala Asn Leu Gly Val
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 63

Arg Leu Asp Met Leu Ala Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Arg Gly Asn Leu Asn Met
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Pro Gln Glu Leu Arg Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Gln Asp Asn Leu Gly Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Gly Gly Asn Leu Gly Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Gly Asn Leu Gln Leu
1               5

<210> SEQ ID NO 69
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Arg Gln Glu Leu Thr Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ala Ser Asn Leu Thr Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ala His Asn Leu Leu Leu
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ser Thr Thr Leu Lys Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gly Thr Thr Leu Lys Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Arg Ser Asn Leu Ala Arg
```

```
<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Arg His Gly Leu Asp Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Ser Gly His Leu Lys Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Leu Ser Asn Leu Thr Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Arg Ser Ser Leu Lys Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Arg His Ser Leu Thr Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 80

Glu Ser Gly Ala Leu Arg Arg
1               5

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cgtcgaagtc gaagtcgacc                                                     20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ggacgacgtt acggacgtac                                                     20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
agacgtcgaa gtagccgtag                                                     20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggacgacgcc gatgtagaag                                                     20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tgaagcagtc gacgccgaag                                                     20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
ggacgacgcg gtctaagaag                                               20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cgacgaggtc gcataagtag                                               20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
agacgcagta taggtcgaac                                               20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
agacgcagta taggacgacg                                               20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cggcgtagcc gatgtcgcgc                                               20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggtcgttgcg gtagtcgaag                                               20

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 92

Thr Gly Ser Lys Pro
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Gly Gln Lys Pro
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Gly Gly Lys Pro
1               5

<210> SEQ ID NO 95
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Arg Ala Asp Ala Leu Asp Asp Phe Asp Leu Asp Met Leu Gly Ser
1               5                   10                  15

Asp Ala Leu Asp Asp Phe Asp Leu Asp Met Leu Gly Ser Asp Ala Leu
            20                  25                  30

Asp Asp Phe Asp Leu Asp Met Leu Gly Ser Asp Ala Leu Asp Asp Phe
        35                  40                  45

Asp Leu Asp Met Leu
    50

<210> SEQ ID NO 96
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Glu Phe Pro Thr Met Val Phe Pro Ser Gly Gln Ile Ser Gln Ala
1               5                   10                  15

Ser Ala Leu Ala Pro Ala Pro Pro Gln Val Leu Pro Gln Ala Pro Ala
            20                  25                  30

Pro Ala Pro Ala Pro Ala Met Val Ser Ala Leu Ala Gln Ala Pro Ala
        35                  40                  45

Pro Val Pro Val Leu Ala Pro Gly Pro Pro Gln Ala Val Ala Pro Pro
    50                  55                  60
```

```
Ala Pro Lys Pro Thr Gln Ala Gly Glu Gly Thr Leu Ser Glu Ala Leu
 65                  70                  75                  80

Leu Gln Leu Gln Phe Asp Glu Asp Leu Gly Ala Leu Leu Gly Asn
             85                  90                  95

Ser Thr Asp Pro Ala Val Phe Thr Asp Leu Ala Ser Val Asp Asn Ser
            100                 105                 110

Glu Phe Gln Gln Leu Leu Asn Gln Gly Ile Pro Val Ala Pro His Thr
            115                 120                 125

Thr Glu Pro Met Leu Met Glu Tyr Pro Glu Ala Ile Thr Arg Leu Val
            130                 135                 140

Thr Gly Ala Gln Arg Pro Pro Asp Pro Ala Pro Ala Pro Leu Gly Ala
145                 150                 155                 160

Pro Gly Leu Pro Asn Gly Leu Leu Ser Gly Asp Glu Asp Phe Ser Ser
                165                 170                 175

Ile Ala Asp Met Asp Phe Ser Ala Leu Leu Ser Gln Ile Ser Ser
                180                 185                 190

<210> SEQ ID NO 97
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
                20                  25                  30

Thr Ala Gln Gln Ile Leu Tyr Arg Asn Val Met Leu Glu Asn Tyr Lys
            35                  40                  45

Asn Leu Val Ser Leu Gly Tyr Gln Leu Thr Lys Pro Asp Val Ile Leu
        50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

Val

<210> SEQ ID NO 98
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Lys Lys Arg Glu Gln Ser Asn Asp Ile Ala Arg Gly Phe Glu Arg
1               5                   10                  15

Gly Leu Glu Pro Glu Lys Ile Ile Gly Ala Thr Asp Ser Cys Gly Asp
                20                  25                  30

Leu Met Phe Leu Met Lys Trp Lys Asp Thr Asp Glu Ala Asp Leu Val
            35                  40                  45

Leu Ala Lys Glu Ala Asn Val Lys Cys Pro Gln Ile Val Ile Ala Phe
        50                  55                  60
```

Tyr Glu Glu Arg Leu Thr Trp His Ala Tyr Pro Glu Asp Ala Glu Asn
65                  70                  75                  80

Lys Glu Lys

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Gly Glu Lys Pro
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Ser Lys Pro
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Gly Gln Lys Pro
1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Gly Gly Lys Pro
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Gly Gly Gly Gly Ser Gln Lys Pro
1               5

<210> SEQ ID NO 104
<211> LENGTH: 24
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 104
gtcgacgtat cagtcgcctc ggaa                                            24

<210> SEQ ID NO 105
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
attcgtaaga ggctcactct cccttacacg gagtggataa ctagttaggc gtgtacggtg     60
ggaggcctat ataagcagag ctcgtttagt gaaccgtcag atcgcctgga acgcgtaccg    120
gtgtcgccac c                                                         131

<210> SEQ ID NO 106
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtcgaccggg tttcgtaaca atcgcatgag gattcgcaac gcctt                     45

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tcccgtctca gtaaaggt                                                   18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aatcggactg ccttcgta                                                   18

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gtatcagtcg cctcggaa                                                   18
```

<210> SEQ ID NO 110
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
attcgtaaga ggctcactct cccttacacg gagtggataa ctagttaggc gtgtacggtg     60
ggaggcctat ataagcagag ctcgtttagt gaaccgtcag atcgcctgga acgcgtaccg    120
gtgtcgccac c                                                         131

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cctttccacg atcatgtgc                                                  19

<210> SEQ ID NO 112
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
agtaatacca ccactgcgac cctagatcgg agatccaatt agatccatga tccgaaac      58

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtgtcgcacg tatcacttga tcggcaaa                                        28

<210> SEQ ID NO 114
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ttgcttcctc                                                            10

<210> SEQ ID NO 115
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115

```
gaggtagatc aggcca                                                 16

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ttgcgctgcc tagatcatcg ttggc                                       25

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
acagatcgag atctttggt                                              19

<210> SEQ ID NO 118
<211> LENGTH: 775
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
tccatagtga gttctgatcg tgtcacggct agccgatgtc gcgctaggat cgaggatcat    60
ctctgatctg ttttaggact agtgcatgcg cgttgacatt gattattgac tagttattaa   120
tagtaatcaa ttacggggtc attagttcat agcccatata tggagttccg cgttacataa   180
cttacggtaa atggcccgcc tggctgaccg cccaacgacc cccgcccatt gacgtcaata   240
atgacgtatg ttcccatagt aacgccaata gggactttcc attgacgtca atgggtggag   300
tatttacggt aaactgccca cttggcagta catcaagtgt atcatatgcc aagtacgccc   360
cctattgacg tcaatgacgg taaatggccc gcctggcatt atgcccagta catgacctta   420
tgggactttc ctacttggca gtacatctac gtattagtca tcgctattac catggtgatg   480
cggttttggc agtacatcaa tgggcgtgga tagcggtttg actcacgggg atttccaagt   540
ctccacccca ttgacgtcaa tgggagtttg ttttggcacc aaaatcaacg ggactttcca   600
aaatgtcgta caactccgcc ccattgacg caaatgggcg gtaggcgtgt acggtgggag   660
gtctatataa gcagagctct ctggctaact agagaaccca ctgcttactg gcttatcgaa   720
attaatacga ctcactatag ggagacccaa gctgacgcgt accggtgtcg ccacc        775

<210> SEQ ID NO 119
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gtcgaccggg tttcgtaaca atcgcatgag gattcgcaac gcctt                  45
```

```
<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gactgttgcg aacgattc                                                  18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tcccgtctca gtaaaggt                                                  18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
aatcggactg ccttcgta                                                  18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gtatcagtcg cctcggaa                                                  18

<210> SEQ ID NO 124
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
attcgtaaga ggctcactct cccttacacg gagtggataa ctagttaggc gtgtacggtg    60
ggaggcctat ataagcagag ctcgtttagt gaaccgtcag atcgcctgga acgcgtaccg   120
gtgtcgccac c                                                       131

<210> SEQ ID NO 125
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(24)
```

<223> OTHER INFORMATION: Any amino acid
<220> FEATURE:
<221> NAME/KEY: MOD_RES
<222> LOCATION: (46)..(51)
<223> OTHER INFORMATION: Any amino acid
<220> FEATURE:
<221> NAME/KEY: MOD_RES
<222> LOCATION: (74)..(79)
<223> OTHER INFORMATION: Any amino acid
<220> FEATURE:
<221> NAME/KEY: MOD_RES
<222> LOCATION: (101)..(106)
<223> OTHER INFORMATION: Any amino acid
<220> FEATURE:
<221> NAME/KEY: MOD_RES
<222> LOCATION: (129)..(134)
<223> OTHER INFORMATION: Any amino acid
<220> FEATURE:
<221> NAME/KEY: MOD_RES
<222> LOCATION: (156)..(161)
<223> OTHER INFORMATION: Any amino acid

<400> SEQUENCE: 125

Ser Arg Pro Gly Glu Arg Pro Phe Gln Cys Arg Ile Cys Met Arg Asn
1               5                   10                  15

Phe Ser Xaa Xaa Xaa Xaa Xaa Xaa His Thr Arg Thr His Thr Gly Glu
            20                  25                  30

Lys Pro Phe Gln Cys Arg Ile Cys Met Arg Asn Phe Ser Xaa Xaa Xaa
        35                  40                  45

Xaa Xaa Xaa His Leu Arg Thr His Thr Gly Ser Gln Lys Pro Phe Gln
50                  55                  60

Cys Arg Ile Cys Met Arg Asn Phe Ser Xaa Xaa Xaa Xaa Xaa Xaa His
65                  70                  75                  80

Leu Arg Thr His Thr Gly Glu Lys Pro Phe Gln Cys Arg Ile Cys Met
                85                  90                  95

Arg Asn Phe Ser Xaa Xaa Xaa Xaa Xaa Xaa His Leu Lys Thr His Thr
            100                 105                 110

Gly Ser Gln Lys Pro Phe Gln Cys Arg Ile Cys Met Arg Asn Phe Ser
            115                 120                 125

Xaa Xaa Xaa Xaa Xaa Xaa His Leu Arg Thr His Thr Gly Glu Lys Pro
130                 135                 140

Phe Gln Cys Arg Ile Cys Met Arg Asn Phe Ser Xaa Xaa Xaa Xaa Xaa
145                 150                 155                 160

Xaa His Leu Arg Thr His Leu Arg Gly Ser
                165                 170

<210> SEQ ID NO 126
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(24)
<223> OTHER INFORMATION: Any amino acid
<220> FEATURE:
<221> NAME/KEY: MOD_RES
<222> LOCATION: (46)..(51)
<223> OTHER INFORMATION: Any amino acid
<220> FEATURE:
<221> NAME/KEY: MOD_RES
<222> LOCATION: (74)..(79)
<223> OTHER INFORMATION: Any amino acid
<220> FEATURE:
<221> NAME/KEY: MOD_RES
<222> LOCATION: (101)..(106)
<223> OTHER INFORMATION: Any amino acid
<220> FEATURE:
<221> NAME/KEY: MOD_RES
<222> LOCATION: (129)..(134)
<223> OTHER INFORMATION: Any amino acid
<220> FEATURE:
<221> NAME/KEY: MOD_RES
<222> LOCATION: (156)..(161)
<223> OTHER INFORMATION: Any amino acid

<400> SEQUENCE: 126

Ser Arg Pro Gly Glu Arg Pro Phe Gln Cys Arg Ile Cys Met Arg Asn
1               5                   10                  15

Phe Ser Xaa Xaa Xaa Xaa Xaa Xaa His Thr Arg Thr His Thr Gly Glu
            20                  25                  30

Lys Pro Phe Gln Cys Arg Ile Cys Met Arg Asn Phe Ser Xaa Xaa Xaa
            35                  40                  45

Xaa Xaa Xaa His Leu Arg Thr His Thr Gly Ser Gln Lys Pro Phe Gln
50                  55                  60

Cys Arg Ile Cys Met Arg Asn Phe Ser Xaa Xaa Xaa Xaa Xaa Xaa His
65                  70                  75                  80

Thr Arg Thr His Thr Gly Glu Lys Pro Phe Gln Cys Arg Ile Cys Met
                85                  90                  95

Arg Asn Phe Ser Xaa Xaa Xaa Xaa Xaa Xaa His Leu Arg Thr His Thr
                100                 105                 110

Gly Ser Gln Lys Pro Phe Gln Cys Arg Ile Cys Met Arg Asn Phe Ser
            115                 120                 125

Xaa Xaa Xaa Xaa Xaa Xaa His Thr Arg Thr His Thr Gly Glu Lys Pro
    130                 135                 140

Phe Gln Cys Arg Ile Cys Asn Cys Asn Phe Ser Xaa Xaa Xaa Xaa Xaa
145                 150                 155                 160

Xaa His Leu Arg Thr His Leu Arg Gly Ser
                165                 170

<210> SEQ ID NO 127
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(40)
<223> OTHER INFORMATION: Any amino acid
<220> FEATURE:
<221> NAME/KEY: MOD_RES
<222> LOCATION: (62)..(67)
<223> OTHER INFORMATION: Any amino acid
<220> FEATURE:
<221> NAME/KEY: MOD_RES
<222> LOCATION: (90)..(95)
<223> OTHER INFORMATION: Any amino acid
<220> FEATURE:
<221> NAME/KEY: MOD_RES
<222> LOCATION: (117)..(122)
<223> OTHER INFORMATION: Any amino acid
<220> FEATURE:
<221> NAME/KEY: MOD_RES
<222> LOCATION: (145)..(150)
<223> OTHER INFORMATION: Any amino acid
<220> FEATURE:
<221> NAME/KEY: MOD_RES
<222> LOCATION: (172)..(177)
<223> OTHER INFORMATION: Any amino acid

<400> SEQUENCE: 127

Met Phe Glu Pro Lys Lys Arg Lys Val Phe Glu Gly Thr Ala Ser
1               5                   10                  15

Ser Arg Pro Gly Glu Arg Pro Phe Gln Cys Arg Ile Cys Met Arg Asn
            20                  25                  30

Phe Ser Xaa Xaa Xaa Xaa Xaa His Thr Arg Thr His Thr Gly Glu
        35                  40                  45

Lys Pro Phe Gln Cys Arg Ile Cys Met Arg Asn Phe Ser Xaa Xaa Xaa
50                  55                  60

Xaa Xaa Xaa His Leu Arg Thr His Thr Gly Ser Gln Lys Pro Phe Gln
65                  70                  75                  80

Cys Arg Ile Cys Met Arg Asn Phe Ser Xaa Xaa Xaa Xaa Xaa His
                85                  90                  95

Leu Arg Thr His Thr Gly Glu Lys Pro Phe Gln Cys Arg Ile Cys Met
            100                 105                 110

Arg Asn Phe Ser Xaa Xaa Xaa Xaa Xaa Xaa His Leu Lys Thr His Thr
                115                 120                 125

Gly Ser Gln Lys Pro Phe Gln Cys Arg Ile Cys Met Arg Asn Phe Ser
130                 135                 140

Xaa Xaa Xaa Xaa Xaa Xaa His Leu Arg Thr His Thr Gly Glu Lys Pro
145                 150                 155                 160

Phe Gln Cys Arg Ile Cys Met Arg Asn Phe Ser Xaa Xaa Xaa Xaa Xaa
                165                 170                 175

Xaa His Leu Arg Thr His Leu Arg Gly Ser Thr Cys Arg Gly Arg Ala
        180                 185                 190

Asp Ala Leu Asp Asp Phe Asp Leu Asp Met Leu Gly Ser Asp Ala Leu
            195                 200                 205

Asp Asp Phe Asp Leu Asp Met Leu Gly Ser Asp Ala Leu Asp Asp Phe
210                 215                 220

Asp Leu Asp Met Leu Gly Ser Asp Ala Leu Asp Asp Phe Asp Leu Asp
225                 230                 235                 240

Met Leu

<210> SEQ ID NO 128
<211> LENGTH: 285
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (134)..(139)
<223> OTHER INFORMATION: Any amino acid
<220> FEATURE:
<221> NAME/KEY: MOD_RES
<222> LOCATION: (161)..(166)
<223> OTHER INFORMATION: Any amino acid
<220> FEATURE:
<221> NAME/KEY: MOD_RES
<222> LOCATION: (189)..(194)
<223> OTHER INFORMATION: Any amino acid
<220> FEATURE:
<221> NAME/KEY: MOD_RES
<222> LOCATION: (216)..(221)
<223> OTHER INFORMATION: Any amino acid
<220> FEATURE:
<221> NAME/KEY: MOD_RES
<222> LOCATION: (244)..(249)
<223> OTHER INFORMATION: Any amino acid
<220> FEATURE:
<221> NAME/KEY: MOD_RES
<222> LOCATION: (271)..(276)
<223> OTHER INFORMATION: Any amino acid

<400> SEQUENCE: 128

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
            20                  25                  30

Thr Ala Gln Gln Ile Leu Tyr Arg Asn Val Met Leu Glu Asn Tyr Lys
        35                  40                  45

Asn Leu Val Ser Leu Gly Tyr Gln Leu Thr Lys Pro Asp Val Ile Leu
    50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

Val Pro Lys Lys Lys Arg Lys Val Leu Glu Gly Gly Gly Gly Ser Gly
            100                 105                 110

Thr Cys Arg Ser Arg Pro Gly Glu Arg Pro Phe Gln Cys Arg Ile Cys
        115                 120                 125

Met Arg Asn Phe Ser Xaa Xaa Xaa Xaa Xaa Xaa His Thr Arg Thr His
    130                 135                 140

Thr Gly Glu Lys Pro Phe Gln Cys Arg Ile Cys Met Arg Asn Phe Ser
145                 150                 155                 160

Xaa Xaa Xaa Xaa Xaa Xaa His Leu Arg Thr His Thr Gly Ser Gln Lys
                165                 170                 175

Pro Phe Gln Cys Arg Ile Cys Met Arg Asn Phe Ser Xaa Xaa Xaa Xaa
            180                 185                 190

Xaa Xaa His Leu Arg Thr His Thr Gly Glu Lys Pro Phe Gln Cys Arg
        195                 200                 205

Ile Cys Met Arg Asn Phe Ser Xaa Xaa Xaa Xaa Xaa Xaa His Leu Lys
    210                 215                 220

Thr His Thr Gly Ser Gln Lys Pro Phe Gln Cys Arg Ile Cys Met Arg
225                 230                 235                 240

Asn Phe Ser Xaa Xaa Xaa Xaa Xaa Xaa His Leu Arg Thr His Thr Gly
                245                 250                 255

Glu Lys Pro Phe Gln Cys Arg Ile Cys Met Arg Asn Phe Ser Xaa Xaa
            260                 265                 270

Xaa Xaa Xaa Xaa His Leu Arg Thr His Leu Arg Gly Ser
        275                 280                 285

<210> SEQ ID NO 129
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (122)..(127)
<223> OTHER INFORMATION: Any amino acid
<220> FEATURE:
<221> NAME/KEY: MOD_RES
<222> LOCATION: (149)..(154)
<223> OTHER INFORMATION: Any amino acid
<220> FEATURE:
<221> NAME/KEY: MOD_RES
<222> LOCATION: (177)..(182)
<223> OTHER INFORMATION: Any amino acid -continued

```
<220> FEATURE:
<221> NAME/KEY: MOD_RES
<222> LOCATION: (204)..(209)
<223> OTHER INFORMATION: Any amino acid
<220> FEATURE:
<221> NAME/KEY: MOD_RES
<222> LOCATION: (232)..(237)
<223> OTHER INFORMATION: Any amino acid
<220> FEATURE:
<221> NAME/KEY: MOD_RES
<222> LOCATION: (259)..(264)
<223> OTHER INFORMATION: Any amino acid

<400> SEQUENCE: 129

Met Lys Lys Arg Glu Gln Ser Asn Asp Ile Ala Arg Gly Phe Glu Arg
1               5                   10                  15

Gly Leu Glu Pro Glu Lys Ile Ile Gly Ala Thr Asp Ser Cys Gly Asp
            20                  25                  30

Leu Met Phe Leu Met Lys Trp Lys Asp Thr Asp Glu Ala Asp Leu Val
        35                  40                  45

Leu Ala Lys Glu Ala Asn Val Lys Cys Pro Gln Ile Val Ile Ala Phe
    50                  55                  60

Tyr Glu Glu Arg Leu Thr Trp His Ala Tyr Pro Glu Asp Ala Glu Asn
65                  70                  75                  80

Lys Glu Lys Ala Ser Pro Lys Lys Arg Lys Val Leu Glu Gly Gly
                85                  90                  95

Gly Gly Ser Gly Thr Cys Arg Ser Arg Pro Gly Glu Arg Pro Phe Gln
            100                 105                 110

Cys Arg Ile Cys Met Arg Asn Phe Ser Xaa Xaa Xaa Xaa Xaa Xaa His
        115                 120                 125

Thr Arg Thr His Thr Gly Glu Lys Pro Phe Gln Cys Arg Ile Cys Met
    130                 135                 140

Arg Asn Phe Ser Xaa Xaa Xaa Xaa Xaa Xaa His Leu Arg Thr His Thr
145                 150                 155                 160

Gly Ser Gln Lys Pro Phe Gln Cys Arg Ile Cys Met Arg Asn Phe Ser
                165                 170                 175

Xaa Xaa Xaa Xaa Xaa Xaa His Leu Arg Thr His Thr Gly Glu Lys Pro
            180                 185                 190

Phe Gln Cys Arg Ile Cys Met Arg Asn Phe Ser Xaa Xaa Xaa Xaa Xaa
        195                 200                 205

Xaa His Leu Lys Thr His Thr Gly Ser Gln Lys Pro Phe Gln Cys Arg
    210                 215                 220

Ile Cys Met Arg Asn Phe Ser Xaa Xaa Xaa Xaa Xaa Xaa His Leu Arg
225                 230                 235                 240

Thr His Thr Gly Glu Lys Pro Phe Gln Cys Arg Ile Cys Met Arg Asn
                245                 250                 255

Phe Ser Xaa Xaa Xaa Xaa Xaa Xaa His Leu Arg Thr His Leu Arg Gly
            260                 265                 270

Ser

<210> SEQ ID NO 130
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(40)
```

-continued

```
<223> OTHER INFORMATION: Any amino acid
<220> FEATURE:
<221> NAME/KEY: MOD_RES
<222> LOCATION: (62)..(67)
<223> OTHER INFORMATION: Any amino acid
<220> FEATURE:
<221> NAME/KEY: MOD_RES
<222> LOCATION: (90)..(95)
<223> OTHER INFORMATION: Any amino acid
<220> FEATURE:
<221> NAME/KEY: MOD_RES
<222> LOCATION: (117)..(122)
<223> OTHER INFORMATION: Any amino acid
<220> FEATURE:
<221> NAME/KEY: MOD_RES
<222> LOCATION: (145)..(150)
<223> OTHER INFORMATION: Any amino acid
<220> FEATURE:
<221> NAME/KEY: MOD_RES
<222> LOCATION: (172)..(177)
<223> OTHER INFORMATION: Any amino acid

<400> SEQUENCE: 130

Met Phe Glu Pro Lys Lys Arg Lys Val Phe Glu Gly Thr Ala Ser
  1               5                  10                  15

Ser Arg Pro Gly Glu Arg Pro Phe Gln Cys Arg Ile Cys Met Arg Asn
             20                  25                  30

Phe Ser Xaa Xaa Xaa Xaa Xaa Xaa His Thr Arg Thr His Thr Gly Glu
             35                  40                  45

Lys Pro Phe Gln Cys Arg Ile Cys Met Arg Asn Phe Ser Xaa Xaa Xaa
 50                  55                  60

Xaa Xaa Xaa His Leu Arg Thr His Thr Gly Ser Gln Lys Pro Phe Gln
 65                  70                  75                  80

Cys Arg Ile Cys Met Arg Asn Phe Ser Xaa Xaa Xaa Xaa Xaa Xaa His
                 85                  90                  95

Leu Arg Thr His Thr Gly Glu Lys Pro Phe Gln Cys Arg Ile Cys Met
                100                 105                 110

Arg Asn Phe Ser Xaa Xaa Xaa Xaa Xaa Xaa His Leu Lys Thr His Thr
            115                 120                 125

Gly Ser Gln Lys Pro Phe Gln Cys Arg Ile Cys Met Arg Asn Phe Ser
130                 135                 140

Xaa Xaa Xaa Xaa Xaa Xaa His Leu Arg Thr His Thr Gly Glu Lys Pro
145                 150                 155                 160

Phe Gln Cys Arg Ile Cys Met Arg Asn Phe Ser Xaa Xaa Xaa Xaa Xaa
                165                 170                 175

Xaa His Leu Arg Thr His Leu Arg Gly Ser Thr Cys Arg Asp Glu Phe
            180                 185                 190

Pro Thr Met Val Phe Pro Ser Gly Gln Ile Ser Gln Ala Ser Ala Leu
            195                 200                 205

Ala Pro Ala Pro Pro Gln Val Leu Pro Gln Ala Pro Ala Pro Ala Pro
210                 215                 220

Ala Pro Ala Met Val Ser Ala Leu Ala Gln Ala Pro Ala Pro Val Pro
225                 230                 235                 240

Val Leu Ala Pro Gly Pro Pro Gln Ala Val Ala Pro Ala Pro Lys
            245                 250                 255

Pro Thr Gln Ala Gly Glu Gly Thr Leu Ser Glu Ala Leu Leu Gln Leu
            260                 265                 270

Gln Phe Asp Asp Glu Asp Leu Gly Ala Leu Leu Gly Asn Ser Thr Asp
            275                 280                 285

Pro Ala Val Phe Thr Asp Leu Ala Ser Val Asp Asn Ser Glu Phe Gln
```

```
              290                 295                 300

Gln Leu Leu Asn Gln Gly Ile Pro Val Ala Pro His Thr Thr Glu Pro
305                 310                 315                 320

Met Leu Met Glu Tyr Pro Glu Ala Thr Arg Leu Val Thr Gly Ala Gln
                325                 330                 335

Arg Pro Pro Asp Pro Ala Pro Ala Pro Leu Gly Ala Pro Gly Leu Pro
            340                 345                 350

Asn Gly Leu Leu Ser Gly Asp Glu Asp Phe Ser Ile Ala Asp Met
        355                 360                 365

Asp Phe Ser Ala Leu Leu Ser Gln Ile Ser Ser
    370                 375
```

<210> SEQ ID NO 131
<211> LENGTH: 1851
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
attttcaaac cagaagaact acgacaggca ctgatgccaa ctttggaggc actttaccgt    60
caggatccag aatcccttcc ctttcgtcaa cctgtggacc ctcagctttt aggaatccct   120
gattactttg atattgtgaa gagccccatg gatctttcta ccattaagag gaagttagac   180
actggacagt atcaggagcc ctggcagtat gtcgatgata tttggcttat gttcaataat   240
gcctggttat ataaccggaa aacatcacgg gtatacaaat actgctccaa gctctctgag   300
gtctttgaac aagaaattga cccagtgatg caaagccttg gatactgttg tggcagaaag   360
ttggagttct ctccacagac actgtgttgc tacggcaaac agttgtgcac aatacctcgt   420
gatgccactt attacagtta ccagaacagg tatcatttct gtgagaagtg tttcaatgag   480
atccaagggg agagcgtttc tttgggggat gacccttccc agcctcaaac tacaataaat   540
aaagaacaat tttccaagag aaaaaatgac acactggatc ctgaactgtt tgttgaatgt   600
acagagtgcg gaagaaagat gcatcagatc tgtgtccttc accatgagat catctggcct   660
gctggattcg tctgtgatgg ctgtttaaag aaaagtgcac gaactaggaa agaaaataag   720 tttttctgcta aaaggttgcc atctaccaga cttggcacct ttctagagaa tcgtgtgaat   780
gactttctga ggcgacagaa tcaccctgag tcaggagagg tcactgttag agtagttcat   840
gcttctgaca aaaccgtgga agtaaaacca ggcatgaaag caaggtttgt ggacagtgga   900
gagatggcag aatcctttcc ataccgaacc aaagccctct tgcctttga agaaattgat    960 ggtgttgacc tgtgcttctt tggcatgcat gttcaagagt atggtctga ctgcccctcca  1020 cccaaccaga ggagagtata catatcttac ctcgatagtg ttcatttctt ccgtcctaaa  1080
tgcttgagga ctgcagtcta tcatgaaatc ctaattggat atttagaata tgtcaagaaa  1140
ttaggttaca caacagggca tatttgggca tgtccaccaa gtgagggaga tgattatatc  1200
ttccattgcc atcctcctga ccagaagata cccaagccca agcgactgca ggaatggtac  1260
aaaaaaatgc ttgacaaggc tgtatcgag cgtattgtcc atgactacaa ggatatttt   1320 aaacaagcta ctgaagatag attaacaagt gcaaggaat tgccttattt cgagggtgat   1380
ttctggccca tgttctgga agaaagcatt aaggaactgg aacaggagga agagagaga   1440 aaacgagagg aaaacaccag caatgaaagc acagatgtga ccaagggaga cagcaaaat  1500 gctaaaaaga gaataataa gaaaaccagc aaaaataaga gcagcctgag tagggcaac  1560
```

| | |
|---|---|
| aagaagaaac ccgggatgcc caatgtatct aacgacctct cacagaaact atatgccacc | 1620 |
| atggagaagc ataaagaggt cttctttgtg atccgcctca ttgctggccc tgctgccaac | 1680 |
| tccctgcctc ccattgttga tcctgatcct ctcatcccct gcgatctgat ggatggtcgg | 1740 |
| gatgcgtttc tcacgctggc aagggacaag cacctggagt tctcttcact ccgaagagcc | 1800 |
| cagtggtcca ccatgtgcat gctggtggag ctgcacacgc agagccagga c | 1851 |

<210> SEQ ID NO 132
<211> LENGTH: 2373
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

| | |
|---|---|
| aaggggata ctaggcacct gaacggggag gaggatgctg gtgggcggga agatagtata | 60 |
| ttggttaatg gcgcatgcag cgaccagtca tccgatagcc cacctatcct ggaggctatc | 120 |
| aggactccag agatacgagg gcgaagaagc tcttcacgcc tttccaagcg cgaagtgagt | 180 |
| agcctgctca gttatactca ggatttgaca ggcgacggcg acggggagga cggtgacggg | 240 |
| agtgacaccc ccgtgatgcc gaagctcttt cgggaaaccc ggaccaggag cgaaagcccc | 300 |
| gcagtaagga cgcgaaacaa caactccgtg tctagtcggg agagacatcg accttcaccc | 360 |
| cgcagcaccc gaggtcggca gggtaggaac catgtcgatg agagcccggt agagttcccc | 420 |
| gctactagaa gcctccggag acgcgctaca gcttcagccg gcacaccatg gcctagtcct | 480 |
| ccgtcaagtt acctcaccat tgacctcacc gatgatacag aagataccca tggtacaccc | 540 |
| cagtcttcca gcacgcccta cgcacgcttg gcccaagact cacagcaagg gggcatggag | 600 |
| tccccacagg tcgaggcaga ttctggagac ggggatagtt cagagtacca ggatggcaag | 660 |
| gagtttggga taggtgacct cgtttggggt aaaataaagg gcttctcatg gtggccagct | 720 |
| atggttgtgt catggaaggc aacttctaaa cggcaagcga tgtccggaat gcgctgggtg | 780 |
| cagtggttcg gagacgggaa attttcagag gtctctgctg ataaactcgt tgcgcttgga | 840 |
| ttgtttagcc aacactttaa cttggcgact tttaacaagc tcgtgtcata tcgaaaggcc | 900 |
| atgtatcatg cccttgagaa ggcgcgagta cgagccggga agactttccc gtccagtcca | 960 |
| ggggactcac tggaagatca gcttaaaccc atgcttgaat gggcacatgg cggtttcaag | 1020 |
| ccaaccggga tcgaaggatt gaagccgaac aatacacaac cagaaaataa gacgcggcgg | 1080 |
| cgaactgctg atgatagcgc tacctcagat tactgcccag caccgaagcg gttgaagaca | 1140 |
| aactgctata taacggaaa agacagaggg gacgaggacc agtctagaga acaaatggcg | 1200 |
| agtgatgtcg ccaacaataa atcctcactg gaggatgggt gcctgtcatg tgggcgcaaa | 1260 |
| aaccctgtaa gttttcatcc attgtttgaa gggggtctct gccagacttg tcgagatcgg | 1320 |
| ttttttggagc tgttctatat gtacgatgat gacgatatc aatcatattg tacagtttgc | 1380 |
| tgcgagggac gcgaactcct cctgtgttca aatacgagct gctgtcgctg tttttgtgta | 1440 |
| gagtgccttg aggtcctcgt agggacgggt actgctgctg aggctaaact gcaagaaccc | 1500 |
| tggtcttgtt acatgtgtct gccgcaacga tgtcacggtg ttctccgaag aagaaggac | 1560 |
| tggaatgtcc gactgcaagc ttttttttacc tctgacaccg ggttggaata tgaagctccg | 1620 |
| aagctgtatc cggccattcc agcagcccgg cggcgaccta ttcgggtcct gtcactgttc | 1680 |
| gacggaatcg cgacaggata tctcgtattg aaggaacttg gaatcaaggt cgggaaatac | 1740 |

```
gtggcgtcag aggtttgtga agaaagcatt gctgtaggaa ccgttaaaca cgaaggaaat    1800
attaagtatg tcaacgatgt gcgaaacatc acgaagaaga atatcgagga atggggaccg    1860
ttcgacctcg tcatcggggg cagtccatgc aacgacctga gtaatgtaaa tcctgcccgg    1920
aagggtctct atgaaggcac tgggcgactc tttttcgagt tttaccacct gctcaactat    1980
agtaggccta agaagggga cgaccgacct tcttctgga tgttcgaaaa tgtcgtagcc    2040
atgaaggtag gagataaaag agacatttct cgcttcctcg aatgtaaccc agttatgatc    2100
gatgcaataa aggtatctgc agcacaccga gcacgctatt tttggggaaa ccttcctggt    2160
atgaatcgcc ctgttatcgc cagcaagaac gataagctcg aattgcagga ttgtctcgaa    2220
tacaacagga ttgcaaagga tctctggctc agttgtgctc tgcatcgccg cgtccaacat    2280
gggccatggt gcccgccaga ggcggctgga aaagttctgg agcgcgcgtg tcacccaact    2340
cctttgagac caagcgaggg tctcctctgt atg                                 2373

<210> SEQ ID NO 133
<211> LENGTH: 3566
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
attgattatt gactagtgcg ccgggttttg gcgcctcccg cgggcgcccc cctcctcacg     60
gcgagcgctg ccacgtcaga cgaagggcgc agcgagcgtc ctgatccttc cgcccggacg    120
ctcaggacag cggcccgctg ctcataagac tcggccttag aaccccagta tcagcagaag    180
gacattttag gacgggactt gggtgactct agggcactgg ttttctttcc agagagcgga    240
acaggcgagg aaaagtagtc ccttctcggc gattctgcgg agggatctcc gtgggcggt    300 gaacgccgat gattatataa ggacgcgccg ggtgtggcac agctagttcc gtcgcagccg    360
ggatttgggt cgcggttctt gtttgtggat cgctgtgatc gtcacttggt gagtagcggg    420
ctgctgggct ggccggggct ttcgtggccg ccgggccgct cggtgggacg gaagcgtgtg    480
gagagaccgc caagggctgt agtctgggtc cgcgagcaag gttgccctga actggggtt    540 gggggagcg cacaaaatgg cggctgttcc cgagtcttga atggaagacg cttgtaaggc    600
gggctgtgag gtcgttgaaa caaggtgggg ggcatggtgg gcggcaagaa cccaaggtct    660
tgaggccttc gctaatgcgg gaaagctctt attcgggtga gatgggctgg ggcaccatct    720
ggggaccctg acgtgaagtt tgtcactgac tggagaactc ggtttgtcgt ctgttgcggg    780
ggcggcagtt atggcggtgc cgttgggcag tgcacccgta ccttttggag gcgcgcgcct    840
cgtcgtgtcg tgacgtcacc cgttctgttg gcttataatg cagggtgggg ccacctgccg    900
gtaggtgtgc ggtaggcttt tctccgtcgc aggacgcagg gttcgggcct agggtaggct    960
ctcctgaatc gacaggcgcc ggacctctgg tgagggagag gataagtgag gcgtcagttt   1020
ctttggtcgg ttttatgtac ctatcttctt aagtagctga agctccggtt ttgaactatg   1080 cgctcgggt tggcgagtgt gttttgtgaa gttttttagg cacctttga aatgtaatca    1140 tttgggtcaa tatgtaattt tcagtgttag actagtaaat tgtccgctaa attctggccg   1200 ttttttggctt ttttgttaga cacgcgttta attaagccgc caccatgttc gaacccaaga   1260
agaagagaaa ggtgttcgaa actagtgtgc ccctgtatgg cttcacttcc atttgtggcc   1320
gacggcctga aatggaagcc gcggtgtcaa ccataccacg gtttctgcag agctcatcag   1380
```

```
gctccatgct ggacggacgc tttgatccac agtctgccgc acatttcttt ggagtctacg    1440
acggccacgg gggcagccag gtcgccaact actgcaggga aaggatgcat ttggcacttg    1500
ccgaagagat cgccaaagag aagcccatgt tgtgtgatgg ggatacctgg ctggagaagt    1560
ggaagaaagc gcttttttaac tcttttctga gagtggattc tgagatagaa tctgtcgcac    1620
ccgagaccgt gggcagcaca tccgtcgtag ccgtagtgtt tccctcccac atattcgtcg    1680
ccaactgcgg cgacagtcga gccgtcctct gccgaggtaa gaccgccctg cctctgagtg    1740
ttgaccataa gcccgaccgg gaggatgagg ccgcccgaat cgaggccgcc ggtggaaaag    1800
tcatccaatg gaacggcgca agagtgttcg gcgtgctggc gatgtccagg agcattggag    1860
accggtacct gaagcccagc ataatcccag atcccgaagt gaccgcagtc aagagggtga    1920
aagaggacga ttgtctgatc ctggctagcg atggcgtatg ggacgtgatg actgatgagg    1980
aggcgtgtga aatggcccgc aagcgaatcc tgctgtggca taaaaaaaac gcagtcgcgg    2040
gggacgcttc tcttctggca gacgaaaggc gcaaagaagg taaagacccg gctgctatga    2100
gcgccgccga atatctcagt aagctggcaa ttcagcgagg gtccaaagac aacatttccg    2160
tggtcgtggt agacctcaaa ggcggttccg gcggttctag acccggagag cgcccattcc    2220
agtgtcggat ttgcatgcgg aacttttcga gaagacacgg cctggacaga catacccgta    2280
ctcatacagg tgaaaaaccc tttcagtgtc ggatctgtat gcgaaatttc tccgaccaca    2340
gcagcctgaa gagacatcta cgtacccaca ccggcagcca gaagccattt cagtgtcgga    2400
tctgtatgcg gaacttctcc gtgagacaca acctgaccag acatctacgt acgcacaccg    2460
gagagaagcc attccaatgc cgaatatgca tgcgcaactt cagtgaccac agcaacctga    2520
gcagacacct aaaaacccac accggttccc agaagccatt tcagtgtcgg atctgtatgc    2580
ggaacttctc ccagcgcagc agcctggtga gacatctacg tacgcacacc ggagagaagc    2640
cattccaatg ccgaatatgc atgcgcaact tcagtgagag cggccacctg aagagacacc    2700
tgcgtacgca cctgagggga tccccgaaga aaaaacggaa agtgggcgga agcggagcta    2760
ctaacttcag cctgctgaag caggctggag acgtggagga gaaccctgga cctggtcacc    2820
atgggcgcgc cgacgcgctg gacgatttcg atctcgacat gctgggttct gatgccctcg    2880
atgactttga cctggatatg ttgggaagcg acgcattgga tgactttgat ctggacatgc    2940
tcggctccga tgctctggac gatttcgatc tcgatatgtt aggtggtggc agcggtcaat    3000
tgactcaaga cgaattcacc caactctccc aatcaatcgc cgagttccac acgtaccaac    3060
tcggtaacgg ccgttgctca tctctcctag ctcagcgaat ccacgcgccg ccggaaacag    3120
tatggtccgt ggtgagacgt ttcgataggc cacagattta caaacacttc atcaaaagct    3180
gtaacgtgag tgaagatttc gagatgcgag tgggatgcac gcgcgacgtg aacgtgataa    3240
gtggattacc ggcgaatacg tctcgagaga gattagatct gttggacgat gatcggagag    3300 tgactggggtt tagtataacc ggtggtgaac ataggctgag gaattataaa tcggttacga    3360
cggttcatag atttgagaaa gaagaagaag aagaaaggat ctggaccgtt gttttggaat    3420
cttatgttgt tgatgtaccg gaaggtaatt cggaggaaga tacgagattg tttgctgata    3480
cggttattag attgaatctt cagaaacttg cttcgatcac tgaagctatg aacggttatc    3540
cgtacgacgt accagactac gcataa                                        3566
```

<210> SEQ ID NO 134
<211> LENGTH: 2
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 134

Gly Ser
1

<210> SEQ ID NO 135
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Ser Gly Ser
1

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Ser Gly Ser Gly Ser
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Ser Gly Ser Gly Ser Gly Ser
1               5

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Ser Gly Ser Gly Ser Gly Ser Gly Ser
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Ser Gly Ser Gly Ser Gly Ser Gly Ser Gly Ser
1               5                   10
```

```
<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Ser Gly Ser Gly Ser Gly Ser Gly Ser Gly Ser Gly Ser
1               5                   10

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Ser Gly Ser Gly Ser Gly Ser Gly Ser Gly Ser Gly Ser Gly Ser
1               5                   10                  15

<210> SEQ ID NO 142
<211> LENGTH: 298
<212> TYPE: PRT
<213> ORGANISM: Arabidopsis thaliana

<400> SEQUENCE: 142

Val Pro Leu Tyr Gly Phe Thr Ser Ile Cys Gly Arg Arg Pro Glu Met
1               5                   10                  15

Glu Ala Ala Val Ser Thr Ile Pro Arg Phe Leu Gln Ser Ser Ser Gly
                20                  25                  30

Ser Met Leu Asp Gly Arg Phe Asp Pro Gln Ser Ala Ala His Phe Phe
            35                  40                  45

Gly Val Tyr Asp Gly His Gly Gly Ser Gln Val Ala Asn Tyr Cys Arg
        50                  55                  60

Glu Arg Met His Leu Ala Leu Ala Glu Glu Ile Ala Lys Glu Lys Pro
65                  70                  75                  80

Met Leu Cys Asp Gly Asp Thr Trp Leu Glu Lys Trp Lys Lys Ala Leu
                85                  90                  95

Phe Asn Ser Phe Leu Arg Val Asp Ser Glu Ile Glu Ser Val Ala Pro
            100                 105                 110

Glu Thr Val Gly Ser Thr Ser Val Val Ala Val Val Phe Pro Ser His
        115                 120                 125

Ile Phe Val Ala Asn Cys Gly Asp Ser Arg Ala Val Leu Cys Arg Gly
    130                 135                 140

Lys Thr Ala Leu Pro Leu Ser Val Asp His Lys Pro Asp Arg Glu Asp
145                 150                 155                 160

Glu Ala Ala Arg Ile Glu Ala Ala Gly Lys Val Ile Gln Trp Asn
                165                 170                 175

Gly Ala Arg Val Phe Gly Val Leu Ala Met Ser Arg Ser Ile Gly Asp
            180                 185                 190

Arg Tyr Leu Lys Pro Ser Ile Ile Pro Asp Pro Glu Val Thr Ala Val
        195                 200                 205

Lys Arg Val Lys Glu Asp Asp Cys Leu Ile Leu Ala Ser Asp Gly Val
    210                 215                 220
```

```
Trp Asp Val Met Thr Asp Glu Glu Ala Cys Glu Met Ala Arg Lys Arg
225                 230                 235                 240

Ile Leu Leu Trp His Lys Lys Asn Ala Val Ala Gly Asp Ala Ser Leu
            245                 250                 255

Leu Ala Asp Glu Arg Arg Lys Glu Gly Lys Asp Pro Ala Ala Met Ser
        260                 265                 270

Ala Ala Glu Tyr Leu Ser Lys Leu Ala Ile Gln Arg Gly Ser Lys Asp
    275                 280                 285

Asn Ile Ser Val Val Val Asp Leu Lys
    290                 295

<210> SEQ ID NO 143
<211> LENGTH: 177
<212> TYPE: PRT
<213> ORGANISM: Arabidopsis thaliana

<400> SEQUENCE: 143

Thr Gln Asp Glu Phe Thr Gln Leu Ser Gln Ser Ile Ala Glu Phe His
1               5                   10                  15

Thr Tyr Gln Leu Gly Asn Gly Arg Cys Ser Ser Leu Leu Ala Gln Arg
            20                  25                  30

Ile His Ala Pro Pro Glu Thr Val Trp Ser Val Val Arg Arg Phe Asp
        35                  40                  45

Arg Pro Gln Ile Tyr Lys His Phe Ile Lys Ser Cys Asn Val Ser Glu
    50                  55                  60

Asp Phe Glu Met Arg Val Gly Cys Thr Arg Asp Val Asn Val Ile Ser
65                  70                  75                  80

Gly Leu Pro Ala Asn Thr Ser Arg Glu Arg Leu Asp Leu Leu Asp Asp
                85                  90                  95

Asp Arg Arg Val Thr Gly Phe Ser Ile Thr Gly Gly Glu His Arg Leu
            100                 105                 110

Arg Asn Tyr Lys Ser Val Thr Thr Val His Arg Phe Glu Lys Glu Glu
        115                 120                 125

Glu Glu Glu Arg Ile Trp Thr Val Val Leu Glu Ser Tyr Val Val Asp
    130                 135                 140

Val Pro Glu Gly Asn Ser Glu Glu Asp Thr Arg Leu Phe Ala Asp Thr
145                 150                 155                 160

Val Ile Arg Leu Asn Leu Gln Lys Leu Ala Ser Ile Thr Glu Ala Met
                165                 170                 175

Asn

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
```

```
                50                  55                  60
Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Glu
            100                 105

<210> SEQ ID NO 145
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Trp His Glu Gly Leu Glu Glu Ala Ser Arg Leu Tyr Phe Gly Glu
 1               5                  10                  15

Arg Asn Val Lys Gly Met Phe Glu Val Leu Glu Pro Leu His Ala Met
             20                  25                  30

Met Glu Arg Gly Pro Gln Thr Leu Lys Glu Thr Ser Phe Asn Gln Ala
         35                  40                  45

Tyr Gly Arg Asp Leu Met Glu Ala Gln Glu Trp Cys Arg Lys Tyr Met
     50                  55                  60

Lys Ser Gly Asn Val Lys Asp Leu Thr Gln Ala Trp Asp Leu Tyr Tyr
 65                  70                  75                  80

His Val Phe Arg Arg Ile Ser Lys Gln
                 85

<210> SEQ ID NO 146
<211> LENGTH: 315
<212> TYPE: PRT
<213> ORGANISM: Homo sapiens

<400> SEQUENCE: 146

Ala Gly Asp Met Arg Ala Ala Asn Leu Trp Pro Ser Pro Leu Met Ile
 1               5                  10                  15

Lys Arg Ser Lys Lys Asn Ser Leu Ala Leu Ser Leu Thr Ala Asp Gln
             20                  25                  30

Met Val Ser Ala Leu Leu Asp Ala Glu Pro Pro Ile Leu Tyr Ser Glu
         35                  40                  45

Tyr Asp Pro Thr Arg Pro Phe Ser Glu Ala Ser Met Met Gly Leu Leu
     50                  55                  60

Thr Asn Leu Ala Asp Arg Glu Leu Val His Met Ile Asn Trp Ala Lys
 65                  70                  75                  80

Arg Val Pro Gly Phe Val Asp Leu Thr Leu His Asp Gln Val His Leu
                 85                  90                  95

Leu Glu Cys Ala Trp Leu Glu Ile Leu Met Ile Gly Leu Val Trp Arg
            100                 105                 110

Ser Met Glu His Pro Val Lys Leu Leu Phe Ala Pro Asn Leu Leu Leu
        115                 120                 125

Asp Arg Asn Gln Gly Lys Cys Val Glu Gly Met Val Glu Ile Phe Asp
    130                 135                 140

Met Leu Leu Ala Thr Ser Ser Arg Phe Arg Met Met Asn Leu Gln Gly
145                 150                 155                 160

Glu Glu Phe Val Cys Leu Lys Ser Ile Ile Leu Leu Asn Ser Gly Val
```

```
                165                 170                 175
Tyr Thr Phe Leu Ser Ser Thr Leu Lys Ser Leu Glu Glu Lys Asp His
            180                 185                 190

Ile His Arg Val Leu Asp Lys Ile Thr Asp Thr Leu Ile His Leu Met
            195                 200                 205

Ala Lys Ala Gly Leu Thr Leu Gln Gln Gln His Gln Arg Leu Ala Gln
            210                 215                 220

Leu Leu Leu Ile Leu Ser His Ile Arg His Met Ser Asn Lys Gly Met
225                 230                 235                 240

Glu His Leu Tyr Ser Met Lys Cys Lys Asn Val Val Pro Leu Tyr Asp
                245                 250                 255

Leu Leu Leu Glu Ala Ala Asp Ala His Arg Leu His Ala Pro Thr Ser
            260                 265                 270

Arg Gly Gly Ala Ser Val Glu Glu Thr Asp Gln Ser His Leu Ala Thr
            275                 280                 285

Ala Gly Ser Thr Ser Ser His Ser Leu Gln Lys Tyr Tyr Ile Thr Gly
            290                 295                 300

Glu Ala Glu Gly Phe Pro Ala Thr Ala Val Asp
305                 310                 315

<210> SEQ ID NO 147
<211> LENGTH: 617
<212> TYPE: PRT
<213> ORGANISM: Homo sapiens

<400> SEQUENCE: 147

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30

Asp Pro Gln Leu Leu Gly Ile Pro Asp Tyr Phe Asp Ile Val Lys Ser
            35                  40                  45

Pro Met Asp Leu Ser Thr Ile Lys Arg Lys Leu Asp Thr Gly Gln Tyr
50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
            85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
            115                 120                 125

Cys Cys Tyr Gly Lys Gln Leu Cys Thr Ile Pro Arg Asp Ala Thr Tyr
            130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
            195                 200                 205

Gln Ile Cys Val Leu His His Glu Ile Ile Trp Pro Ala Gly Phe Val
            210                 215                 220
```

```
Cys Asp Gly Cys Leu Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
            245                 250                 255

Asn Arg Val Asn Asp Phe Leu Arg Arg Gln Asn His Pro Glu Ser Gly
        260                 265                 270

Glu Val Thr Val Arg Val Val His Ala Ser Asp Lys Thr Val Glu Val
    275                 280                 285

Lys Pro Gly Met Lys Ala Arg Phe Val Asp Ser Gly Glu Met Ala Glu
    290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
        355                 360                 365

Glu Ile Leu Ile Gly Tyr Leu Glu Tyr Val Lys Lys Leu Gly Tyr Thr
    370                 375                 380

Thr Gly His Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
            420                 425                 430

Val His Asp Tyr Lys Asp Ile Phe Lys Gln Ala Thr Glu Asp Arg Leu
        435                 440                 445

Thr Ser Ala Lys Glu Leu Pro Tyr Phe Glu Gly Asp Phe Trp Pro Asn
450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Asn Asn Lys Lys Thr Ser Lys Asn
            500                 505                 510

Lys Ser Ser Leu Ser Arg Gly Asn Lys Lys Pro Gly Met Pro Asn
        515                 520                 525

Val Ser Asn Asp Leu Ser Gln Lys Leu Tyr Ala Thr Met Glu Lys His
530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
        595                 600                 605

Val Glu Leu His Thr Gln Ser Gln Asp
    610                 615

<210> SEQ ID NO 148
<211> LENGTH: 792
<212> TYPE: PRT
```

<213> ORGANISM: Homo sapiens

<400> SEQUENCE: 148

```
Met Lys Gly Asp Thr Arg His Leu Asn Gly Glu Glu Asp Ala Gly Gly
1               5                  10                  15
Arg Glu Asp Ser Ile Leu Val Asn Gly Ala Cys Ser Asp Gln Ser Ser
            20                  25                  30
Asp Ser Pro Pro Ile Leu Glu Ala Ile Arg Thr Pro Glu Ile Arg Gly
        35                  40                  45
Arg Arg Ser Ser Ser Arg Leu Ser Lys Arg Glu Val Ser Ser Leu Leu
    50                  55                  60
Ser Tyr Thr Gln Asp Leu Thr Gly Asp Gly Asp Gly Glu Asp Gly Asp
65                  70                  75                  80
Gly Ser Asp Thr Pro Val Met Pro Lys Leu Phe Arg Glu Thr Arg Thr
                85                  90                  95
Arg Ser Glu Ser Pro Ala Val Arg Thr Arg Asn Asn Asn Ser Val Ser
            100                 105                 110
Ser Arg Glu Arg His Arg Pro Ser Pro Arg Ser Thr Arg Gly Arg Gln
        115                 120                 125
Gly Arg Asn His Val Asp Glu Ser Pro Val Glu Phe Pro Ala Thr Arg
    130                 135                 140
Ser Leu Arg Arg Arg Ala Thr Ala Ser Ala Gly Thr Pro Trp Pro Ser
145                 150                 155                 160
Pro Pro Ser Ser Tyr Leu Thr Ile Asp Leu Thr Asp Asp Thr Glu Asp
                165                 170                 175
Thr His Gly Thr Pro Gln Ser Ser Thr Pro Tyr Ala Arg Leu Ala
            180                 185                 190
Gln Asp Ser Gln Gln Gly Gly Met Glu Ser Pro Gln Val Glu Ala Asp
        195                 200                 205
Ser Gly Asp Gly Asp Ser Ser Glu Tyr Gln Asp Gly Lys Glu Phe Gly
    210                 215                 220
Ile Gly Asp Leu Val Trp Gly Lys Ile Lys Gly Phe Ser Trp Trp Pro
225                 230                 235                 240
Ala Met Val Val Ser Trp Lys Ala Thr Ser Lys Arg Gln Ala Met Ser
                245                 250                 255
Gly Met Arg Trp Val Gln Trp Phe Gly Asp Gly Lys Phe Ser Glu Val
            260                 265                 270
Ser Ala Asp Lys Leu Val Ala Leu Gly Leu Phe Ser Gln His Phe Asn
        275                 280                 285
Leu Ala Thr Phe Asn Lys Leu Val Ser Tyr Arg Lys Ala Met Tyr His
    290                 295                 300
Ala Leu Glu Lys Ala Arg Val Arg Ala Gly Lys Thr Phe Pro Ser Ser
305                 310                 315                 320
Pro Gly Asp Ser Leu Glu Asp Gln Leu Lys Pro Met Leu Glu Trp Ala
                325                 330                 335
His Gly Gly Phe Lys Pro Thr Gly Ile Glu Gly Leu Lys Pro Asn Asn
            340                 345                 350
Thr Gln Pro Glu Asn Lys Thr Arg Arg Thr Ala Asp Asp Ser Ala
        355                 360                 365
Thr Ser Asp Tyr Cys Pro Ala Pro Lys Arg Leu Lys Thr Asn Cys Tyr
    370                 375                 380
Asn Asn Gly Lys Asp Arg Gly Asp Glu Asp Gln Ser Arg Glu Gln Met
385                 390                 395                 400
```

-continued

```
Ala Ser Asp Val Ala Asn Asn Lys Ser Ser Leu Glu Asp Gly Cys Leu
                    405                 410                 415

Ser Cys Gly Arg Lys Asn Pro Val Ser Phe His Pro Leu Phe Glu Gly
        420                 425                 430

Gly Leu Cys Gln Thr Cys Arg Asp Arg Phe Leu Glu Leu Phe Tyr Met
            435                 440                 445

Tyr Asp Asp Asp Gly Tyr Gln Ser Tyr Cys Thr Val Cys Cys Glu Gly
450                 455                 460

Arg Glu Leu Leu Leu Cys Ser Asn Thr Ser Cys Arg Cys Phe Cys
465                 470                 475                 480

Val Glu Cys Leu Glu Val Leu Val Gly Thr Gly Thr Ala Ala Glu Ala
                    485                 490                 495

Lys Leu Gln Glu Pro Trp Ser Cys Tyr Met Cys Leu Pro Gln Arg Cys
                500                 505                 510

His Gly Val Leu Arg Arg Arg Lys Asp Trp Asn Val Arg Leu Gln Ala
            515                 520                 525

Phe Phe Thr Ser Asp Thr Gly Leu Glu Tyr Glu Ala Pro Lys Leu Tyr
530                 535                 540

Pro Ala Ile Pro Ala Ala Arg Arg Pro Ile Arg Val Leu Ser Leu
545                 550                 555                 560

Phe Asp Gly Ile Ala Thr Gly Tyr Leu Val Leu Lys Glu Leu Gly Ile
                    565                 570                 575

Lys Val Gly Lys Tyr Val Ala Ser Glu Val Cys Glu Glu Ser Ile Ala
                580                 585                 590

Val Gly Thr Val Lys His Glu Gly Asn Ile Lys Tyr Val Asn Asp Val
            595                 600                 605

Arg Asn Ile Thr Lys Lys Asn Ile Glu Glu Trp Gly Pro Phe Asp Leu
610                 615                 620

Val Ile Gly Gly Ser Pro Cys Asn Asp Leu Ser Asn Val Asn Pro Ala
625                 630                 635                 640

Arg Lys Gly Leu Tyr Glu Gly Thr Gly Arg Leu Phe Phe Glu Phe Tyr
                    645                 650                 655

His Leu Leu Asn Tyr Ser Arg Pro Lys Glu Gly Asp Asp Arg Pro Phe
                660                 665                 670

Phe Trp Met Phe Glu Asn Val Val Ala Met Lys Val Gly Asp Lys Arg
            675                 680                 685

Asp Ile Ser Arg Phe Leu Glu Cys Asn Pro Val Met Ile Asp Ala Ile
                690                 695                 700

Lys Val Ser Ala Ala His Arg Ala Arg Tyr Phe Trp Gly Asn Leu Pro
705                 710                 715                 720

Gly Met Asn Arg Pro Val Ile Ala Ser Lys Asn Asp Lys Leu Glu Leu
                    725                 730                 735

Gln Asp Cys Leu Glu Tyr Asn Arg Ile Ala Lys Asp Leu Trp Leu Ser
                740                 745                 750

Cys Ala Leu His Arg Arg Val Gln His Gly Pro Trp Cys Pro Pro Glu
            755                 760                 765

Ala Ala Gly Lys Val Leu Glu Arg Ala Cys His Pro Thr Pro Leu Arg
770                 775                 780

Pro Ser Glu Gly Leu Leu Cys Met
785                 790

<210> SEQ ID NO 149
<211> LENGTH: 7
<212> TYPE: PRT
```

```
<213> ORGANISM: Simian virus 40

<400> SEQUENCE: 149

Pro Lys Lys Lys Arg Lys Val
1               5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Phe Glu Gly Thr Ala Ser
1               5

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

His Thr Arg Thr His
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

His Leu Lys Thr His
1               5

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Leu Glu Gly Gly Gly Gly Ser Gly Thr Cys Arg
1               5                   10
```